United States Patent [19]

Morton, Jr.

[11] 4,238,414

[45] Dec. 9, 1980

[54] 2-DECARBOXY-2-AMINOMETHYL-6A-CARBA-PGI$_2$ COMPOUNDS

[75] Inventor: Douglas R. Morton, Jr., Portage, Mich.

[73] Assignee: The Upjohn Company, Kalamazoo, Mich.

[21] Appl. No.: 79,658

[22] Filed: Sep. 27, 1979

Related U.S. Application Data

[62] Division of Ser. No. 877,253, Feb. 13, 1978.

[51] Int. Cl.$^3$ ................. C07C 91/02; C07C 91/40
[52] U.S. Cl. ................. 564/453; 260/340.5 P;
260/345.9 P; 560/53; 560/56; 560/119; 560/256;
562/462; 562/466; 562/501; 424/269; 424/305;
424/308; 424/317; 424/320; 424/324; 424/325;
424/330; 424/331; 424/339; 424/341; 424/343
[58] Field of Search ................. 260/563 P, 570.9, 571;
424/325, 330

[56] References Cited

U.S. PATENT DOCUMENTS

| 3,776,940 | 12/1973 | Just et al. | 260/563 P X |
| 3,862,979 | 1/1975 | Gandolfi et al. | 260/514 D |
| 3,935,240 | 1/1976 | Mallion | 260/570.9 X |

OTHER PUBLICATIONS

Bundy et al., "Tetrahedron Letters", No. 16, pp. 1371–1374 (1978).
Kojima et al., "Tetrahedron Letters", No. 39, pp. 3743–3746 (1978).
Nicolaou et al., "J.C.S., Chemical Communications", p. 1067 (1978).

Primary Examiner—John Doll
Attorney, Agent, or Firm—Robert A. Armitage

[57] ABSTRACT

The present invention relates to novel 2-decarboxy-2-aminomethyl-6a-carba-PGI$_2$ compounds, which are useful for inducing a variety of prostacyclin-like pharmacological effects. Accordingly, these compounds are useful pharmacological agents for the same purposes for which prostacyclin is employed.

68 Claims, No Drawings

2-DECARBOXY-2-AMINOMETHYL-6A-CARBA-PGI₂ COMPOUNDS

DESCRIPTION
2-Decarboxy-2-aminomethyl-6a-carba-PGI₂ compounds

CROSS REFERENCE TO RELATED APPLICATION

The present application is a divisional application of U.S. Ser. No. 877,253, filed Feb. 13, 1978, now pending issuance as a United States patent.

BACKGROUND OF THE INVENTION

The present invention relates to novel 2-decarboxy-2-aminomethyl-6a-carba-PGI₂ compounds, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention are described in Appendix A of this specification.

SUMMARY OF THE INVENTION

The present invention particularly provides:
A compound of the formula

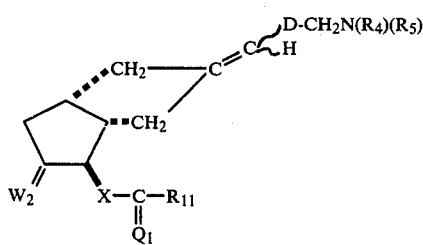

wherein $W_2$ is $\alpha\text{-OH}:\beta\text{-H}$, $\alpha\text{-H}:\beta\text{-OH}$, oxo, o; $\alpha\text{-H}:\beta\text{-H}$;
wherein D is
(1) $-(CH_2)_2-$, wherein d is one to 5, inclusive,
(2) $-(CH_2)_d-CF_2-$, wherein d is one to 5, inclusive,
(3) $-(CH_2)_k-CH=CH-$, wherein k is one or 2;
wherein one of $R_4$ and $R_5$ is hydrogen, and the other is hydrogen, alkyl of one to 12 carbon atoms, inclusive, benzyl, or phenyl;
wherein $R_{11}$ is $$-C(R_{12})(R_{13})-C_gH_{2g}-CH_3, \quad (1)$$

wherein $C_gH_{2g}$ is alkylene of one to 9 carbon atoms, inclusive, with one to 5 carbon atoms, inclusive, in the chain between $-CR_{12}R_{13}-$ and terminal methyl, wherein $R_{12}$ and $R_{13}$ are hydrogen, alkyl of one to 4 carbon atoms, inclusive, or fluoro, being the same or different, with the proviso that one of $R_{12}$ and $R_{13}$ is fluoro only when the other is hydrogen or fluoro;

$$-C(R_{12})(R_{13})-Z-(Ph), \quad (2)$$

wherein $R_{12}$ and $R_{13}$ are as defined above; wherein Z represents an oxa atom $(-O-)$ or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive between $-CR_{12}R_{13}-$ and (Ph), wherein (Ph) is phenyl or phenyl substituted by (T)s, wherein T is alkyl of one to 4 carbon atoms, inclusive, fluoro, chloro, trifluoromethyl, or $-OR_{14}$, wherein $R_{14}$ is alkyl of one to 4 carbon atoms, inclusive, and s is zero, one, 2, or 3, with the proviso that not more than two T's are other than alkyl and when s is 2 or 3 the T's are either the same or different; or $$\text{cis}-CH_2-CH=CH-CH_2CH_3; \quad (3)$$

wherein $Q_1$ is $\alpha\text{-OH}:\beta\text{-R}_8$ or $\alpha\text{-R}_8:\beta\text{-OH}$, wherein $R_8$ is hydrogen or methyl;
wherein X is trans$-CH=CH-$, cis$-CH=CH-$, $-C\equiv C-$, or $-CH_2CH_2-$.

With regard to the divalent substituents described in the claims, e.g., Q and $W_1$, these divalent radicals are defined as $\alpha\text{-R}_i:\beta\text{-R}_j$, where $R_i$ represents a substituent of the divalent moiety of the alpha configuration with respect to the cyclopentane and $R_j$ represents a substituent of the divalent moiety of the beta configuration with respect to the cyclopentane ring. Accordingly, when Q is defined as $\alpha\text{-OH}:\beta\text{-R}_8$, the hydroxy of the Q moiety is in the alpha configuration, i.e., as in prostacyclin, and the $R_8$ substituent is in the beta configuration. Not all carbon atoms to which such divalent moieties are attached represent asymmetric centers. For example, when both valence bonds are to hydrogen (e.g., $W_1$ or Q is $\alpha\text{-H}:\beta\text{-H}$), then no asymmetric center is present.

DESCRIPTION OF THE PREFERRED EMBODIMENTS

The present invention particularly relates to the following chemical compounds:
2-Decarboxy-2-aminomethyl-(5E)-6a-carba-13,13-dihydro-PGI₂;
2-Decarboxy-2-aminomethyl-(5Z)-6a-carba-13,14-dihydro-PGI₂;
2-Decarboxy-2-aminomethyl-(5E)-6a-carba-13,14-dihydro-(15S)-15-methyl-PGI₂;
2-Decarboxy-2-aminomethyl-(5Z)-6a-carba-13,14-dihydro-(15S)-15-methyl-PGI₂;
2-Decarboxy-2-aminomethyl-(5E)-6a-carba-11β-PGI₂;
2-Decarboxy-2-aminomethyl-(5Z)-6a-carba-11β-PGI₂;
2-Decarboxy-2-aminomethyl-(5E)-6a-carba-11-dehydro-PGI₂;
2-Decarboxy-2-aminomethyl-(5Z)-6a-carba-11-dehydro-PGI₂;
2-Decarboxy-2-aminomethyl-(5E)-6a-carba-11-deoxy-PGI₂;
2-Decarboxy-2-aminomethyl-(5Z)-6a-carba-11-deoxy-PGI₂;
2-Decarboxy-2-aminomethyl-(5E)-6a-carba-PGI₂;
2-Decarboxy-2-aminomethyl-(5Z)-6a-carba-PGI₂;
2-Decarboxy-2-aminomethyl-(5E)-6a-carba-16,16-dimethyl-PGI₂;
2-Decarboxy-2-aminomethyl-(5Z)-6a-carba-16,16-dimethyl-PGI₂;
2-Decarboxy-2-aminomethyl-(5E)-6a-carba-PGI₃;
2-Decarboxy-2-aminomethyl-(5Z)-6a-carba-PGI₃;
2-Decarboxy-2-aminomethyl-(5E)-6a-carba-2a,2b-dihomo-PGI₂;
2-Decarboxy-2-aminomethyl-(5Z)-6a-carba-2a,2b-dihomo-PGI₂;
2-Decarboxy-2-aminomethyl-(5E)-6a-carba-2a,2b-dihomo-16,16-dimethyl-PGI₂;
2-Decarboxy-2-aminomethyl-(5Z)-6a-carba-2a,2b-dihomo-16,16-dimethyl-PGI₂;
2-Decarboxy-2-aminomethyl-(5E)-6a-carba-2,2-difluoro-PGI₂;

2-Decarboxy-2-aminomethyl-(5Z)-6a-carba-2,2-difluoro-PGI$_2$;

2-Decarboxy-2-aminomethyl-(5E)-6a-carba-2,2-difluoro-16,16-dimethyl-PGI$_2$;

2-Decarboxy-2-aminomethyl-(5Z)-6a-carba-2,2-difluoro-16,16-dimethyl-PGI$_2$;

2-Decarboxy-2-aminomethyl-(5E)-6a-carba-(15S)-15-methyl-PGI$_2$;

2-Decarboxy-2-aminomethyl-(5Z)-6a-carba-(15S)-15-methyl-PGI$_2$;

2-Decarboxy-2-aminomethyl-(5E)-6a-carba-2a,2b-dihomo-(15S)-15-methyl-PGI$_2$;

2-Decarboxy-2-aminomethyl-(5Z)-6a-carba-2a,2b-dihomo-(15S)-15-methyl-PGI$_2$;

2-Decarboxy-2-aminomethyl-(5E)-6a-carba-2,2-difluoro-(15S)-15-methyl-PGI$_2$;

2-Decarboxy-2-aminomethyl-(5Z)-6a-carba-2,2-difluoro-(15S)-15-methyl-PGI$_2$;

2-Decarboxy-2-aminomethyl-(5E)-6a-carba-15R-PGI$_2$;

2-Decarboxy-2-aminomethyl-(5Z)-6a-carba-15R-PGI$_2$;

2-Decarboxy-2-aminomethyl-(5E)-6a-carba-(15R)-15-methyl-PGI$_2$; and

2-Decarboxy-2-aminomethyl-(5Z)-6a-carba-(15R)-15-methyl-PGI$_2$.

APPENDIX A

BACKGROUND OF THE INVENTION

This invention relates to products having prostacyclin-like structure and to processes for preparing them. In particular this invention relates to 6a-carba prostacyclin analogs, i.e. compounds with a pentalene structure, and to processes for preparing them and their intermediates.

Prostacyclin, an organic compound related to prostaglandins, is (5Z)-9-deoxy-6,9α-epoxy-Δ$^5$-PGF$_1$ and is represented by the formula

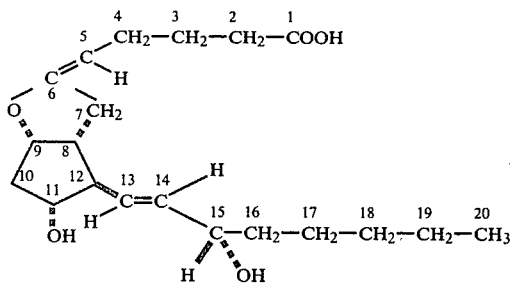

For its synthesis and structure see for example R. A. Johnson et al., J. Am. Chem. Soc. 99, 4182 (1977) and Prostaglandins 12, 915 (1976), and E. J. Corey et al., J. Am. Chem. Soc. 99, 2006 (1977). For some of its biological properties and uses see the references cited in the Johnson publications. Prostacyclin is referred to as "PGI$_2$", see Anonymous, Prostaglandins 13, 375 (1977). It is alternately named as 6,9α-oxido-9α,15α-dihydroxy-prosta-(Z)5, (E)13-dienoic acid.

An isomer of prostacyclin is (5E)-9-deoxy-6,9α-epoxy-Δ$^5$-PGF$_1$ and is represented by the formula

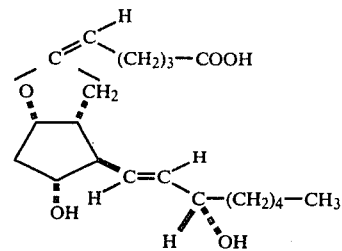

See R. A. Johnson et al., J. Am. Chem. Soc. 99, 4182 (1977). As to the "Z" and "E" nomenclature for stereoisomerism about a double bond, see for example J. E. Blackwood et al., J. Am. Chem. Soc. 90, 509 (1968).

As drawn herein, each formula represents a specific optically active isomer corresponding to the absolute configuration of naturally occurring prostaglandin E$_1$ (PGE$_1$) which is represented by the formula

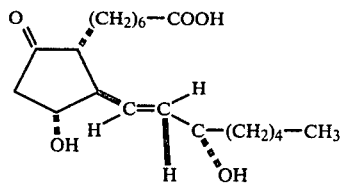

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

The prostaglandins and analogs are well-known organic compounds derived from prostanoic acid which has the following structure and atom numbering:

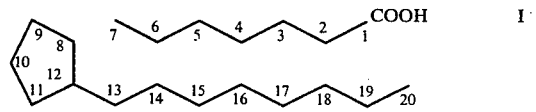

For background on prostaglandins, see for example Bergstrom et al., Pharmacol. Rev. 20, 1 (1968), as well as numerous publications and patents.

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin systhetase inhibitors.

Because of these biological responses, prostacyclin and prostacyclin-like compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of the sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro application such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Aggregation of platelets is inhibited by the presence of these compounds. For this purpose, the compound is added gradually or in single or multiple portions to the circulating blood, to the blood of the donor person or animal, to the perfused body portion, attached or detached, to the recipient, or to two or all of those at a total steady dose of about 0.001–1.0 $\mu$g./ml. of whole blood. These compounds are also useful in preparing platelet-rich concentrates from blood for use in treating thrombocytopenia or in chemotherapy.

Prostacyclin and prostacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-like compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory prostaglandin synthetase inhibitor. See Partridge et al., U.S. Pat. No. 3,781,429, for a disclosure as to certain prostaglandins of the E and A series, and see A. Robert, U.S. Pat. No. 3,917,828 as to PGF$\alpha$-type compounds. The dosage regimen for the prostacyclin or prostacyclin-type compound in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostacyclin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostacyclin or prostacyclin-type compound to reduce and then substantially to eliminate those undesirable effects.

Prostacyclin or prostacyclin-type compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the ringe of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

Prostacyclin or prostacyclin-type compounds are useful in mammals, including man, as nasal decongestants and are used for this purpose in a dose range of about 10 $\mu$g. to about 10 mg. per ml. of pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, non-patent ductus arteriosus, non-obstructive mesenteric ischemia, arteritis lymphangitis and the like. These examples are included to be illustrative and should not be construed as limiting the term peripheral vascular disease. For these conditions the prostacyclin compounds are administered orally or parenterally via injection or infusion directly into a vein or artery. The dosages of such compounds are in the range of 0.01–1.0 $\mu$g./kg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed. Prostacyclin or prostacyclin-type compounds are accordingly useful for treating peripheral vascular diseases in the extremities of humans who have circulatory insufficiencies in said extremities, such treatment affording relief of rest pain and induction of healing of ulcers. For a complete discussion of the nature of and clinical manifestations of human peripheral vascular disease and the method previously known of its treatment with prostaglandins see South African Patent No. 74/0149 referenced as Derwent Farmdoc No. 58400V. See Elliott, et al., Lancet, Jan. 18, 1975, pp. 140–142.

Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternateive route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo of a fetus is accomplished by similar administration of the compound during the first or second trimester of the normal mammalian gestation period.

Prostacyclin or prostacyclin-type compounds are further useful in causing cervical dilation in pregnant and non-pregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostacyclin compounds is also useful in operative gynecology such as D and G (Cervical Dilation and Uterine Curettage) where mechanical dilation may cause perforation of the uterus, cervical tears, or infections. It is also useful for diagnostic procedures where dilation is necessary for tissue examination. For these purposes, the prostacyclin compound is administered locally or systemically. The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

Prostacyclin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared. For those purposes, such compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intraor perilesionally, or subcutaneously, using appropriate sterile saline compositions.

Prostacyclin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

SUMMARY OF THE INVENTION

It is the purpose of this invention to provide novel products having pharmacological activity. It is a further purpose to provide processes for preparing these products and their intermediates.

Accordingly, there is provided a compound of the formula

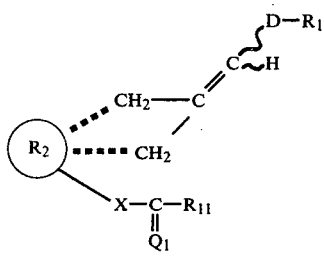 V including the lower alkanoates.

In formula V and in other formulas hereinafter including formulas in the Charts, the terms D, Q, $R_1$, and the like are as defined in the TABLE. Reference to that Table will establish what is intended to be represented by each formula.

In formula V as used herein, attachment to $R_2$ corresponds to bonds to the cyclopentane ring at the C-8, C-9, and C-12 positions following prostanoic acid numbering, thus,

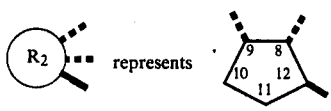

Within the scope of prostacyclin analogs represented by formula V and described herein, there are represented (a) PGI-type compounds when $R_2$ is

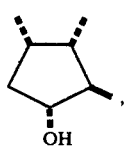, (b) 11β-PGI-type compounds when $R_2$ is

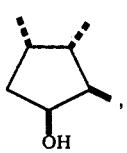, (c) 11-dehydro-PGI-type compounds when $R_2$ is

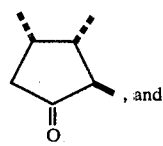, and (d) 11-deoxy-PGI-type compounds when $R_2$ is

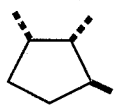.

TABLE
Definition of Terms for Formulas

A is
  alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive D is
  (1) —(CH$_2$)$_d$— wherein d is one to 5, inclusive,
  (2) —(CH$_2$)$_d$—CF$_2$—, or
  (3) —(CH$_2$)$_k$—CH=CH— wherein k is one or 2.

G is
  alkyl of one to 4 carbon atoms, inclusive, bromo, phenylalkyl of 7 to 10 carbon atoms, inclusive, or nitro.

Hal is
  chloro, bromo, or iodo.

Ms is
  mesylate, i.e. —SO$_2$CH$_3$.

Q is

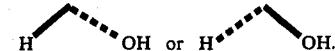

$Q_1$ is

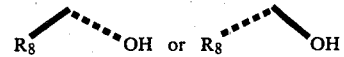

wherein $R_8$ is hydrogen or methyl.

$Q_2$ is

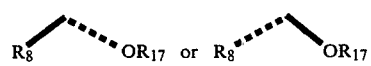

wherein $R_8$ is hydrogen or methyl, and $R_{17}$ is silyl of the formula —Si(A)$_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, being the same or different.

$Q_3$ is

wherein $R_8$ is hydrogen or methyl, and $R_{24}$ is carboxyacyl including

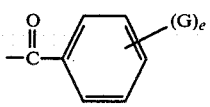
(a)

wherein "G" is alkyl of one to 4 carbon atoms, inclusive, bromo, phenylalkyl of 7 to 10 carbon atoms, inclusive, or nitro, and "e" is zero to 5, inclusive, provided that not more than two G's are other than alkyl, and that the total number of carbon atoms, in the G's does not exceed 10 carbon atoms,

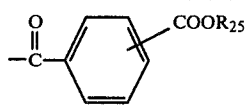
(b)

wherein $R_{25}$ is alkyl of one to 4 carbon atoms, inclusive,

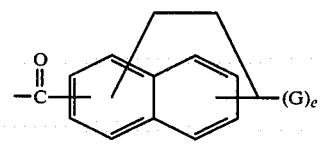
(c)

wherein "G" and "e" are as defined above, or

(d)

wherein $R_{26}$ is alkyl or one to 7 carbon atoms, inclusive.
$Q_4$ is

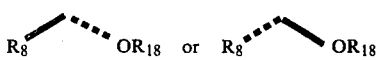

wherein $R_8$ is hydrogen or methyl, and $R_{18}$ is tetrahydropyran-2-yl, tetrahydrofuranyl, or a group of the formula

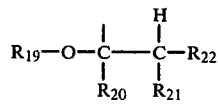

wherein $R_{19}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{20}$ and $R_{21}$ are the same or different, being hydrogen, alkyl of one to 4 carbon atoms, inclusive, phenyl or phenyl substituted with one, 2, or 3 alkyl of one to 4 carbon atoms, inclusive, or, when $R_{20}$ and $R_{21}$ are taken together, —(CH$_2$)$_a$— or —(CH$_2$)$_b$—O—(CH$_2$)$_c$— wherein "a" is 3, 4, or 5, b is one, 2, or 3, and c is one, 2, or 3 with the proviso that b plus c is 2, 3, or 4, and wherein $R_{22}$ is hydrogen or phenyl.
$Q_5$ is

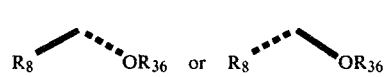

wherein $R_8$ is hydrogen or methyl, and $R_{36}$ is either silyl, $R_{17}$, as defined for $Q_2$ above, or tetrahydropyranyl or the like, $R_{18}$, as defined for $Q_4$ above.
$Q_6$ is

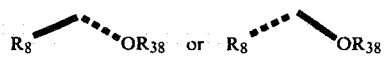

wherein $R_8$ is hydrogen or methyl, and $R_{38}$ is one of (1) silyl, $R_{17}$, as defined for $Q_2$ above, (2) tetrahydropyranyl or the like, $R_{18}$, as defined for $Q_4$ above, or (3) carboxyacyl, $R_{24}$, as defined for $Q_3$ above.
$R_1$ is
(1) —COOR$_3$
(2) —CH$_2$OH
(3) —CH$_2$N(R$_4$)(R$_5$)

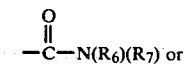
(4)

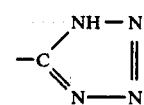
(5)

wherein $R_3$ is
(a) hydrogen
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl of one to 4 carbon atoms, inclusive,

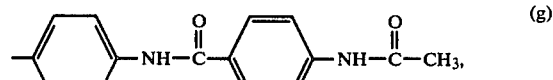
(g)

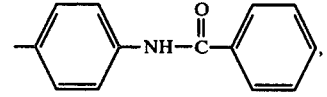
(h)

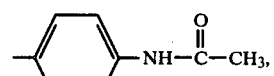
(i)

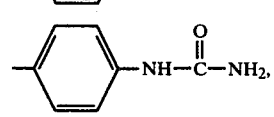
(j)

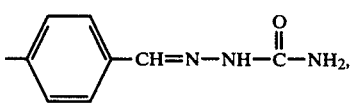
(k)

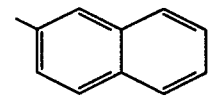
(l)

-continued

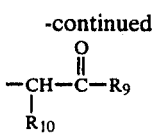
(m)

wherein $R_9$ is phenyl, p-bromophenyl, p-biphenylyl, p-nitrophenyl, p-benzamidophenyl, or 2-naphthyl, and wherein $R_{10}$ is hydrogen or benzoyl, or (n) a pharmacologically acceptable cation.

$R_2$ is

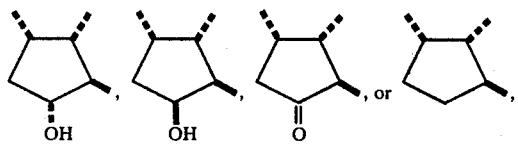

$R_3$ is
(a) hydrogen
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl of one to 4 carbon atoms, inclusive,

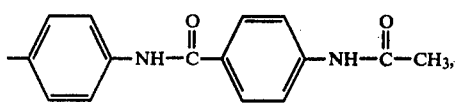
(g)

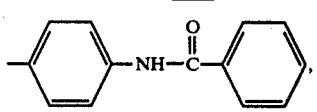
(h)

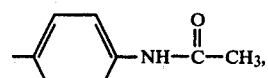
(i)

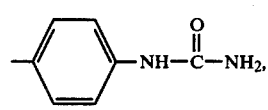
(j)

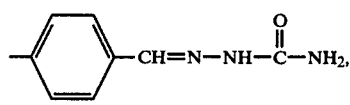
(k)

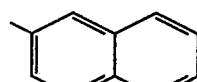
(l)

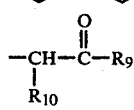
(m)

wherein $R_9$ is phenyl, p-bromophenyl, p-biphenylyl, p-nitrophenyl, p-benzamidophenyl, or 2-naphthyl, and wherein $R_{10}$ is hydrogen or benzoyl, or (n) a pharmacologically acceptable cation.

As to $R_4$ and $R_5$,
one is hydrogen and the other is hydrogen, alkyl of one to 12 carbon atoms, inclusive, benzyl, or phenyl.

As to $R_6$ and $R_7$,
one is hydrogen and the other is hydrogen, alkyl of one to 12 carbon atoms, inclusive, benzyl, phenyl, or methylsulfonyl of the formula $CH_3-SO_2-$.

$R_8$ is
hydrogen or methyl.

$R_9$ is
phenyl, p-bromophenyl, p-biphenylyl, p-nitrophenyl, p-benzamidophenyl, or 2-naphthyl.

$R_{10}$ is
hydrogen or benzoyl.

$R_{11}$ is $$-\underset{R_{13}}{\overset{R_{12}}{\underset{|}{\overset{|}{C}}}}-C_gH_{2g}-CH_3 \quad (1)$$

wherein $C_gH_{2g}$ is alkylene of one to 9 carbon atoms, inclusive, with one to 5 carbon atoms, inclusive, in the chain between $-CR_{12}R_{13}-$ and terminal methyl, wherein $R_{12}$ and $R_{13}$ are hydrogen, alkyl of one to 4 carbon atoms, inclusive, or fluoro, being the same or different, with the proviso that one of $R_{12}$ and $R_{13}$ is fluoro only when the other is hydrogen or fluoro;

$$-\underset{R_{13}}{\overset{R_{12}}{\underset{|}{\overset{|}{C}}}}-Z-\phantom{x}\text{(T)}_s \quad (2)$$

wherein $R_{12}$ and $R_{13}$ are as defined above; wherein Z represents an oxa atom ($-O-$) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between $-CR_{12}R_{13}-$ and the phenyl ring; wherein T is alkyl of one to 4 carbon atoms, inclusive, fluoro, chloro, trifluoromethyl, or $-OR_{14}-$ wherein $R_{14}$ is alkyl of one to 4 carbon atoms, inclusive, and s is zero, one, 2, or 3, with the proviso that not more than two T's are other than alkyl and when s is 2 or 3 the T's are either the same or different; or $$-CH_2\underset{H}{\diagdown}C=C\underset{H}{\diagup}CH_2CH_3 \quad (3)$$

$R_{12}$ and $R_{13}$ are
as defined above for $R_{11}$.

$R_{14}$ is
alkyl of one to 4 carbon atoms, inclusive.

$R_{15}$ is

[cyclopentyl structures with OH substituents]

$R_{16}$ is

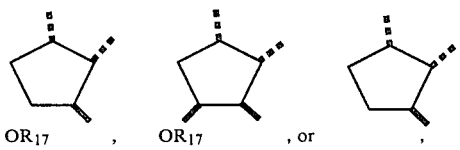

wherein $R_{17}$ is silyl of the formula $-Si(A)_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, being the same or different.

$R_{17}$ is
as defined above for 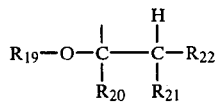.

$R_{18}$ is
tetrahydropyran-2-yl, tetrahydrofuranyl, or a group of the formula $$R_{19}-O-\underset{R_{20}}{\underset{|}{C}}-\underset{R_{21}}{\underset{|}{\overset{H}{\overset{|}{C}}}}-R_{22}$$

wherein $R_{19}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{20}$ and $R_{21}$ are the same or different, being hydrogen, alkyl of one to 4 carbon atoms, inclusive, phenyl or phenyl substituted with one, 2, or 3 alkyl of one to 4 carbon atoms, inclusive, or, when $R_{20}$ and $R_{21}$ are taken together, $-(CH_2)_a-$ or $-(CH_2)_b-O-(CH_2)_c-$ wherein "a" is 3, 4, or 5, b is one, 2, or 3, and c is one, 2, or 3 with the proviso that b plus c is 2, 3, or 4, and wherein $R_{22}$ is hydrogen or phenyl.

$R_{19}$, $R_{20}$, $R_{21}$, and $R_{22}$ are
as defined above for $R_{18}$.

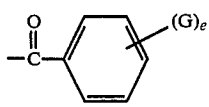 is

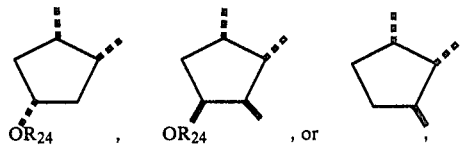

wherein $R_{24}$ is carboxyacyl including

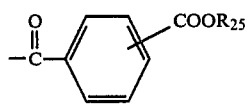 (a')

wherein "G" is alkyl of one to 4 carbon atoms, inclusive, bromo, phenylalkyl of 7 to 10 carbon atoms, inclusive, or nitro, and "e" is zero to 5, inclusive, provided that not more than two G's are other than alkyl, and that the total number of carbon atoms, in the G's does not exceed 10 carbon atoms,

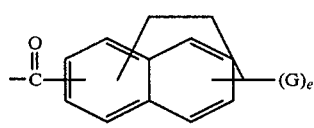 (b')

wherein $R_{25}$ is alkyl of one to 4 carbon atoms, inclusive,

 (c')

wherein "G" and "e" are as defined above, or

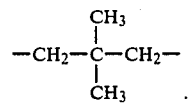 (d')

wherein $R_{26}$ is alkyl of one to 7 carbon atoms, inclusive.

$R_{24}$ is
as defined above for 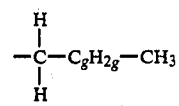.

$R_{25}$ is
alkyl of one to 4 carbon atoms, inclusive.

$R_{26}$ is
alkyl of one to 7 carbon atoms, inclusive.

$R_{27}$ and $R_{28}$ are
alkyl of one to 4 carbon atoms, inclusive, or, when taken together, $$-CH_2-\underset{CH_3}{\overset{CH_3}{\overset{|}{\underset{|}{C}}}}-CH_2-$$

$R_{29}$ is

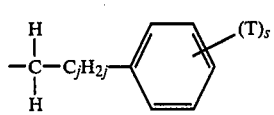 (1)

wherein $C_gH_{2g}$ is alkylene of one to 9 carbon atoms, inclusive, with one to 5 carbon atoms, inclusive, in the chain between $-CH_2-$ and terminal methyl, $$-\overset{H}{\underset{H}{\overset{|}{\underset{|}{C}}}}-C_jH_{2j}-\underset{\phantom{xx}}{\phantom{xx}}\text{(T)}_s$$ (2)

wherein $C_jH_{2j}$ is a valence bond or alkylene of one to 9 carbon atoms, inclusive, substituted with zero, one, or 2 fluoro, with one to 6 carbon atoms, inclusive between $-CH_2-$ and the phenyl ring; wherein T is alkyl of one to 4 carbon atoms, inclusive, fluoro, chloro, trifluoromethyl, or $-OR_{14}-$ wherein $R_{14}$ is alkyl of one to 4 carbon atoms, inclusive, and s is zero, one, 2, or 3, with the proviso that not more than two T's are other than alkyl and when s is 2 or 3 the T's are either the same or different; or $$-CH_2-C\equiv C-CH_2CH_3.$$ (3)

$R_{30}$ is
hydrogen, alkyl of one to 18 carbon atoms, inclusive, or aralkyl of 7 to 12 carbon atoms, inclusive, substituted with zero to 3 halo atoms.

$R_{31}$ is

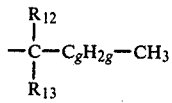

(1)

wherein $C_gH_{2g}$ is alkylene of one to 9 carbon atoms, inclusive, with one to 5 carbon atoms, inclusive, in the chain between $-CR_{12}R_{13}-$ and terminal methyl, wherein $R_{12}$ and $R_{13}$ are hydrogen, alkyl of one to 4 carbon atoms, inclusive, or fluoro, being the same or different, with the proviso that one of $R_{12}$ and $R_{13}$ is fluoro only when the other is hydrogen or fluoro; or

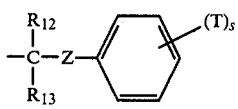

(2)

wherein $R_{12}$ and $R_{13}$ are as defined above with the proviso that neither $R_{12}$ nor $R_{13}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between $-CR_{12}R_{13}-$ and the phenyl ring; wherein T is alkyl of one to 4 carbon atoms, inclusive, fluoro, chloro, trifluoromethyl, or $-OR_{14}-$ wherein $R_{14}$ is alkyl of one to 4 carbon atoms, inclusive, and s is zero, one, 2, or 3, with the proviso that not more than two T's are other than alkyl and when s is 2 or 3 the T's are either the same or different.

$R_{32}$ is
hydrogen, bromo, or chloro.

$R_{33}$ is

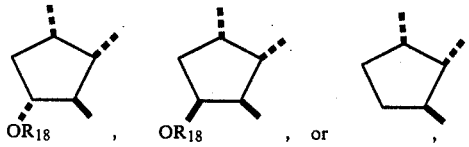

wherein $R_{18}$ is tetrahydropyran-2-yl, tetrahydrofuranyl, or a group of the formula

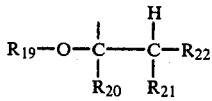

wherein $R_{19}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{20}$ and $R_{21}$ are the same or different, being hydrogen, alkyl of one to 4 carbon atoms, inclusive, phenyl or phenyl substituted with one, 2, or 3 alkyl of one to 4 carbon atoms, inclusive, or, when $R_{20}$ and $R_{21}$ are taken together, $-(CH_2)_a-$ or $-(CH_2)_b-O-(CH_2)_c-$ wherein "a" is 3, 4, or 5, b is one, 2, or 3, and c is one, 2, or 3 with the proviso that b plus c is 2, 3, or 4, and wherein $R_{22}$ is hydrogen or phenyl.

$R_{34}$ is
alkyl of one to 7 carbon atoms, inclusive.

$R_{35}$ is
bromo or chloro.

$R_{36}$ is
either silyl, $R_{17}$, or tetrahydropyranyl or the like, $R_{18}$, wherein $R_{17}$ and $R_{18}$ are as defined above.

$R_{37}$ is
alkyl of one to 4 carbon atoms, inclusive.

$R_{38}$ is
one of (1) silyl, $R_{17}$, (2) tetrahydropyranyl or the like, $R_{18}$, or (3) carboxyacyl, $R_{24}$, wherein $R_{17}$, $R_{18}$ and $R_{24}$ are as defined above.

$R_{39}$ is
hydrogen or $R_{37}$, wherein $R_{37}$ is alkyl of one to 4 carbon atoms, inclusive.

$R_{40}$ is
silyl, $R_{17}$, or $R_{37}$, wherein $R_{17}$ and $R_{37}$ are as defined above.

$R_{41}$ is

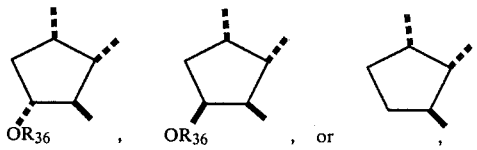

wherein $R_{36}$ is either silyl, $R_{17}$, or tetrahydropyranyl or the like, $R_{18}$, wherein $R_{17}$ and $R_{18}$ are as defined above.

$R_{42}$ is
methyl or ethyl.

T is
alkyl of one to 4 carbon atoms, inclusive, fluoro, chloro, trifluoromethyl, or $-OR_{14}$ wherein $R_{14}$ is alkyl of one to 4 carbon atoms, inclusive, and s is zero, one, 2 or 3, with the proviso that not more than two T's are other than alkyl and when s is 2 or 3 the T's are either the same or different.

X is
trans—CH=CH—, cis—CH=CH—, —C≡C—, or —CH$_2$CH$_2$—.

Z is
an oxa atom (—O—) or $C_jH_{2j}$ is a valence bond or alkylene of one to 9 carbon atoms, inclusive, substituted with zero, one, or 2 fluoro, with one to 6 carbon atoms, inclusive, between $-CR_{12}R_{13}-$ and the phenyl ring.

a is
3, 4, or 5.

b is
one, 2, or 3.

c is
one, 2, or 3 with the proviso that b plus c is 2, 3, or 4.

d is
one to 5, inclusive.

e is
zero to 5, inclusive.

k is
one or 2.

s is
zero, one, 2, or 3.

Wavy line (∿) indicates
attachment in alpha or beta configuration.

$C_gH_{2g}$ is
alkylene of one to 9 carbon atoms, inclusive, with one to 5 carbon atoms, inclusive, in the chain between $-CR_{12}R_{13}-$ and terminal methyl.

$C_jH_{2j}$ is
a valence bond or alkylene of one to 9 carbon atoms, inclusive, substituted with zero, one, or 2 fluoro, with one to 6 carbon atoms, inclusive between —CR$_{12}$R$_{13}$— and the phenyl ring.

Further within the scope of the prostacyclin analogs described herein there are represented
(a) PGI-type compounds when X is trans—CH=CH—,
(b) 13,14-cis-PGI-type compounds when X is cis—CH=CH—,
(c) 13,14-dihydro-PGI-type compounds when X is —CH$_2$CH$_2$—, and
(d) 13,14-didehydro-PGI-type compounds when X is —C≡C—.

Still further within the scope of the prostaglandin analogs described herein there are represented
(a) acids, esters, and salts when R$_1$ is —COOR$_3$,
(b) 2-decarboxy-2-hydroxymethyl-type compounds when R$_1$ is —CH$_2$OH,
(c) 2-decarboxy-2-aminomethyl-type compounds when R$_1$ is —CH$_2$N(R$_4$)(R$_5$),
(d) amides when R$_1$ is $$\underset{\underset{\|}{O}}{-C}-N(R_6)(R_7), \text{ and}$$

(e) 2-decarboxy-2-tetrazol-1-yl-type compounds when R$_1$ is

For those compounds of formula V wherein Q$_1$ is

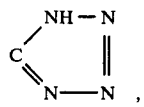

i.e., wherein the C-15 hydroxyl group is attached to the side chain in alpha configuration, the configuration at C-15 is identical with that of the naturally occurring prostaglandins such as PGE$_1$ obtained from mammalian tissues. The 15-epimer compounds are represented by formula V when Q$_1$ is

and are identified variously as "15-epi", "15β", or "15R" by the appropriate prefix in the name. As is known in the art, "R" and "S" designations depend on the neighboring substituents. See R. S. Cahn, J. Chem. Ed. 41, 116 (1964). See also Nelson, J. Medic. Chem. 17, 911 (1974) and J. Am. Chem. Soc. 99, 7362 (1977).

A typical example of a compound of formula V is represented by the formula

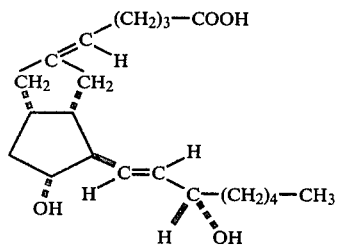

and named (5E)-6a-Carba-PGI$_2$. Alternately, the name is [3aS-[3aα,4α(1E, 3R*), 5β, 6aα]]-5-[Hexahydro-5-hydroxy-4-(3-hydroxy-1-octenyl)-2(1H)-pentalenylidene]pentanoic acid.

Following general organic nomenclature, the term "6a-carba" indicates that the heterocyclic oxygen atom in the prostacyclin molecule is replaced with the carbon of a methylene group.

The compound of formula VI is a species of the formula-V compounds wherein R$_2$ is D is —(CH$_2$)$_3$—, Q$_1$ is

R$_1$ is —COOH, R$_{11}$ is n-pentyl, X is trans-CH=CH— and the C-5/C-6 substituents bonded by wavy lines (∼) are in the E configuration.

As to the "Z" and "E" nomenclature for stereoisomerism about a double bond, see for example J. E. Blackwood et al., J. Am. Chem. Soc. 90, 509 (1968).

Formula VII is illustrative of another species compound of this invention named (5E)-2a,2b-Dihomo-6a-carba-16,16-dimethyl-PGI$_2$. In that name, "2a,2b-dihomo" signifies two additional carbon atoms in the carboxy-terminated side chain specifically between the C-2 and C-3 carbon atoms. There are, therefore, seven carbon atoms in that side chain instead of the five found in prostacyclin attached to the C-6 carbon atoms. From the end of the chain to the double bond they are identified as C-1, C-2, C-2a, C-2b, C-3, C-4, and C-5. The carbon atoms connected by the double bond are C-5 and C-6.

In generic formula V, the term D also provides for shorter chain lengths. Accordingly, if D is methylene, the name contains the term "dinor" to indicate that two carbon atoms are missing, more specifically "2,3-dinor" indicating the absence of the C-2 and C-3 carbon atoms, following the system of nomenclature used in the art. The same system applies to the hydroxy-substituted side chain.

Other compounds of this invention are named following the conventions applied in the art for prostaglandins and prostacyclins. For example

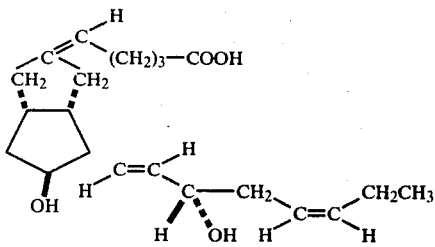
VIII is named (5Z)-6a-Carba-11β-PGI₃.

The novel 6a-carba-prostacyclin-type compounds of formula V have many of the same pharmacological properties and cause many of the same biological responses as prostacyclins. Each of these compounds is therefore useful for at least one of the pharmacological purposes indicated above for prostacyclins. For example, these 6a-carba-prostacyclins are especially useful for inhibition of platelet aggregation, reduction of the adhesive character of platelets, and the removal or prevention of formation of platelet thrombi in mammals including man. Such applications include treatment and prevention of myocardial infarcts and cerebral ischemic attacks, treatment and prevention of postoperative (surgical) thrombosis, and in vitro applications such as the storage of blood or platelets. The methods of administration and dosages are similar to those described above for prostacyclins.

Further, these 6a-carba-prostacyclin-type compounds are surprisingly more stable chemically than prostacyclin, which property is advantageous in formulating and administering these compounds. Their stability to acid is particularly beneficial for oral administration.

With respect to formula V and the definition of terms in the TABLE, examples of alkyl of one to 4 carbon atoms, inclusive, are methyl, ethyl, propyl, butyl, and isomeric forms thereof. Examples of alkyl of one to 7 carbon atoms, inclusive, are those given above and pentyl, hexyl, heptyl, and isomeric forms thereof. Examples of alkyl of one to 18 carbon atoms, inclusive, are those given above and octyl, nonyl, decyl, undecyl, dodecyl, tridecyl, tetradecyl, pentadecyl, hexadecyl, heptadecyl, octadecyl, and isomeric forms thereof. Examples of cycloalkyl of 3 to 10 carbon atoms, inclusive, which includes alkyl-substituted cycloalkyl, are
cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.

Examples of phenylalkyl of 7 to 10 carbon atoms, inclusive, are
benzyl,
phenethyl,
1-phenylethyl,
2-phenylpropyl,
4-phenylbutyl,
3-phenylbutyl.

Examples of aralkyl of 7 to 12 carbon atoms, inclusive, include those for phenylalkyl above and
2-(1-naphthylethyl), and
1-(2-naphthylmethyl).

Examples of aralkyl of 7 to 12 carbon atoms, inclusive, substituted with zero to 3 halo atoms include those above and
α-chlorobenzyl,
(o-, m-, or p-chloro)benzyl, and
(2,6-dichloro)benzyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH₃)—, —C(CH₃)₂—, —CH(CH₂CH₃)—, —CH₂—CH(CH₃)—, —CH(CH₃)—CH(CH₃)—, —CH₂—C(CH₃)₂—, —CH₂—CH(CH₃)—CH₃—, —CH₂—CH₂—CH(CH₂CH₂CH₃)—, —CH(CH₃)—CH(CH₃)—CH₂—CH₂—, —CH₂—CH₂—CH₂—C(CH₃)₂—CH₂, and —CH₂—CH₂—CH₂—CH₂—CH(CH₃)—.

Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or more carbon atoms thereof, and including those alkylene groups with one or 2 fluoro substituents on one or 2 carbon atoms thereof, e.g. —CF₂—CH₂—, —CHF—CHF—, —CH₂—CH₂—CF₂—, —CH₂—CHF—CH₂—, —CH₂—CH₂—CF(CH₃)—, —CH₂—CH₂—CF₂—CH₂—, —CH(CH₃)—CH₂—CH₂—CHF—, —CH₂—CH₂—CH₂—CH₂—CF₂—, —CHF—CH₂—CH₂—CH₂—CH₂—CHF, —CF₂—CH₂—CH₂—CH₂—CH₂—CH₂—, —CH₂—CH₂—CH₂—CF₂—CH₂—CH₂—, and —CH₂—CH₂—CH₂—CH₂—CF₂.

Examples of phenyl substituted by one, 2, or 3 chloro or alkyl of one to 4 carbon atoms, inclusive, are
(o-, m-, or p-)tolyl,
p-ethylphenyl,
p-tert-butylphenyl,
2,5-dimethylphenyl,
(o-, m-, or p-)chlorophenyl,
(o-, m-, or p-)fluorophenyl,
4-fluoro-2,5-xylyl,
4-chloro-3-fluorophenyl, and
α,α,α-trifluoro-(o-, m-, or p-)tolyl.

Examples of

as defined above are phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
6-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
6-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl,
(4- or 5-chloro-2-methoxyphenyl, and
2-chloro(4- or 5-)methoxyphenyl.

Included in the compounds of formula V are the pharmacologically acceptable salts when $R_3$ is a cation. Such pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of the formula V are preferred. For example it is preferred that $Q_1$ be

wherein it is especially preferred that $R_8$ be hydrogen or methyl.

Another preference, for the compounds of formula V is that $R_3$ in —COOR$_3$ be either hydrogen or alkyl or one to 4 carbon atoms, inclusive, especially methyl or ethyl, for optimum absorption on administration, or a salt of a pharmacologically acceptable cation.

For purposes of stability on long storage, it is preferred that $R_3$ in —COOR$_3$ for compounds of formula V be amido-substituted phenyl or substituted phenacyl, as illustrated herein.

For oral administration it is preferred that $R_1$ in compounds of formula V be

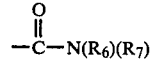

wherein one of $R_6$ and $R_7$ is hydrogen and the other is hydrogen, methyl, or methylsulfonyl.

When $R_{11}$ in the compounds of formula V is

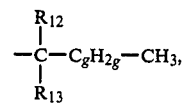

it is preferred that $C_gH_{2g}$ be alkylene of 2, 3, or 4 carbon atoms, and especially that it be trimethylene. It is further preferred that $R_{12}$ and $R_{13}$ be hydrogen, methyl, ethyl, or fluoro, being the same or different. If is further preferred, when $R_{12}$ and $R_{13}$ are not hydrogen, that both $R_{12}$ and $R_{13}$ be methyl or fluoro. It is especially preferred that $R_{11}$ be n-pentyl, 1,1-dimethylpentyl, or 1,1-difluorophentyl.

When $R_{11}$ in the compounds of formula V is

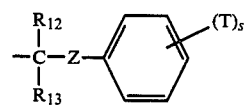

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_{12}$ and $R_{13}$ be hydrogen, methyl, or fluoro, being the same or different. It is further preferred, when $R_{12}$ and $R_{13}$ are not hydrogen, that both $R_{12}$ and $R_{13}$ be methyl. When Z is $C_jH_{2j}$, it is preferred that $C_jH_{2j}$ be a valence bond, methylene, or ethylene. It is especially preferred that $R_{11}$ be

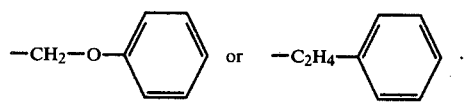

As to variations in $R_2$ in the compounds of formula V, it is preferred that $R_2$ be

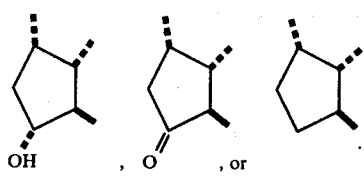

As to variations in D in compound of formula V, it is preferred that D be —$(CH_2)_3$—, —$(CH_2)_4$—, or —$(CH_2)_5$—, and especially —$(CH_2)_3$—.

As to X in compounds of formula V, it is preferred that X be trans —CH=CH—.

The 6a-carba-prostacyclin compounds of formula V, including those of formulas VI-VIII, are produced by reactions and procedures described and exemplified hereinafter, as shown schematically in the charts.

Accordingly there is provided a process for preparing a compound of the formula

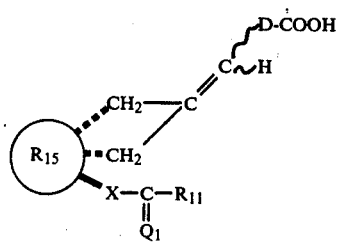     IX wherein D, $Q_1$, $R_{11}$, $R_{15}$, X, and ～ are as defined in the TABLE, which comprises the steps of starting with a compound of the formula

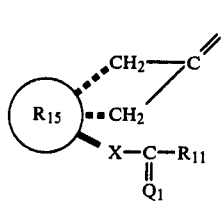     X and (1) transforming it to a compound of the formula

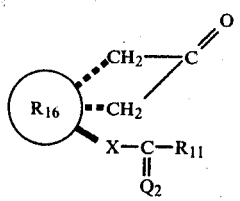     XI (2) reacting the product of step (1) with the carbanion of a sulfoximine of the formula

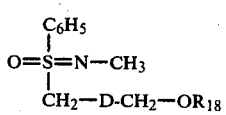     XII to form a compound of the formula

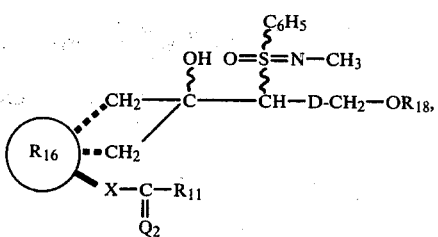     XIII (3) subjecting the product of step (2) to reductive elimination to form a compound of the formula

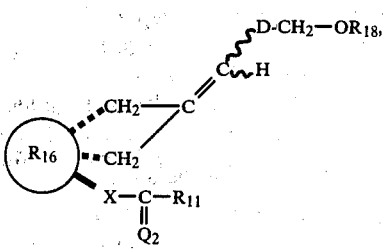     XIV (4) preferentially removing silyl groups, $R_{17}$, from the product of step (3) to form a compound of the formula

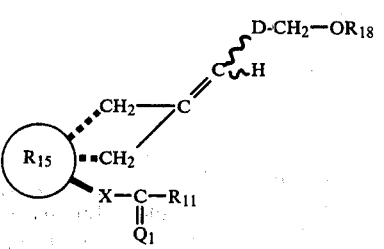     XV (5) acylating the product of step (4) to form a compound of the formula

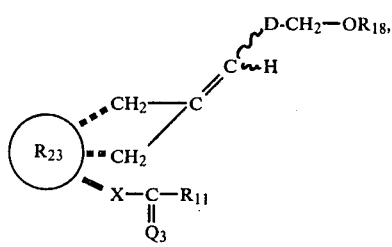

XVI (6) transforming the product of step (5) to a compound of the formula

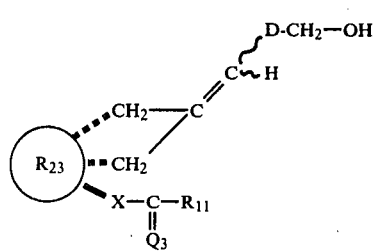

XVII (7) optionally separating the C-5 isomers of the product of step (6), (8) oxidizing the product of step (7) to form a compound of the formula

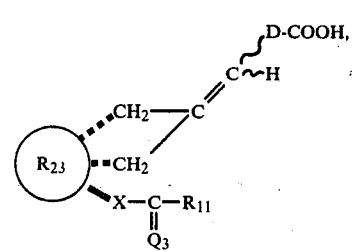

XVIII and (9) deacylating the product of step 8.

Chart A will make clear the steps of the above process, starting with the formula-X pentalen-2-one diol and forming the formula-IX 6a-carba-prostacyclin-type product.

The formula-X starting materials of Chart A are prepared by processes described hereinafter, as shown schematically in charts immediately following Chart A. One such formula-X compound is illustrated by Example 8, represented by the formula

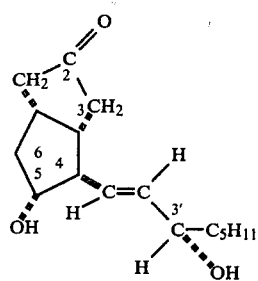

XIX and named (3aS, 6aR)-Hexahydro-5α-hydroxy-4β-(3α-hydroxy-1-transoctenyl)-pentalen-2-one. Reference to any of the pentalene structures herein will use the numbering of carbon atoms shown in Formula XIX

CHART A

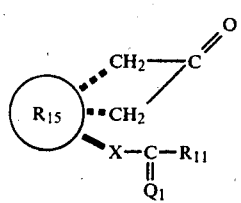

X

↓ (a)

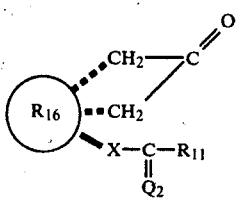

XI

↓ (b)

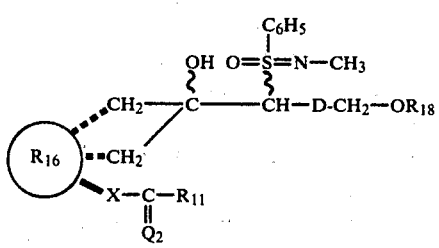

XIII

↓ (c)

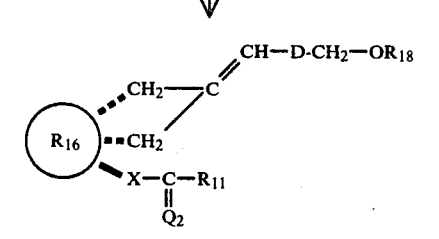

XIV

↓ (d)

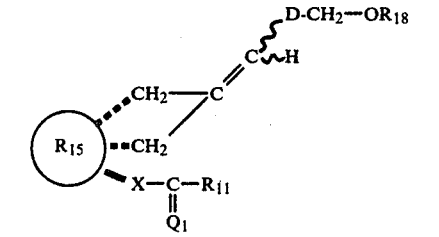

XV

↓ (e)

-continued
CHART A

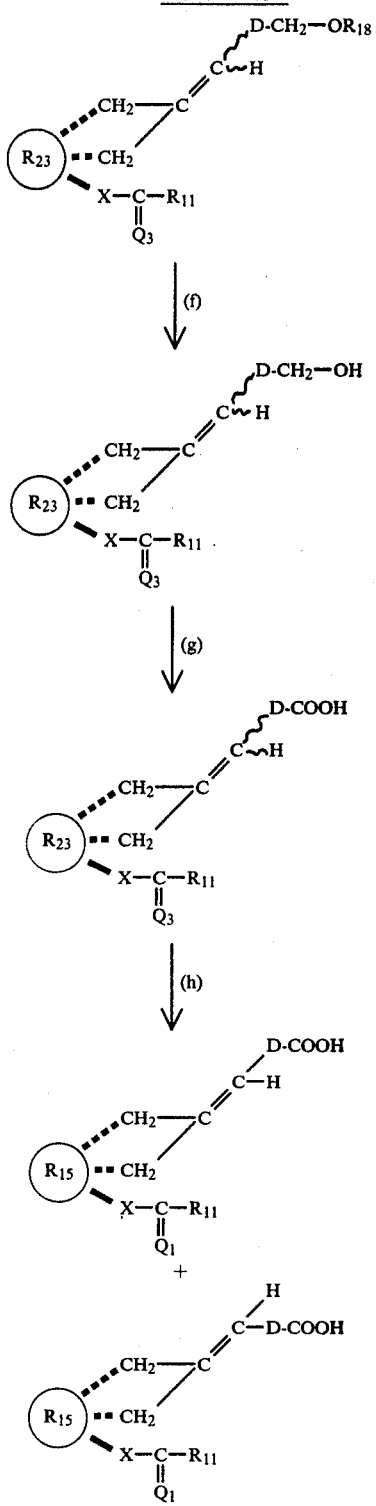

unless the upper side chain is present in which case thhe prostacyclin numbering system is used as in Formula I.

In step (a) of Chart A, the formula-X compounds are silylated with silyl blocking groups $R_{17}$, replacing hydrogen atoms on the hydroxyl groups by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds", Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane,
chlorotriisobutylsilane,
chloro(t-butyl)dimethylsilane,
chlorotriphenylsilane,
chlorotris(p-chlorophenyl)silane,
chlorotri-m-tolylsilane, and
tribenzylchlorosilane.

Alternately, a chlorosilane is used with a corresponding disilazane. Examples of other silylating agents suitable for forming the formula-XI intermediates include pentamethylsilylamine,
pentaethylsilylamine,
N-trimethylsilyldiethylamine,
1,1,1-triethyl-N,N-dimethylsilylamine,
N,N-diisopropyl-1,1,1-trimethylsilylamine,
1,1,1-tributyl-N,N-dimethylsilylamine,
N,N-dibutyl-1,1,1-trimethylsilylamine,
1-isobutyl-N,N,1,1-tetramethylsilylamine,
N-benzyl-N-ethyl-1,1,1-trimethylsilylamine,
N,N,1,1-tetramethyl-1-phenylsilylamine,
N,N-diethyl-1,1-dimethyl-1-phenylsilylamine,
N,N-diethyl-1-methyl-1,1-diphenylsilylamine,
N,N-dibutyl-1,1,1-triphenylsilylamine, and
1-methyl-N,N,1,1-tetraphenylsilylamine.

It is preferred that $R_{17}$ blocking groups be hindered silyl groups, for example, t-butyldimethylsilyl.

In step (b) the formula-XIII sulfonimidolyl adducts are obtained by addition of a carbanion of a sulfoximine. For background on this reaction see C. R. Johnson et al., J. Am. Chem. Soc. 95, 6462 (1973). Here the sulfoximine is represented by the formula

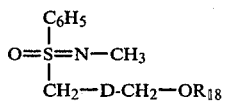     XII and is readily synthesized by methods disclosed hereinafter or known in the art. The carbanion is generated by reacting the sulfoximine with any of the usual reagents which will extract an active hydrogen from such sulfoximines, for example, an alkyllithium or an alkyl-magnesium halide. One molecular equivalent of the hydrogen-extracting reagent is used for each equivalent of sulfoximine. In the adduct formation with the formula-XI silylated ketone, the sulfoximine is preferably used in excess, in a range of 1.2 to 3.0 molecular equivalents of sulfoximine per equivalent of ketone.

The reaction is carried out in the range of about 0° C. to about −78° C., preferably 0° to −40°, in an inert reaction diluent such as tetrahydrofuran. In this reaction competing carbonyl groups on either compound XI or the solvent molecules are undesired.

In step (c) the formula-XIV intermediates are obtained by reductive elimination by contacting the formula-XIII adduct with aluminum amalgam (cf. Johnson et al., cited above) in the presence of aqueous acetic acid or other carboxylic acid such as propionic acid, butyric acid, or citric acid. Mineral acids, such as hydrochloric acid, are also useful for this purpose. The ratio of reactants is not critical, however it is preferred to use a large excess of aluminum amalgam and acid. Also, a sufficient quantity of a water-miscible inert organic liquid diluent is used to provide a mobile reaction mixture. A temperature range of about 0° C. to about 50° C., preferably about 20°–30°, is useful. The mixed C-5 (E) and (Z) isomers are obtained as a mixture.

In step (d) the $R_{17}$ silyl groups of the formula-XIV intermediates are replaced with hydrogen to yield the formula-XV compounds. For this desilylation, reagents and conditions are selected which will not deblock the C-1 ethers. For unhindered silyl groups a base such as an alkali metal carbonate in dioxane or tetrahydrofuran is useful in a temperature range of about −10° to +100° C. Preferably, the $R_{17}$ silyl groups are t-butyldimethylsilyl, in which case their removal is done with tetrabutylammonium fluoride. See Corey et al., J. Am. Chem. Soc. 94, 6190 (1972).

In step (e) the formula-XVI compounds are obtained from the formula-XV compounds above by blocking free hydroxyls with $R_{24}$ carboxyacyl groups. For example, $R_{24}$ may represent an aromatic group such as benzoyl, substituted benzoyl, mono-esterified phthaloyl, naphthoyl and substituted naphthoyl, or an aliphatic group such as acetyl or pivaloyl. For introducing those blocking groups, methods known in the art are used.

Thus, an aromatic acid of the formula $R_{24}OH$, wherein $R_{24}$ is an aromatic group within the scope of $R_{24}$ as defined above, for example benzoic acid, is reacted with the formula-XV compound in the presence of a dehydration agent, e.g. sulfuric acid, zinc chloride, or phosphoryl chloride; or an anhydride of the aromatic acid of the formula $(R_{24})_2O$, for example benzoic anhydride, is used. As examples of reagents providing $R_{24}$ for the purposes of this invention, the following are available as acids ($R_{24}OH$), anhydrides (($R_{24})_2O$), or acyl chlorides ($R_{24}Cl$): benzoyl; substituted benzoyl, e.g. (2-, 3-, or 4-) methylbenzoyl, (2-, 3-, or 4-)ethylbenzoyl, (2-, 3-, or 4-)isopropylbenzoyl, (2-, 3-, or 4-)tert-butyl-benzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-(toluyl, 2-, 3-, or 4-) 4-phenethylbenzoyl, 2-, 3-, or 4-nitrobenzoyl, (2,4-, 2,5-, or 3,5-)dinitrobenzoyl, 4,5-dimethyl-2-nitrobenzoyl, 2-nitro-6-phenethylbenzoyl, 3-nitro-2-phenethylbenzoyl;

isophthaloyl, e.g.

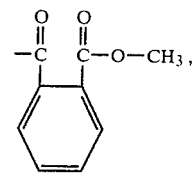

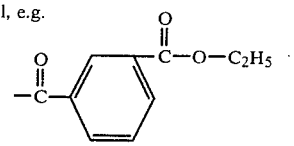

or terephthaloyl, e.g.

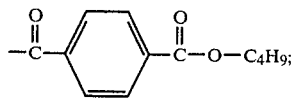

(1- or 2-)naphthoyl; and substituted naphthoyl, e.g. (2-, 3-, 4-, 5-, 6-, or 7-)-methyl-1-naphthoyl, (2- or 4-)-ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7- or 8-)-methyl-1-naphthoyl, 4-ethyl-2-napthoyl, and (5- or 8-)-nitro-2-naphthoyl.

Examples of aromatic acid anhydrides useful for this purpose are benzoic anhydride, (o, m, or p)-bromobenzoic anhydride, 2,4 (or 3,4)-dichlorobenzoic anhydride, p-trifluoromethylbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 4)-biphenylcarboxylic anhydride, 3-chloro-4-biphenylcarboxylic anhydride, 5-isopropyl-6-nitro-3-biphenylcarboxylic anhydride, and (1 or 2)-naphtholic anhydride. Preferably, however, an aromatic acyl halide, for example benzoyl chloride, is reacted with the formula-XV compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess. There may be employed, therefore, benzoyl chloride, 4-nitrobenzoyl chloride, 3,5-dinitrobenzoyl chloride, and the like, i.e. $R_{24}Cl$ compounds corresponding to the above $R_{24}$ groups. If the acyl chloride is not available, it is made from the corresponding acid and phosphorus pentachloride as is known in the art.

Aliphatic carboxyacylating agents useful for this transformation are known in the art or readily obtainable by methods known in the art, and include carboxyacyl halides, preferably chlorides, bromides, or fluorides, and carboxyacid anhydrides. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, stearic anhydride, (mono, di, or tri) chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, and phenoxyacetic anhydride.

In step (f) the formula-XVI compounds are deblocked at C-1 to yield the formula-XVII alcohols. For this purpose methods known in the art are used, for example mild acid hydrolysis for these tetrahydropyranyl or similar ether-bonded $R_{18}$ groups, using dilute acetic acid, aqueous citric acid, or aqueous phosphoric acid in a mutual solvent such as tetrahydrofuran. Temperatures in the range of 25°-55° C. may be employed.

The C-5 (E) and (Z) isomers are preferably separated at this stage, for example by chromatographing the formula-XVII compounds. For this purpose a silica gel column is useful, preferably a high pressure liquid column using silica gel with a mean particle diameter of 40 microns. For background on HPLC (high pressure liquid chromatography) see for example "Modern Practice of Liquid Chromatography", J. J. Kirkland, editor, Wiley Interscience, N.Y., 1971. Optionally the compounds of formula XIV, XV, XVI, XVIII or IX may be chromatographed to yield the respective (5E) and (5Z) isomers.

In step (g) the formula-XVIII compounds are obtained from either the now-separated (5E) and (5Z) isomers or the mixed isomers of formula XVII by oxidation. Reagents useful for this transformation are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize the hydroxy groups of the reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the formula XVIII product is isolated by conventional methods.

Finally, in step (h) the formula-IX products are obtained by deblocking the $R_{24}$ carboxyacyl groups, i.e. by decarboxyacylation, for example with a base such as potassium hydroxide or carbonate in methanol or methanol-water at about 25° C.

During the transformations of Chart A the stereoconfiguration at C-8, C-9, C-11 and C-15 is unchanged. For example, a formula-IX product with 11α-hydroxy groups is obtained from starting material X having 11-α hydroxy groups. Likewise the entire moiety represented by

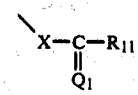

is preserved intact, so that a 15S product is obtained from a 15S starting material.

Starting with Chart B and continuing through the following seven charts, there are shown methods for preparing pentalen-2-one starting materials suitable for the process of Chart A or other processes disclosed herein.

In Chart B, the formula-XX tricyclic acetal ketone is known. See for example U.S. Patent No. 3,873,571. Especially useful is the endo compound in which $R_{27}$ and $R_{28}$ taken together are $-CH_2-C(CH_3)_2-CH_2-$, named 3-(5,5-dimethyl-1,3-dioxolan-2-yl)tricyclo[4.2.0.0$^{2,4}$]octan-7-one. Epoxidation is achieved, applying the method of E. J. Corey et al., J. Am. Chem. Soc. 87, 1353 (1965). For this purpose dimethylsulfonium

CHART B

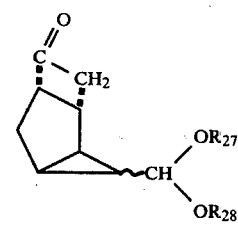

XX

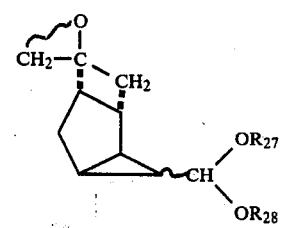

XXI

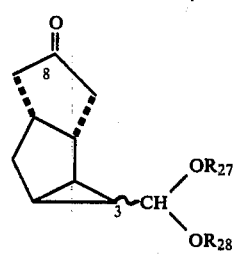

XXII

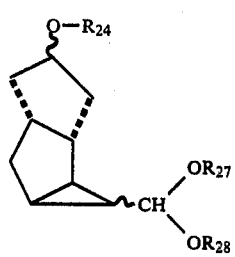

XXIII

-continued
CHART B

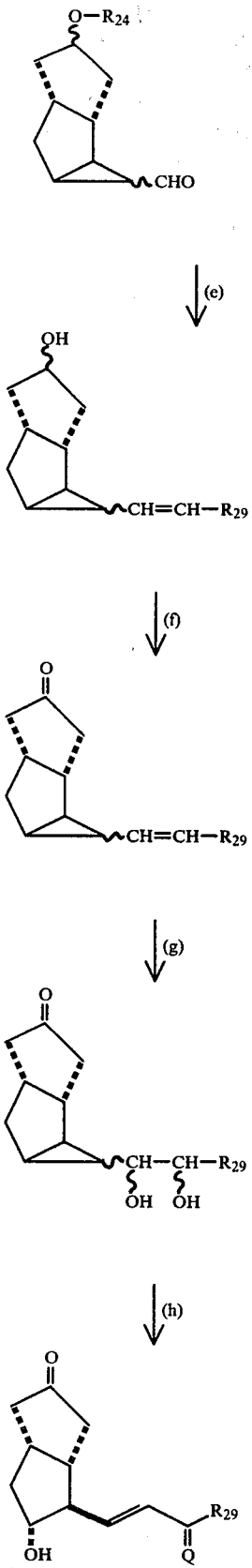

methylide is generated by reaction of sodio dimethylsulfinylcarbanide ("dimsyl") (prepared from dimethylsulfoxide and sodium hydride) and trimethylsulfonium iodide.

In step (a) the formula XXI epoxymethano compound is obtained by reaction of ketone XX with the dimethylsulfonium methylide ylid. The reaction is carried out at about 0° C. and is completed within an hour.

In step (b) the cyclopentanone structure XXII is developed following a modification of the method of M. L. Leriverend et al., C. R. Acad. Sc. Paris, Series C, 280, 791 (1975). The product of step (a) is treated with lithium iodide in a solvent such as tetrahydrofuran at room temperature. Note in formula XXII that the carbonyl position on the ring is identified as C-8 for this as well as other tricyclic structures of formulas XXIII--XXVII.

In step (c), consisting of two closely related steps, compound XXII is first reduced to the corresponding 8-hydroxy compounds, for example with a metal borohydride, especially sodium, potassium, lithium, or zinc borohydride. Other useful reducing agents are lithium(-tri-tert-butoxy)aluminum hydride, diisobutylaluminum hydride, and various borohydrides such as sodium trimethoxyborohydride. The resulting 8-hydroxy compounds, representing both $\alpha$ and $\beta$ epimers, need not be separated. The mixture is next acylated to introduce the $R_{24}$ carboxyacyl blocking groups using methods described for step (e) of Chart A, and thereby form compound XXIII.

In step (d), aldehyde XXIV is obtained from XXIII by hydrolysis of the acetal. For this purpose an acid such as aqueous formic acid is used at about 0° C.

In step (e) the Wittig reaction is employed to introduce the prospective side chain $R_{29}$. For general information on the Wittig reaction see, for example, A. W. Johnson, "Ylid Chemistry", Academic Press, N.Y., 1966. If $R_{29}$ is n-pentyl, the ylid is prepared from n-hexyltriphenylphosphonium bromide. If $R_{29}$ is pent-2-ynyl, the corresponding ylid is prepared from (hex-3-ynyl)triphenylphosphonium bromides. If $R_{29}$ is 2-phenylethyl, the corresponding ylid is prepared from (3-phenylpropyl)triphenylphosphonium bromide. The ylids are conveniently made using n-butyllithium.

Following the Wittig reaction, the $R_{24}$ acyl blocking groups are removed to form the formula-XXV compounds. Here, as for step (h) of Chart A, a base in a hydroxylic medium is useful.

In step (f) the 8-oxo formula XXVI compound is formed by oxidation. For this the Jones reagent is useful, for which see step (g) of Chart A. Another useful reagent for this purpose is the Collins reagent, e.g., chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

In step (g) alkene XXVI is hydroxylated to the glycol XXVII. For this purpose osmium tetroxide is a suitable reagent, for example in conjunction with N-methylmorpholine oxide dihydrate complex (see Fieser et al., "Reagents for Organic Synthesis" p. 690, John Wiley and Sons, Inc., New York (1967).

In step (h), several methods are available for obtaining the formula-XXVIII product. In one method, the glycol is converted to a bis(alkanesulfonic acid) ester and subsequently hydrolyzed to XXVIII by methods known in the art (see, for example German Offenlegungsschrift No. 1,937,676, Derwent Farmdoc 6862R); see also U.S. Pat. No. 3,843,712. Another method is by way of a diformate by formolysis of the glycol (see U.S. Pat. No. 3,873,571 cited above).

A preferred method is by way of a cyclic ortho ester. For this purpose, glycol XXVII is reacted with an ortho ester of the formula

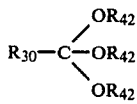

XXIX

There is then formed a cyclic ortho ester of the formula

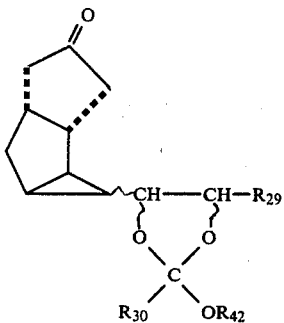

XXX

The reaction goes smoothly in a temperature range of $-50°$ C. to $+100°$ C., although for convenience $0°$ C. to $+50°$ C. is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
triethylorthoacetate,
triethyl orthopropionate,
trimethyl orthobutyrate,
triethyl orthovalerate,
trimethyl orthooctanoate,
trimethyl orthophenylacetate, and
trimethyl ortho (2,4-dichlorophenyl)acetate.
Preferred are those ortho esters wherein $R_{30}$ is alkyl of one to 7 carbon atoms; especially preferred are those wherein $R_{30}$ is alkyl of one to 4.

Next, the cyclic orthoester XXX is reacted with anhydrous formic acid to yield a diol diester of the formula

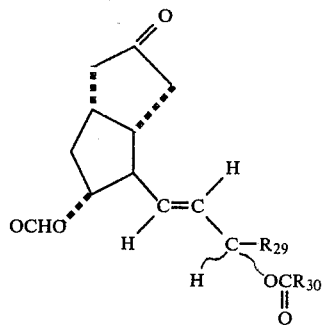

XXXI

By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about $20°-30°$ C. and is usually completed within about 10 minutes.

Finally, the diol diester XXXI is converted to product XXVIII by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to $100°$ C. The time for completion of the reaction varies with the nature of $R_{30}$ and the base, proceeding in the case of alkali carbonates in a few minutes when $R_{30}$ is hydrogen but taking up to several hours when $R_{30}$ is ethyl, for example.

The formula-XXVIII diols of Chart B are accordingly useful for preparing products within the scope of formula IX by the procedures of Chart A.

In Chart C is shown a process for preparing more pentalen-2-one intermediates within the scope of starting material X of Chart A. Attention is directed to the scope of $R_{15}$ and the hydroxy-substituted side-chain terminated by $R_{11}$.

The formula-XXXII starting materials for Chart C are available by processes described herein. See for example XXVIII of Chart B, LXXV of Chart G, and LXXXI of Chart H herein. Preferred are compounds in which $R_{29}$ is n-pentyl or straight chain alkyl for the reason that this group is sacrificed in the ozonolysis step (d).

In step (a) compound XXXIII is obtained by carboxyacylation following the procedures used for step (e) of Chart A above.

In step (b) the 2-oxo position of compound XXXIII is reduced to the 2-hydroxy of compounds XXXIV, following the procedure of step (c) of Chart B. Both the alpha and beta forms of the hydroxy are produced.

CHART C
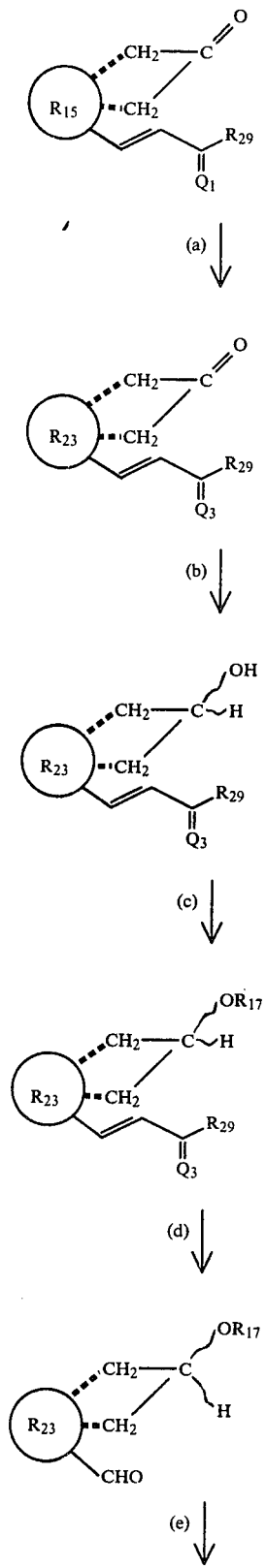
-continued
CHART C
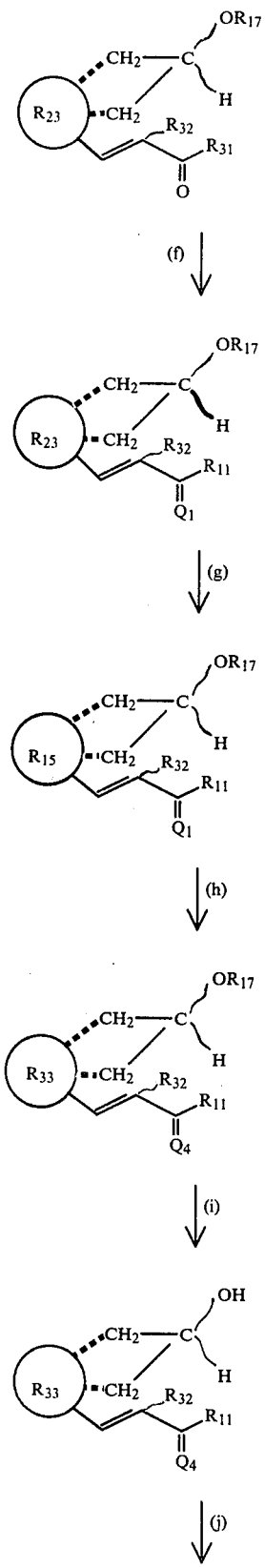

-continued
CHART C

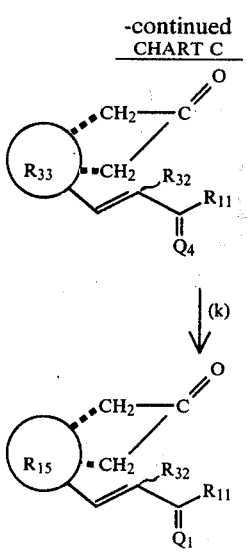

Although they may be separated this is not necessary for the production of the formula-XLVI pentalen-2-one.

In step (c) compounds XXXIV are silylated following the procedure of step (a) of Chart A, to form compounds XXXV.

In step (d) aldehydes XXXVI are obtained by ozonolysis of compounds XXXV using methods known in the art (see for example Fieser and Fieser, Reagents for Organic Synthesis, Vol. 1, pp. 773-777, John Wiley 1967).

In step (e) compounds XXXVIII are formed by Wittig alkylation of the aldehydes of step (d) using methods known in the art. See for example E. J. Corey et al., J. Am. Chem. Soc. 92, 397 (1970) and the background of the Wittig reaction for step (e) of Chart B above. See also D. H. Wadsworth et al., J. Org. Chem. 30, 680 (1965). In general the ylid is derived from a 2-oxo-alkyl (or substituted alkyl) phosphonate of the formula

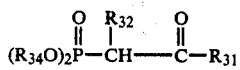   XXXIX

Examples known and used in the art are

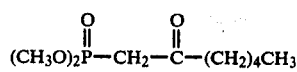

(see E. J. Corey et al., J. Am. Chem. Soc. 91, 5675 (1969))

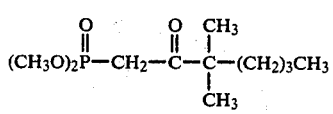

(see U.S. Pat. No. 3,954,833)

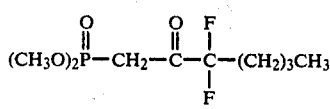

(see U.S. Pat. No. 3,962,293)

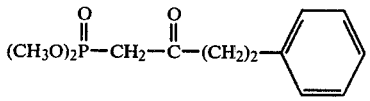   XLV (see U.S. Pat. No. 3,987,087)

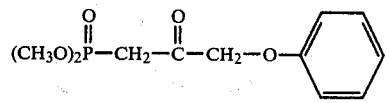   XLVI (see Brit. Pat. Specification No. 1,409,841, German Offenleg. No. 2,322,673, or Derwent Farmdoc Abstract No. 73279U). In general these and other phosphonates within the scope of reagent XXXIX are prepared by condensing the appropriate aliphatic acid esters, for example

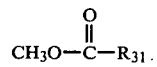

with the anion of dimethyl methylphosphonate produced by n-butyllithium. When $R_{32}$ in XXXIX is halogen, it is introduced into the phosphonate by reaction with a dilute solution of the halogen in the presence of a strong base such as sodium methoxide. See U.S. Pat. No. 4,029,681.

In step (f) the formula-XL compounds are formed by converting 3'-oxo moiety of compound XXXVIII to $Q_1$ by methods known in the art. Reduction yields a mixture of alpha and beta hydroxy isomers and for this purpose the metal borohydrides employed in step (c) of Chart B are also useful here. If 3'-methyl derivatives within the scope of $Q_1$ are desired, intermediates XXXVIII are reacted with a Grignard reagent of the formula CH$_3$MgHal. It is preferred that Hal be bromo. This reaction is carried out by the usual procedure for Grignard reactions, using diethyl ether as a reaction solvent and saturated aqueous ammonium chloride solution to hydroyze the Grignard complex. See for example U.S. Pat. No. 3,728,382.

Alternatively, for the preparation of compounds within the scope of formula XL wherein $R_{11}$ is cis-penten-2-yl, there is used an ylid derived from a hydroxy phosphonium iodide of the formula

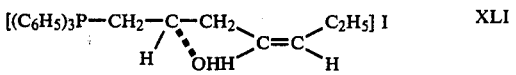   XLI

See E. J. Corey et al., J. Am. Chem. Soc. 93, 1490 (1971).

In step (g) carboxyacyl groups $R_{24}$ on compounds XL are deblocked using methods described above for step (h) of Chart A, to yield compounds XLII.

In step (h) free hydroxy groups of XLII are blocked with THP or similar $R_{18}$ groups, using methods known in the art, to yield, compounds XLIII. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C. When the blocking group is of the formula

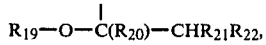

as defined above, the appropriate reagent is a vinyl ether, e.g. ethyl vinyl ether, isopropenyl methyl ether, isobutyl vinyl ether or any vinyl ether of the formula $R_{19}$—O—$C(R_{20})$=$CR_{21}R_{22}$; or an unsaturated cyclic or heterocyclic compound, e.g. 1-cyclohex-1-yl methyl ether

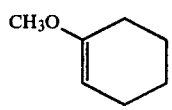

or 5,6-dihydro-4-methoxy-2H-pyran

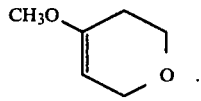

See C. B. Reese et al., J. Am. Chem. Soc. 89, 3366 (1967). The reaction conditions for such vinyl ethers and unsaturates are similar to those for dihydropyran above.

In step (i) silyl groups of compounds XLIII are deblocked in preparation for oxidation, following desilylation procedures as for step (d) of Chart A.

In step (j) the 2-hydroxy moiety of compounds XLIV is oxidized to 2-oxo. See step (f) of Chart B.

In step (k) the hydroxyls bearing THP or similar $R_{18}$ blocking groups of compounds XLV are deblocked, following procedures for step (f) of Chart A, to yield compounds XLVI.

The intermediates of Chart C in which $R_{32}$ at C-2 is halo, e.g. chloro, are useful for forming 13,14-didehydro compounds of this invention as set forth in a later chart.

Chart D shows a process for preparing 1-cis-alkenyl pentalenone intermediates LIII useful for preparing formula-V products wherein X is cis—CH=CH—. The formula-XLVII starting materials are available from formula-XXXII pentalen-2-ones by transformations described hereinafter for Chart I.

In step (a) isomerization to a cis-trans mixture is induced by irradiation with light of a wavelength between about 2800 to 4000 Angstroms. It is preferred to use a conventional photon generating source which is capable of producing photons whose wavelength is about 3500 Angstroms. Irradiation continues until an equilibrium mixture of cis and trans isomers is obtained, conveniently shown by silica gel

CHART D

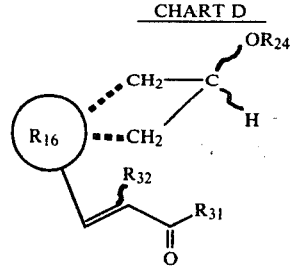

XLVII

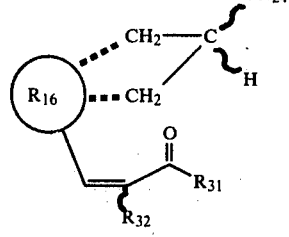

XLVIII

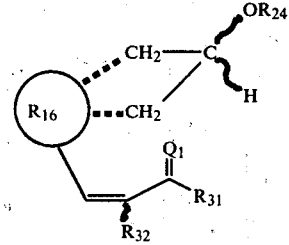

XLIX

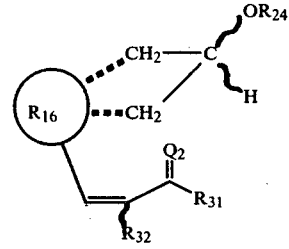

L

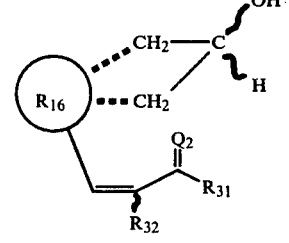

LI

CHART D -continued

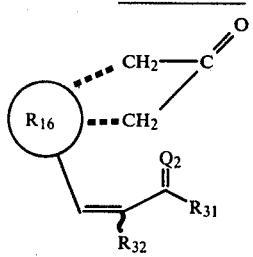 LII

↓ (f)

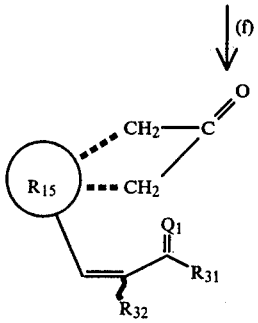 LIII

CHART E

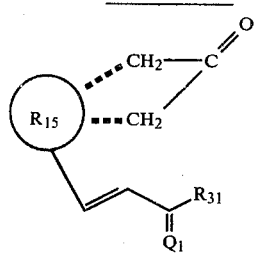 LIV

↓ (a)

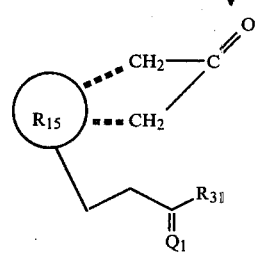 LV thin layer chromatography (TLC). See, for example, U.S. Pat. No. 4,026,909. Thereafter, the formula-XLVIII compounds with the cis configuration are separated, for example by silica gel chromatography.

In step (b) the side chain oxo moiety is reduced, following the procedures for step (f) of Chart C, to yield compounds XLIX.

In step (c) the free hydroxy group on the side chain of the formula-XLIX compounds are blocked with silyl groups. See step (a) of Chart A above.

In step (d) the C-2 position is deblocked by decarboxyacylation to yield compounds LI. See step (h) of Chart A.

In step (e) the 2-hydroxy groups are oxidized to carbonyls following the procedures of step (j) of Chart C.

In step (f) the C-5 position and the side chain hydroxyls are deblocked by desilylation to yield compounds LIII. See step (i) of Chart C.

Alternatively, the formula-XLVII starting material may be replaced with the formula-LVII compounds of Chart F wherein C-5 is blocked by THP or similar $R_{18}$ ethers. Thereafter, in step (c) the side-chain hydroxyls are also blocked with THP or similar $R_{18}$ ethers, and finally in step (f) both sites are deblocked by mild acid hydrolysis as in step (k) of Chart C.

Chart E shows a process for reducing 1-alkenyl side chains to yield formula-LV intermediates useful for preparing formula-V products wherein X is —$CH_2CH_2$—. The formula-LIV starting materials are available from Chart C, wherein $R_{32}$ is hydrogen.

In step (a) the $C_1$-$C_2$ ethylenic unsaturation is reduced catalytically with hydrogen at about one atmosphere pressure. Palladium-on-carbon or similar catalyst is useful for producing the formula-LV compounds.

Chart F shows a process for preparing 1-octynyl pentalenones of formula LXV useful for preparing formula-V products wherein X is —C≡C—. The formula-XLVII starting materials are available from other intermediates herein by transformations known in the art or described herein. See Chart I, step (e).

In step (a), the C-5 position on the ring is deblocked by desilylation, following procedures of step (i) of Chart C, to form LVI.

In step (b), the C-5 position is blocked with group $R_{18}$, for example THP, to form LVII.

In step (c) the ethylenic unsaturation in the side chain is halogenated with bromo or chloro to form LVIII, by methods known in the art. See for example U.S. Pat. No. 4,018,803. Conveniently, a reagent such as N-chlorosuccinimide is used at room temperature. The reaction proceeds slowly, ordinarily reaching completion within 3 to 10 days. Alternatively, bromine or chlorine in a diluent such as carbon tetrachloride or acetic acid-sodium acetate may be used.

In step (d), the monohalo compounds of formula LIX are formed by dehydrohalogenation by contacting the products of step (c) with an organic base such as pyridine at 80°-100° C.

In step (e), the formula-LX compounds are formed by transforming the 3'-oxo group in the side chain to $Q_1$, either by reduction or by the Grignard reagent. See step (f) of Chart C.

In step (f) the 3'-hydroxyls of LX are blocked with THP or similar $R_{18}$ groups. See (h) of Chart C.

In step (g), dehydrohalogenation yields the —C≡C— moiety, using a strong organic base such as potassium t-butoxide or sodium methoxide at about 0°-25° C.

In step (h) compounds LXII are decarboxyacylated to deblock the C-2 hydroxyls which are then oxidized in step (i). See steps (g)

CHART F
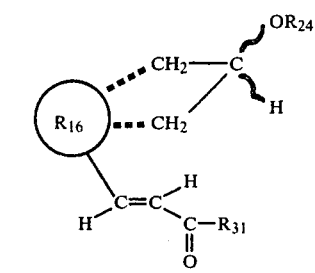 XLVII
↓ (a)
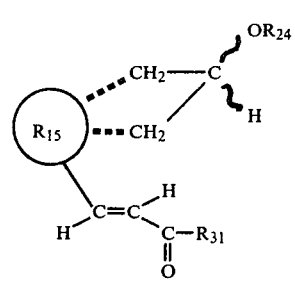 LVI
↓ (b)
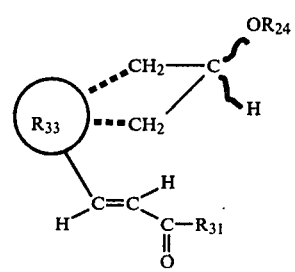 LVII
↓ (c)
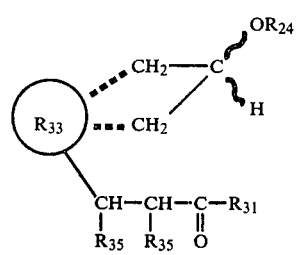 LVIII
↓ (d)
-continued
CHART F
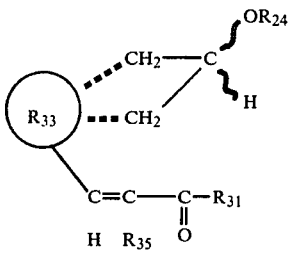 LIX
↓ (e)
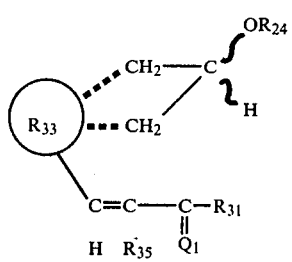 LX
↓ (f)
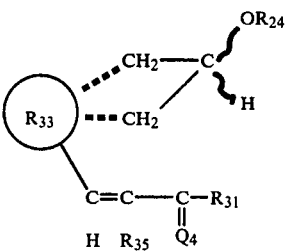 LXI
↓ (g)
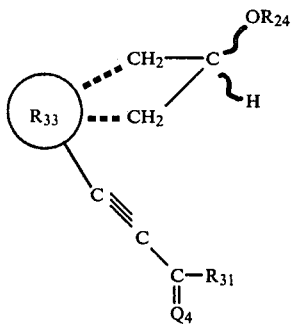 LXII
↓ (h)

-continued
CHART F

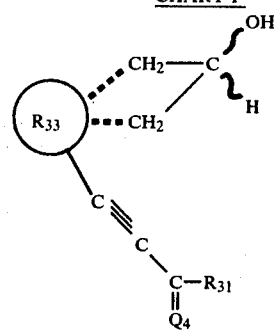
LXIII

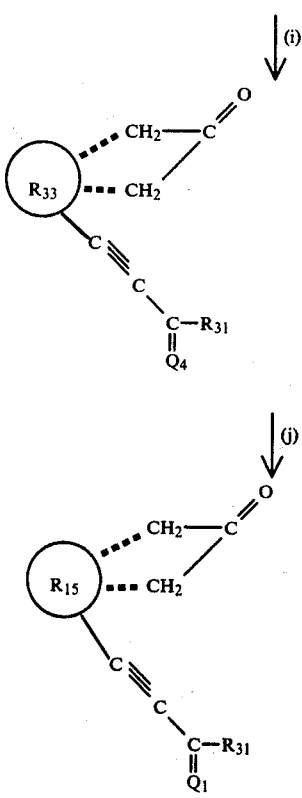
LXIV

LXV and (j) of Chart C.

In step (j) deblocking the products of step (i) in mild acid removes the THP or similar $R_{18}$ groups following the procedures of step (f) of Chart A to yield LXV.

Chart G shows a process for preparing formula-LXXV pentalen-2-ones with 5β-hydroxy, suitable as intermediates for Chart A for yielding formula-V products with 11β-hydroxy substitution. The formula-LXVI starting materials are available by processes disclosed herein. See for example XL of Chart C which is readily transformed to other compounds within the scope of the C-1',2' group "X".

In step (a) the side-chain hydroxy groups are blocked with THP or similar $R_{18}$ groups. See step (h) of Chart C.

In step (b) the C-5 hydroxyls are deblocked by decarboxylacylation. See step (h) of Chart A.

In step (c) the C-5 hydroxyls are oxidized to 5-oxo following the procedures applied to C-2 in step (f) of Chart B.

In step (d) the 5-oxo moiety is reduced, following the procedures of step (c) of Chart B. There is formed a mixture of the 5α-hydroxy and 5β-hydroxy isomers which are separated to obtain compounds of formula LXXI by step (e). For this purpose silica gel chromatography is used.

In step (f) the C-5 position is blocked by THP or similar $R_{18}$ blocking groups. See step (h) of Chart C.

In step (g) the C-2 position is deblocked by desilylation to yield LXXIII. See step (d) of Chart A.

In step (h), the 2-oxo group is formed by oxidizing LXXIII following procedures of step (c) to yield LXXIV.

Finally in step (i) compound LXXIV is deblocked as in step (f) of Chart A to yield LXXV.

Chart H shows the steps in preparing 5-deoxy pentalen-2-ones

CHART G

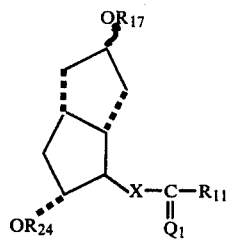
LXVI

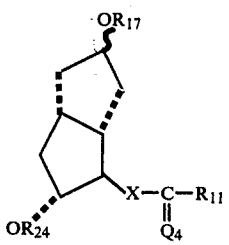
LXVII

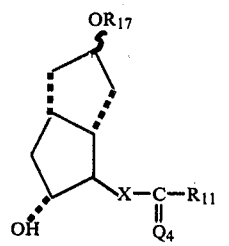
LXVIII

-continued
CHART G
LXIX
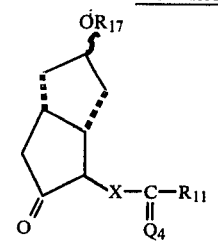
↓(d)
LXX
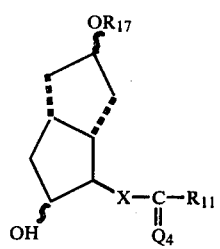
↓(e)
LXXI
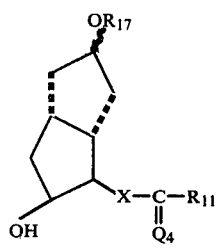
↓(f)
LXXII
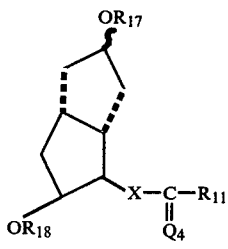
↓(g)
LXXIII
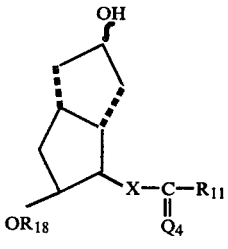
↓(h)
-continued
CHART G
LXXIV
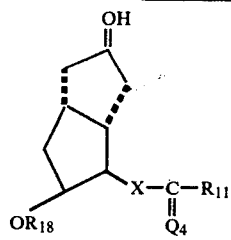
↓(i)
LXXV
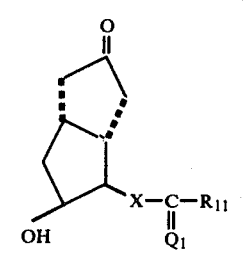
CHART H
LXXVI
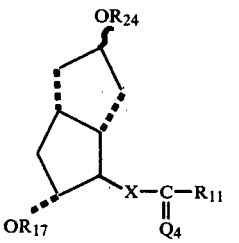
↓(a)
LXXVII
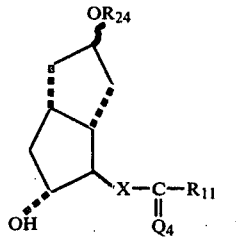
↓(b)
LXXVIII
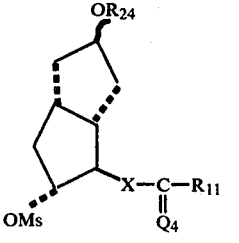
↓(c)

-continued
CHART H

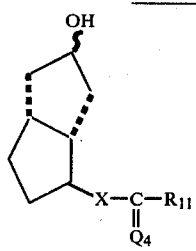
LXXIX

(d)

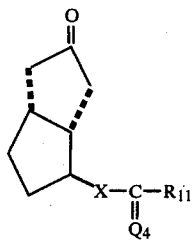
LXXX (e)

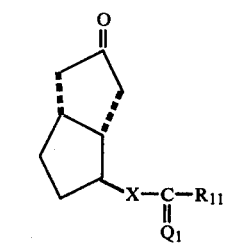
LXXXI useful as intermediates in preparing 11-deoxy prostacyclin analogs within the scope of formula V. The starting materials of formula-LXXVI are available by processes disclosed herein. See for example Chart I hereinafter.

In step (a), the C-5 position is deblocked by desilylation. See step (d) of Chart A.

In step (b), product LXXVII of step (a) is mesylated to form the 5-mesylate of formula LXXVIII. Methanesulfonyl chloride, $CH_3SO_2Cl$, is preferred for this reaction, in the presence of a base such as pyridine, dimethylaniline, or other tertiary amine. The reaction is carried out at about 0° to 25° C. Alternatively, tosyl (p-toluenesulfonyl) groups may be used and applied as known in the art. See U.S. Pat. No. 4,033,989, column 135.

In step (c), the mesylate (or tosylate) group is cleaved by methods known in the art. Reducing agents may be used, including metal borohydrides (such as sodium borohydride) metal cyanoborohydrides (such as sodium cyanoborohydride) or an aluminum hydride (such as sodium aluminum hydride) in an aprotic solvent (such as dimethyl sulfoxide or diethyl ether). For other methods see U.S. Pat. No. 4,033,989, column 79. The C-2 position is deblocked in this step.

In step (d), the formula-LXXX pentalen-2-one is obtained on oxidation, following the procedure of step (f) of Chart B.

Finally in step (e) the side-chain is deblocked as in step (f) of Chart A to yield the formula-LXXXI compounds.

Chart I shows a process which is analogous to that of Chart C but utilizes a different arrangement of blocking groups. Here, for example, silyl groups are at the C-5 position instead of the carboxyacyl and THP or similar $R_{18}$ groups in Chart C. Some of the intermediates are accordingly useful as starting materials for other

CHART I

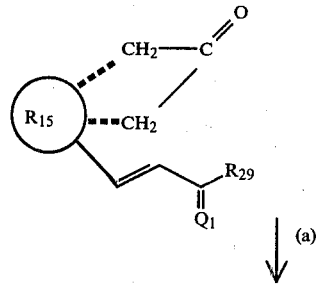
XXXII (a)

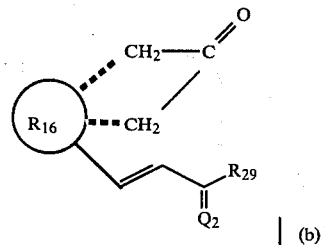
LXXXII (b)

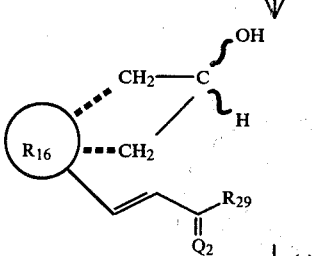
LXXXIII (c)

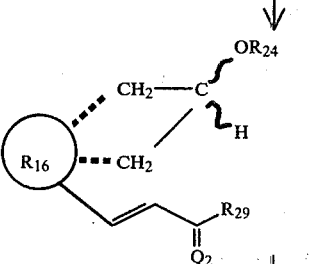
LXXXIV (d)

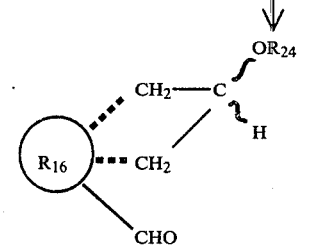
LXXXV (e)

-continued
CHART I

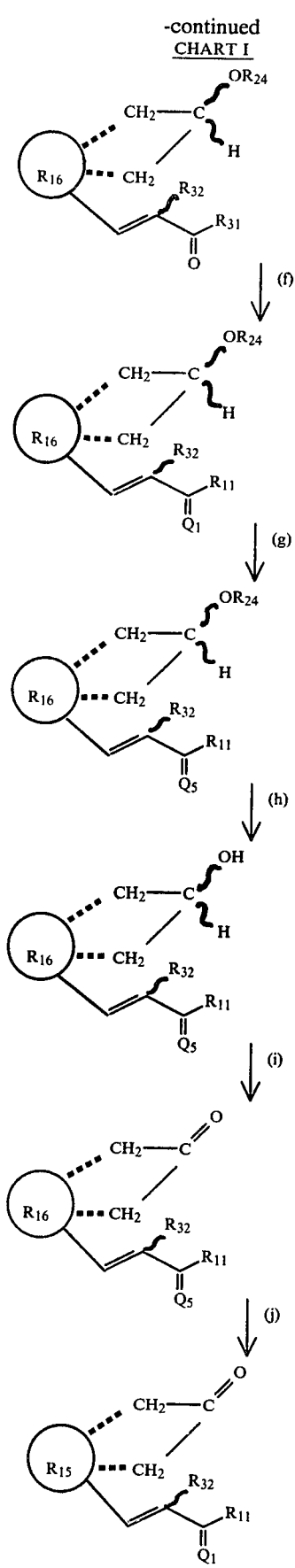

Charts, for example D or F. The formula-XXXII starting materials for Chart I are available herein, as for Chart C.

In step (a) the C-5 and C-3' positions are blocked with silyl groups, $R_{17}$, following procedures of step (a) of Chart A, to yield LXXXII.

In step (b), the C-2 oxo group is reduced. See step (c) of Chart B.

In step (c), the C-2 hydroxyls are blocked with carboxyacyl groups $R_{24}$. See step (e) of Chart A.

In step (d), aldehydes LXXXV are obtained by ozonolysis. See step (d) of Chart C.

In step (e) and (f), compounds XLVII are formed by Wittig alkylation followed by reduction. See steps (e) and (f) of Chart C. Here, as in Chart C, a Grignard reaction will lead to 3'-methyl compounds within the scope of LXXXVI. Furthermore, the Corey chemistry described above following step (f) of Chart C will yield the $R_{11}$ cis-penten-1-yl compounds.

In step (g), the 3'-hydroxyls are blocked with either $R_{17}$ silyl or $R_{18}$ THP or similar groups, following procedures given above.

In step (h), the C-2 position is deblocked by decarboxyacylation and in step (i) the resulting C-2 hydroxyls are oxidized to yield the C-2 oxo compounds of formula LXXXIX.

Finally in step (j) the C-5 and C-3' positions are deblocked to yield XLVI.

Chart J shows a process yielding 11-beta prostacyclin analogs within the scope of formula V. The 11-oxo (11-dehydro) starting materials (XC) are available herein, see step (e) of Chart L below.

In step (a), the C-1 acid groups are esterified with $R_{37}$ alkyl groups by methods known or disclosed herein. Preferred is methyl, for ease in removal at step (f). For preparing methyl esters,

CHART J

CHART J -continued

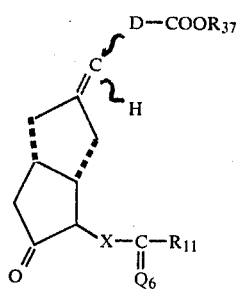

XCII

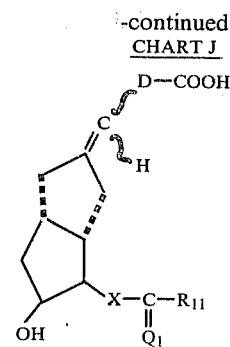

(c)

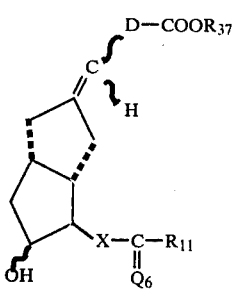

XCIII (d)

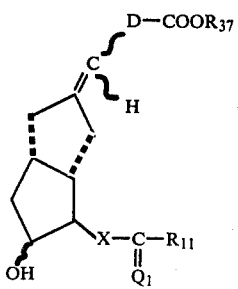

XCIV (e)

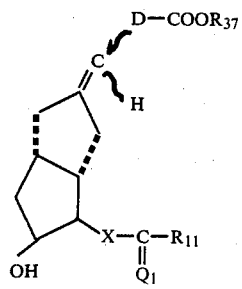

XCV (f)

-continued
CHART J

XCVI diazomethane is useful.

In step (b), the C-15 hydroxyls are blocked with any of the blocking groups within the scope of $R_{38}$ described herein, including silyl $R_{17}$ groups, THP or similar $R_{18}$ groups, and carboxyacyl $R_{24}$ groups.

In step (c), the C-5 oxo group is reduced, for example by the procedures for step (c) of Chart B, to yield XCIII.

In step (d), the C-15 hydroxyls are deblocked by any appropriate procedure described herein. See Chart A, steps (d), (f), and (h).

In step (e), the desired 11β isomers are separated, for example by silica gel chromatography.

In step (f), the formula-XCVI acids are obtained by deesterification for example by saponification in aqueous sodium or potassium hydroxide at room temperature. A mutual solvent such as methanol may be present to insure a homogenous system.

Chart K shows a process which is analogous to that of Chart A but utilizes different blocking groups. Here, for example, the silyl groups are on the sulfoximine and hence the C-1 positions instead of THP or similar $R_{18}$ groups. The starting materials of formula X are the same as for Chart A.

In step (a), the C-5 and C-3' positions are blocked with THP or similar $R_{18}$ blocking groups. See step (h) of Chart C.

In step (b), product XCVII of step (a) is reacted with the carbanion of a sulfoximine of the formula

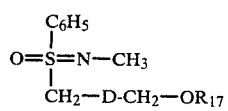

XXXVII following the procedures of step (b) of Chart A to yield sulfoximine

CHART K

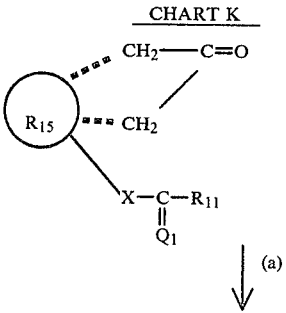

X (a)

-continued
CHART K

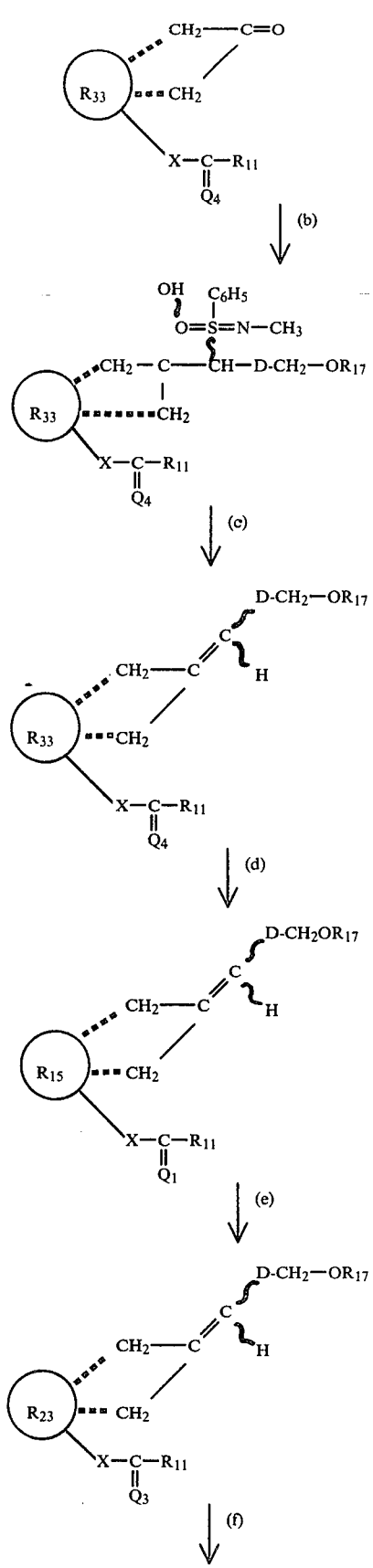

-continued
CHART K

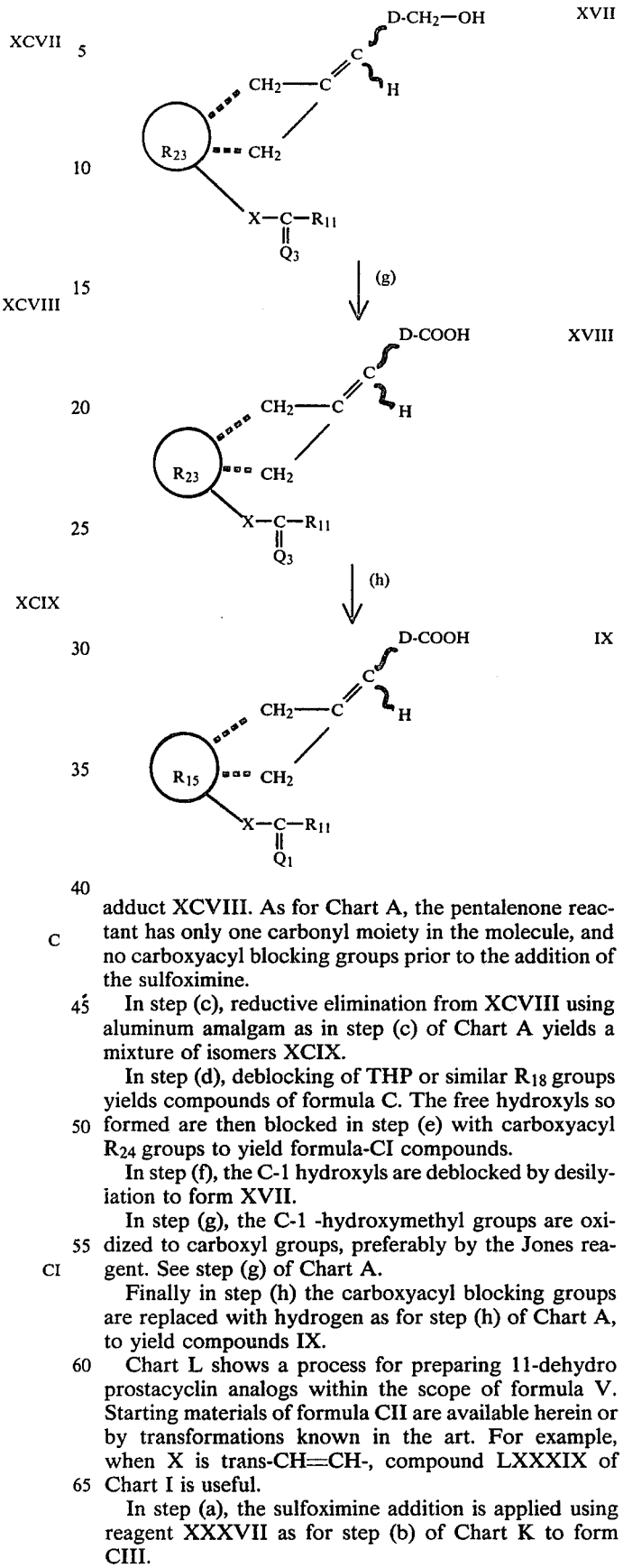

adduct XCVIII. As for Chart A, the pentalenone reactant has only one carbonyl moiety in the molecule, and no carboxyacyl blocking groups prior to the addition of the sulfoximine.

In step (c), reductive elimination from XCVIII using aluminum amalgam as in step (c) of Chart A yields a mixture of isomers XCIX.

In step (d), deblocking of THP or similar $R_{18}$ groups yields compounds of formula C. The free hydroxyls so formed are then blocked in step (e) with carboxyacyl $R_{24}$ groups to yield formula-CI compounds.

In step (f), the C-1 hydroxyls are deblocked by desilyiation to form XVII.

In step (g), the C-1 -hydroxymethyl groups are oxidized to carboxyl groups, preferably by the Jones reagent. See step (g) of Chart A.

Finally in step (h) the carboxyacyl blocking groups are replaced with hydrogen as for step (h) of Chart A, to yield compounds IX.

Chart L shows a process for preparing 11-dehydro prostacyclin analogs within the scope of formula V. Starting materials of formula CII are available herein or by transformations known in the art. For example, when X is trans-CH=CH-, compound LXXXIX of Chart I is useful.

In step (a), the sulfoximine addition is applied using reagent XXXVII as for step (b) of Chart K to form CIII.

In step (b) reductive elimination yields a mixture of isomers CIV. See step (c) of Chart K.

In step (c) the C-1 and C-11 hydroxyls are deblocked by desilylation and in step (d) they are oxidized, as by Jones reagent. See step (g) of Chart A.

Finally in step (e) the C-15 position is deblocked, replacing THP or similar $R_{18}$ groups as in step (f) of Chart A to form the CVII compounds.

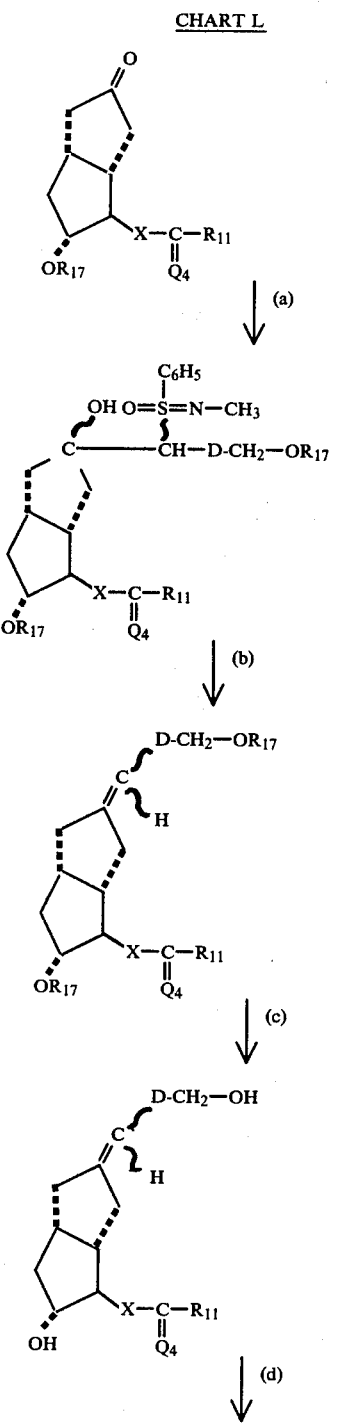

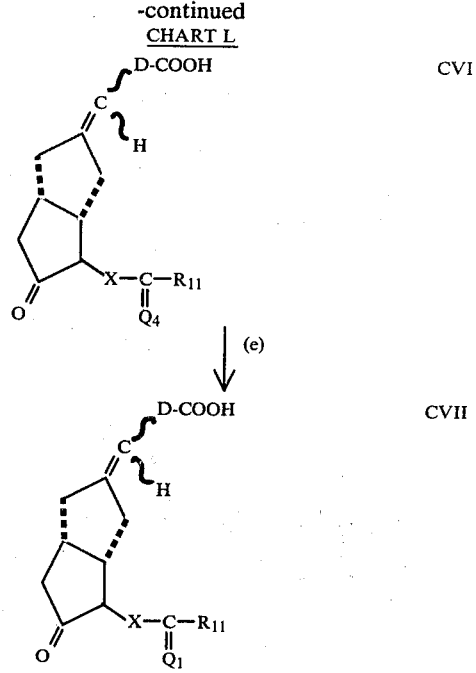

Chart M shows a process for preparing 15-methyl prostacyclin analogs within the scope of formula V. See U.S. Pat. No. 3,728,382. The starting materials for formula CVIII are available herein. For ease in separating the CXII C-15 isomers it is preferred that $R_{39}$ be methyl.

In step (a) the 15-oxo compounds of formula CIX are prepared by oxidation with reagents such as 2,3-dichloro-5,6-dicyano-1,4-benzoquinone (DDQ), activated manganese dioxide, or nickel peroxide.

In step (b) the C-11 position is blocked with silyl, and, when $R_{39}$ is hydrogen, the -COOH moiety is simultaneously transformed to $-COOR_{17}$. When $R_{39}$ is methyl, $R_{40}$ of CX is also methyl.

In step (c) the Grignard reaction is used to form the 15-methyl CXI compounds. The conventional procedure is used with $CH_3MgHal$, see U.S. Pat. No. 3,728,382 cited above. Following hydrolysis of the Grignard complex in saturated ammonium chloride solution, the products are desilylated and separated into respective (15S) and (15R) isomers by silica gel chromatography, thereby yielding the CXII products.

Chart N shows a route to the tetrazolyl derivatives within the scope of formula V. The starting materials are available herein, suitably blocked with either silyl or THP or similar $R_{18}$ groups.

In step (a) the amide of formula CXIV is prepared. Preferably a mixed anhydride is first prepared, as by using isobutyl chloroformate in the presence of a tertiary amine. Thereafter reaction with anhydrous ammonia, either gaseous or dissolved in an inert solvent such as acetonitrile, yields the amide.

In step (b) the formula-CXV nitrile is prepared from the product of step (a) by dehydration with a carbodiimide. See C. Ressler et al., J. Org. Chem. 26, 3356 (1961). For example, N,N'-dicyclohexylcarbodiimide (DCC) is useful in pyridine at about room temperature.

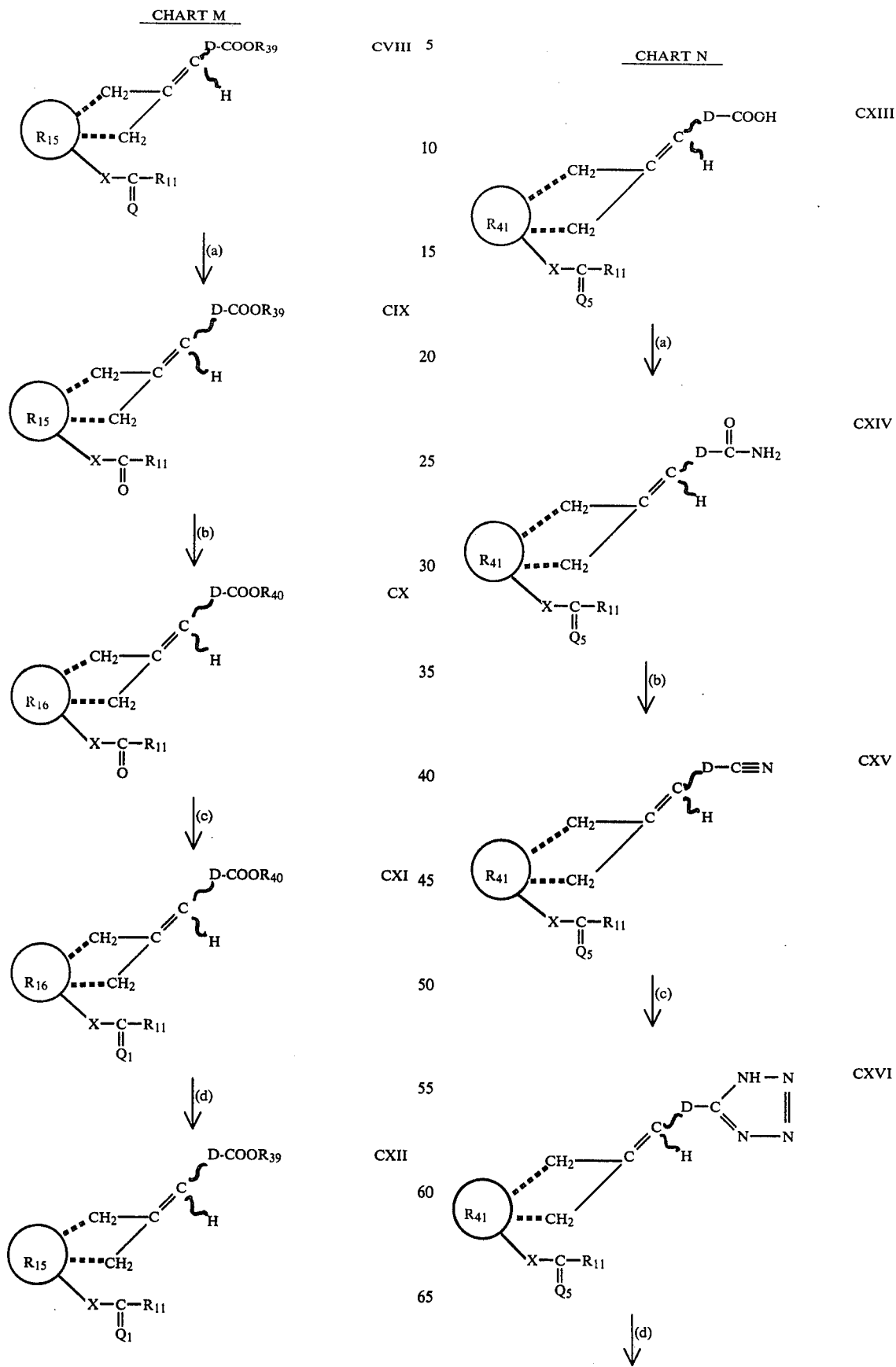

-continued
CHART N

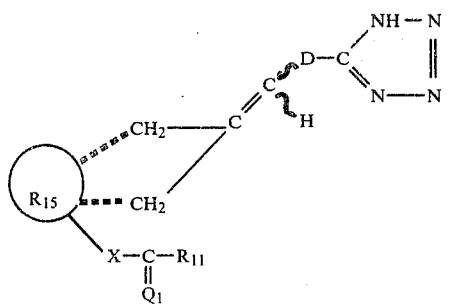
CXVII

In step (c) the tetrazolyl group in CXVI is formed from the above nitrile by reaction with sodium zide and ammonium chloride in a medium such as dimethylformamide. See "Heterocyclic Compounds", R. C. Elderfield, ed., John Wiley and Sons, Inc., N.Y., Vol. 8, pages 11–12.

Finally in step (d) the blocking groups are replaced either by desilylation or by mild acid hydrolysis as known in the art.

Chart 0 shows a process for preparing $\Delta^2$-prostacyclin analogs CXXI within the scope of formula V. The starting materials of formula CXVIII are available herein, suitably blocked with THP or similar $R_{18}$ groups. For background in preparing $\Delta^2$-prostaglandin analogs by an analogous method, see for example U.S. Pat. No. 4,024,174.

In step (a) compounds CXVIII are transformed first to 2-lithium derivatives, for example by reaction with a lithium amide formed from a secondary amine such as N-isopropylcyclohexylamine. It is preferred that that reaction be done at a low temperature, as in a Dry Ice bath. Thereafter the formula-CXIX compounds are obtained by reaction with diphenyldiselenide or benzeneselenyl bromide using about 3 equivalents for each molecular equivalent of the C-2 lithium derivative. Here again the preferred temperature is about −78° C.

In step (b) the formula-CXX $\Delta^2$ compounds are formed by oxidative elimination. Hydrogen peroxide or sodium periodate are useful.

Finally in step (c) the $R_{18}$ blocking groups are replaced, as by mild acid hydrolysis, to yield the CXXI products.

Chart P shows an alternate process for formula-IX products. In general the yields are lower by this process than by others disclosed herein but it may be convenient to use depending upon the availability of starting materials and reagents.

CHART O

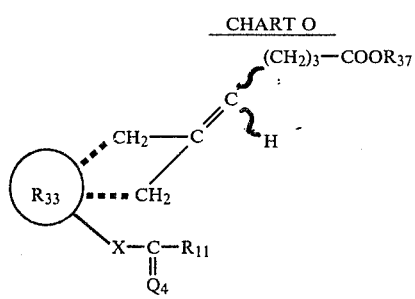
CXVIII

↓(a)

-continued
CHART O

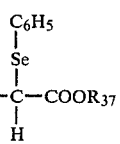
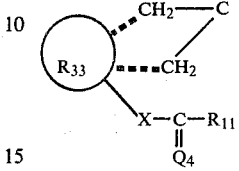
CXIX

↓(b)

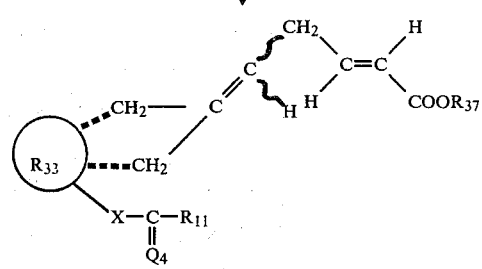
CXX

↓(c)

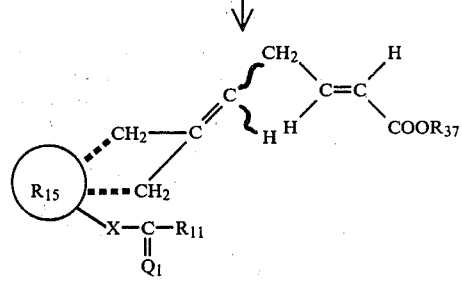
CXXI

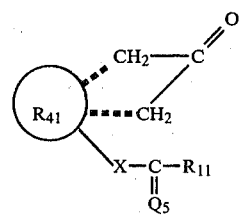
CXX

↓(a)

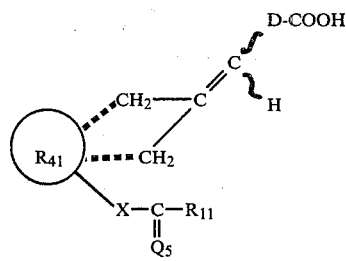
CXXII

↓(b)

-continued
CHART O

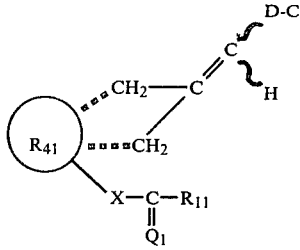

IX

In step (a) the formula-CXX starting pentalen-2-ones are reacted by the Wittig reaction with a ylid of an appropriate phosphonium compound for example

[(C$_6$H$_5$)$_3$P-CH$_2$-D-COOH]Br.    CXXI

For background on the preparation and use of this reagent see for example E. J. Corey et al., J. Am. Chem. Soc. 91, 5675 (1969).

In step (b) the blocking groups on product CXXII of step (a) are replaced to yield IX.

The process of Chart P also provides an alternate route to other formula-V compounds, for example the tetrazolyl derivatives by suitable Wittig reagents. See for example U.S. Pat. No. 3,928,391 for the tetrazolyl alkylphosphonium halide.

Transformations from one compound to another within the scope for formula V are made by reactions described herein or known in the art.

Acids, i.e. formula-V compounds wherein $R_1$ is —COOH, are readily obtained from esters, preferably lower alkyl esters having one to 4 carbon atoms in the alkyl group, by saponification. Equivalent amounts of aqueous sodium or potassium hydroxide are used, with sufficient added methanol to obtain homogeneity.

Formula-V inorganic salts are prepared by treating the formula-V acid in water with the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula-V acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula-V acid with the stoichiometric amount of the corresponding quaternary ammonium hydroxide in water solution, followed by evaporation of the water.

Various esters of formula V within the scope of $R_3$ are optionally prepared from the corresponding acids of formula V, i.e. wherein $R_1$ is —COOH, by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazomethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389-394 (1954).

An alternative method for esterification of the carboxyl moiety of the novel compounds of formula V comprises transformations of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporation the excess ammonia at reduced pressure, and then adding the stoichiometric amount of silver nitrate.

The phenyl and substituted phenyl esters of formula V are prepared by silylating the acid to protect the hydroxy groups, for example, replacing each —OH with —O—Si—(CH$_3$)$_3$. Doing that may also change —COOH to —COO—Si—(CH$_3$)$_3$. A brief treatment of the silylated compound with water will change —COO—Si—(CH$_3$)$_3$ back to —COOH. Procedures for this silylation are known in the art and are available. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH$_3$)$_3$ are changed back to —OH by treatment with dilute acetic acid. Procedures for these transformations are known in the art.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See for example U.S. Pat. No. 3,984,454, German Offenlag. No. 2,535,693, and Derwent Farmodc No. 16828X.

Compounds in which $R_1$ is

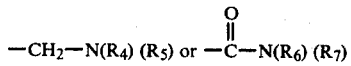

are conveniently prepared from the formula-V products which are acids, i.e. $R_1$ is —COOH. For example, the acid compound is converted to a mixed anhydride and thence to an amide. An amide may be reduced to yield an amine. Alternatively the mixed anhydride is converted to an azide, thence to a urethane from which the substituted amines, primary and secondary, are readily available by methods known in the art.

Formula-V C-1 alcohols are obtained, among other methods, by reduction of formula-V esters, by methods known in the art, for example using lithium aluminum hydride or lithium trimethoxyaluminum hydride in a solvent such as diethyl ether or tetrahydrofuran.

Formula-V compounds in which X is cis—CH=CH—, —C≡C—, or —CH₂CH₂— are prepared from intermediates in which those corresponding groups are present.

Both C-5 isomeric forms (E) and (Z) of the formula-V and other compounds disclosed herein are produced by the processes described herein. Both are useful, but the (E) forms are generally preferred because of higher biological activity. They are separated by silica gel chromatography, preferably by high pressure liquid chromatography. Once separated, the (5E) or (5Z) configuration is retained through the transformations of the compounds shown in the charts and described or exemplified herein.

DESCRIPTION OF THE PREFERRED EMBODIMENTS

The invention is further illustrated by, but not limited to, the following Examples.

All temperatures are in degrees centigrade.

Infrared absorption spectra are recorded on a Perkin-Elmer model 421 infrared spectrophotometer. Except when specified otherwise, undiluted (neat) samples are used.

The NMR (nuclear magnetic resonance) spectra are recorded on a Varian A-60, A-60D, T-60 or XL-100 spectrophotometer in deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"Celite ®" is a calcium aluminosilicate filter medium.

"Concentrating", as used herein, refers to concentration under reduced pressure, preferably at less than 50 mm. and at temperatures below 35° C.

"DDQ", refers to 2,3-dichloro-5,6-dicyano-1,4-benzoquinone.

"Drying", as used herein, refers to contacting a compound, in solution, with an anhydrous agent such as sodium sulfate or magnesium sulfate to remove water and filtering to remove solids.

"E" and "Z" follow Blackwood et al., J. Am. Chem. Soc. 90, 509 (1968).

"HPLC", herein, refers to high pressure liquid chromatography.

"Less polar" and "more polar" refer to the relative mobility of pairs of compounds, generally isomers, as shown on TLC plates or on a chromatographic column, usually on a silica gel medium.

"$R_f$" refers to the ratio of the sample spot movement to that of the solvent front, as applied in thin layer chromatography.

"Silica gel chromatography", as used herein, is understood to include elution, collection of fractions, and combination of those fractions shown by TLC to contain the desired product free of starting material and impurities.

"Skellysolve B" refers to mixed isomeric hexanes.
"THP" refers to tetrahydropyran-2-yl.
"TLC" refers to thin layer chromatography.
"TMS" refers to the trimethylsilyl group.

EXAMPLE 1

7(RS)-7-(Spiroepoxymethano)tricyclo[4.2.0.0²,⁴]octane-3-endo-carboxaldehyde Neopentyl Glycol Acetal (Formula XXI)

Refer to Chart B. A solution of 200 ml. of dimethylsulfoxide in 50 ml. of tetrahydrofuran is treated under nitrogen with sodium hydride (5.5 g. of 57% in mineral oil), then warmed to 65° C. for 1.5-2 hrs. The mixture is cooled, diluted with 100 ml. of tetrahydrofuran, and cooled in an ice bath. There is then added a solution of trimethylsulfonium iodide (E. J. Corey et al., J. Am. Chem. Soc. 87, 1353 (1965), 26.8 g.) in 135 ml. of dimethylsulfoxide over 10 min. with 10 min. additional stirring. Finally there is added a solution of the acetal ketone of formula XX, named as 3-(5,5-dimethyl-1,3-dioxolan-2-yl)tricyclo[4.2.0.0²,⁴]]octan-7-one (see U.S. Pat. No. 3,873,571, col. 27, wherein $[\alpha]_D+83°$ is reported) (15.5 g.) in 70 ml. of tetrahydrofuran. The mixture is stirred at ice bath temperature for one hr., then diluted with one liter of brine and extracted with diethyl ether. The organic phase is washed with water and brine, dried, and concentrated to an oil, 18.7 g. The oil is chromatographed on silica gel, eluting with ethyl acetate-Skellysolve B (1:4) to yield the formula-XXI epoxymethano compound, 15.1 g., having NMR absorptions at 0.70, 1.22, 0.8-3.0, 2.67, 2.70, 3.2-3.82, and 3.92δ, infrared spectral absorption at 3070, 3020, 3010, 1115, 1100, 1015, 990, 970, 945, 925, 865, 835, 790, and 785 cm⁻¹, and mass spectral lines at 249, 235, 233, 232, 219, 194, and 115.

EXAMPLE 2

8-Oxo-tricyclo[4.3.0.0²,⁴]nonane-3-endo-carboxaldehyde Neopentyl Glycol Acetal (Formula XXII)

Refer to Chart B. A solution of the formula-XXI epoxymethano compound (Example 1, 11.12 g.) in 150 ml. of tetrahydrofuran is treated with lithium iodide (2.0 g.) and stirred at about 25° C. for about one hr. The mixture is diluted with 300 ml. of brine and extracted with ethyl acetate. The organic phase is washed with brine, dried, and concentrated. The residue, a white solid, 10.79 g., is recrystallized from acetone-n-hexane to yield the title compound, 6.74 g., m.p. 98.0°-99.1° C., having NMR absorptions at 0.71, 1.22, 0.9-3.0, 3.32-3.77, and 4.31δ, infrared absorption at 3040, 1755, 1730, 1165, 1120, 1110, 1015, 990, 970, and 930 cm⁻¹, $[\alpha]_D+74°$ (c, 0.8870 in CHCl₃), mass spectral lines at 250, 222, 163, 146, 115, and 69, and $R_f$ 0.33 (TLC on silica gel in acetonitrile-methylene chloride (1:9)).

EXAMPLE 3

(8RS)-8-Acetoxy-tricyclo[4.3.0.0$^{2,4}$]nonane-3-endo-carboxaldehyde Neopentyl Glycol Acetal (Formula XXIII)

I. Refer to Chart B. There is first prepared the corresponding 8-hydroxy compound. A solution of the formula-XXII 8-oxo compound (Example 2, 12.15 g.) in 75 ml. of 95% ethyl alcohol, is added dropwise to a mixture of sodium borohydride (1.86 g.) in 200 ml. of 95% ethyl alcohol with stirring continued at about 25° C. for one hr. under nitrogen. The mixture is diluted with 400 ml. of brine and extracted with ethyl acetate. The organic phase is washed with brine, dried, and concentrated to the 8-hydroxy compound, a white solid, 11.86 g. (when recrystallized from acetone hexane, m.p. 100.0°–102.4° C.), having NMR absorptions at 0.70, 1.20, 0.9–2.6, 3.30–3.77, 4.03 and 3.9–4.3$\delta$, infrared absorption at 3480, 3440, 3280, 1110, 1075, 1010, 990, and 930 cm$^{-1}$, mass spectral peaks at 252, 234, 115, and 69, and R$_f$ 0.27 (TLC on silica gel in ethyl acetate-Skellysolve B (1:1)).

II. The product above, 11.86 g., is dissolved in 200 ml. of pyridine, cooled in an ice bath, and treated with 20 ml. of acetic anhydride and 0.2 g. of 4-(N,N-dimethylamino)-pyridine. After stirring at about 25° C. for one hr. the mixture is diluted with 400 ml. of brine and extracted with ethyl acetate. The organic phase is washed with ice-cold 1 N hydrochloric acid, saturated aqueous sodium bicarbonate, and brine, dried, and concentrated to the formula-XXIII title compound, 14.2 g., an oil having NMR absorptions at 0.72, 1.20, 0.9–2.7, 1.98, 3.23–3.8, 4.06, and 5.03$\delta$, infrared absorption at 3020, 1735, 1250, 1110, 1040, and 1020 cm$^{-1}$, mass spectral lines at 294, 234, 148, 130, and 115, and R$_f$ 0.61 (TLC on silica gel in ethyl acetate-Skellysolve B (1:1)).

EXAMPLE 4

(8RS)-8-Acetoxy-tricyclo[4.3.0.0$^{2,4}$]nonane-3-endo-carboxaldehyde (Formula XXIV)

Refer to Chart B. The formula-XXIII acetal (Example 3, 14.5 g.) is treated with 200 ml. of 88% formic acid at 0° C. for 5 hr. The mixture is then diluted with 500 ml. of brine and extracted with ethyl acetate. The organic phase is washed with water, saturated aqueous sodium bicarbonate, and brine, dried, and concentrated to an oil, 13.8 g. The oil is chromatographed on silica gel, eluting with ethyl acetate-Skellysolve B (1:4) to yield the formula-XXIV title compound, 8.80 g., an oil having NMR absorptions at 1.97, 0.9–3.1, 5.1, and 9.42$\delta$, infrared absorption at 3300, 3020, 1735, 1710, 1370, 1240, 1115, 1040, 1020, 960, and 910 cm$^{-1}$, and R$_f$ 0.28 (TLC on silica gel in ethyl acetate-Skellysolve B (1:3)).

EXAMPLE 5

(8RS)-8-Hydroxy-3-endo-(cis-1'-heptenyl)tricyclo-[4.3.0.0$^{2,4}$]nonane, less polar and more polar isomers (Formula XXV)

I. Refer to Chart B. There is first prepared the corresponding acetoxy compound. n-Hexyltriphenylphosphonium bromide (34.55 g.) in 400 ml. of toluene is treated, while cooled in an ice bath and under nitrogen, with n-butyllithium (1.4 M in hexane), first to a permanent yellow color, and then with an equivalent amount (58 ml.). The resulting bright red-orange solution is stirred at 0° C. for 30 min., then at about 25° C. for 30 min. The mixture is again cooled in an ice bath and there is added, dropwise with stirring, a solution of the formula-XXIV aldehyde (Example 4, 8.80 g.) in 50 ml. of toluene. Stirring is continued at 0° C. for one hr. Then 20 ml. of acetone is added to quench the reaction, with stirring for 20 min. The mixture is diluted with one liter of brine and extracted with ethyl acetate. The organic phase is washed with saturated aqueous sodium bicarbonate and brine, dried, and concentrated.

II. The acetyl blocking groups are next replaced with hydrogen. The residue above, a pale yellow solid, is dissolved in 200 ml. of methanol and treated with 60 ml. of 10% aqueous potassium hydroxide at about 25° C. for one hr. The reaction mixture is acidified (pH 5) with acetic acid, diluted with 500 ml. of brine, and extracted with ethyl acetate. The organic phase is washed with saturated aqueous sodium bicarbonate and brine, dried, and concentrated. The residue, a pale yellow solid, is taken up in methylene chloride and chromatographed on silica gel, eluting with ethyl acetate-Skellysolve B (1:3) to yield the mixed formula-XXV title compounds, 8.57 g., an oil having NMR absorptions at 0.7–2.5, 2.72, 3.8–4.4, and 4.8–5.75$\delta$, infrared absorption at 3300, 3020, 1460, 1120, 1065, 1045, and 965 cm$^{-1}$, and R$_f$ 0.28 and 0.33 (TLC on silica gel in ethyl acetate-Skellysolve B (1:3)).

EXAMPLE 6

8-Oxo-3-endo-(cis-1'-heptenyl)-tricyclo-[4.3.0.0$^{2,4}$]-nonane (Formula XXVI)

Refer to Chart B. A solution of the formula-XXV 8-hydroxy compounds (Example 5, 8.57 g.) in 300 ml. of acetone is treated at −30° to −20° C. with 27.4 ml. of Jones reagent (see J. Chem. Soc. 39 (1946)). Stirring is continued for 5–10 min. and then 30 ml. of isopropyl alcohol is added and stirring continued for 30 min. The mixture is diluted with one liter of brine and extracted with diethyl ether. The organic phase is washed with saturated aqueous sodium bicarbonate and brine, dried, and concentrated to an oil, 8.06 g. The oil is chromatographed on silica gel, eluting with ethyl acetate-Skellysolve B (1:3) to obtain the formula-XXVI title compound, 6.46 g., an oil having NMR absorptions at 0.7–2.9 and 5.1–5.85$\delta$, infrared absorption at 3020, 1740, 1640, and 1155 cm$^{-1}$, mass spectral lines at 232.1811, 217, 214, 204, 203, 189, and 175, and R$_f$ 0.60 (TLC on silica gel in ethyl acetate-Skellysolve B (1:3)).

EXAMPLE 7

8-Oxo-3-endo-(1,2-dihydroxyheptyl)-tricyclo-[4.3.0.0$^{2,4}$]-nonane (Formula XXVII)

Refer to Chart B. A solution of the formula-XXVI tricyclic alkene (Example 6, 0.55 g.) in 8 ml. of acetone and about one ml. of water is treated with 7.5 mg. of osmium tetroxide in 0.25 ml. of t-butanol followed by 0.38 g. of N-methylmorpholineoxide dihydrate. After stirring at about 25° C. for 1.5 hr., the reaction is complete as shown by TLC, i.e. no TLC spots attributable to starting material are observed. There is then added a solution of 0.5 g. of sodium hydrogen sulfite in 3 ml. of water, and the mixture is stirred for 0.5 hr. The mixture is diluted with brine and extracted with ethyl acetate. The organic phase is washed with brine, dried, and concentrated to give 0.70 g. The oil is chromatographed on a silica gel column, eluting with ethyl acetate (40–70%)-Skellysolve B, to yield the title compound, as a mixture of two isomers, a yellow oil, 0.61 g., having NMR absorptions at 0.92, 1.42, 2.25–2.83, 3.17, 3.40–3.83δ, infrared absorption at 3500, 3005, 3000, 2900, 1758, 1470, 1400, 1165, 1040, 935, 820, 790 and 765 cm$^{-1}$, and $R_f$ 0.24 and 0.31 (TLC on silica gel in ethyl acetate-Skellysolve B (1:3)).

EXAMPLE 8

(3aS,6aR)-Hexahydro-5α-hydroxy-4β-(3α-hydroxy-1-trans-octenyl)-pentalen-2-one (Formula XXVIII:

Q is

and the corresponding 3β-hydroxy isomer (Formula XXVIII: Q is

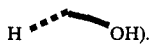

Refer to Chart B. A solution of the formula-XXVII glycol (Example 7, 6.71 g.) in 100 ml. of toluene is treated with 18.17 g. of triethyl orthopropionate and about 50 mg. of dry pyridine hydrochloride, stirring at about 25° C. for 4 hr. The mixture is then concentrated.

The residue, an oil, is dissolved in 50 ml. of 100% formic acid and stirred at about 25° C. for 10 min. The mixture is diluted with brine and extracted with ethyl acetate. The organic phase is washed with water, saturated aqueous sodium bicarbonate, and brine, dried, and concentrated. The residue, a yellow oil, 8.78 g., is dissolved in 100 ml. of methanol and treated with a solution of 7.0 g. of potassium carbonate in 10 ml. of water at about 25° C. for 16 hr. The mixture is diluted with brine and extracted with ethyl acetate. The organic phase is washed with brine, dried, and concentrated. Finally the residue is taken up in 75 ml. of methanol and treated with a solution of 1.75 g. of sodium periodate in 75 ml. of water, stirred at about 25° C. for 20 min. The mixture is diluted with brine and extracted with ethyl acetate. The organic phase is washed with brine, dried, and concentrated to an oil, 6.71 g. The oil is chromatographed on silica gel, eluting with acetone (40%)-methylene chloride to yield the 3α-hydroxy isomer of the title compounds 0.31 g., and a mixture of 3α and 3β isomers, 2.89 g. The mixture is again chromatographed, using a high pressure liquid chromatography column containing silica gel H (E. Merck, sized to a mean particle diameter of 40 microns) eluting with acetone (20%)-methylene chloride to yield the 3β-hydroxy isomer, 1.83 g. and more of the 3α-hydroxy isomer, 0.86 g. The 3β-hydroxy isomer has NMR absorptions at 0.88, 1.33, 1.83–3.00, 3.67–4.28, and 5.50–5.67δ, infrared absorption at 3450, 2950, 2900, 1735, 1165, 1135, 1090, 1070, 1025, 970, 790, and 765 cm$^{-1}$, mass spectral lines (di-TMS derivative) at 410.2659, 395, 392, 339, 320, 283, 249, 223, and 173, and $R_f$ 0.26 (TLC on silica gel in acetone-methylene chloride (3:7)). The 3α-hydroxy isomer has NMR absorptions at 0.88, 1.07–1.67, 1.83–2.83, 3.33–4.25, and 5.42–5.63δ, infrared absorption at 3400, 2950, 2900, 1740, 1165, 1130, 1095, 1075, 1025, 970, and 765 cm$^{-1}$, mass spectral lines at 410.2659, 395, 392, 339, 320, 283, 249, 223, and 173, and $R_f$ 0.16 (TLC on silica gel in acetone-methylene chloride (3:7)).

EXAMPLE 9

(3aS,6aR)-Hexahydro-5α-hydroxy-4β-(3α-hydroxy-1-trans-octenyl)-pentalen-2-one, 3,5-bis(t-butyldimethylsilyl ether) (Formula XI: $Q_2$ is

Refer to Chart A. A solution of the formula-X pentalen-2-one identified as (3aS,6aR)-hexahydro-5α-hydroxy-4β-(3α-hydroxy-1-trans-octenyl)-pentalen-2-one (Example 8, 1.18 g.) in 25 ml. of dimethylformamide is treated at 0° C. with 1.51 g. of imidazole followed by 2.0 g. of t-butyldimethylsilyl chloride, with additional stirring at 0° C. for one hr. The mixture is diluted with brine and extracted with ethyl acetate. The organic phase is washed with cold 1 N hydrochloric acid, saturated aqueous sodium bicarbonate, and brine, dried, and concentrated to an oil, 2.62 g. The oil is chromatographed on silica gel, eluting with ethyl acetate (5%)-Skellysolve B, to yield the title compound, 1.84 g., an oil having NMR absorptions at 0.03, 0.88, 1.25–1.38, 2.03–2.83, 3.95–4.22, and 5.42–5.6δ, infrared absorption at 2950, 2900, 1745, 1255, 1120, 1080, 835 and 775 cm$^{-1}$, mass spectral lines at 479.3376, 437, 423, 363, 347, 305, 291, and 251, and $R_f$ 0.44 (TLC on silica gel in ethyl acetate-Skellysolve B (1:9)).

EXAMPLE 10

N-Methyl-S-(ω-hydroxypentyl)-S-phenylsulfoximine, Tetrahydropyran-2-yl Ether (Formula XII).

Refer to C. R. Johnson et al., J. Am. Chem. Soc. 95, 6462 (1973). A solution of N,S-dimethyl-S-phenylsulfoximine (1.69 g.) in 20 ml. of tetrahydrofuran is treated at 0°–5° C. under nitrogen with 7.14 ml. (10 mmol) of n-butyllithium in n-hexane, added dropwise with stirring. After 20 min. there is added a solution of the tetrahydropyran-2-yl ether of 5-bromobutanol (3.56 g.) in 5 ml. of tetrahydrofuran, and 10 ml. of hexamethylphosphoramide. The mixture is stirred at about 25° C. for 14 hr., then at 50° C. for 4 hr. The mixture is cooled to room temperature, diluted with brine and extracted with diethyl ether. The organic phase is washed with brine, dried, and concentrated to an oil, 6.02 g. The oil is chromatographed on silica gel, eluting with ethyl acetate (75–100%)-Skellysolve B, to yield the title compound, 1.75 g., an oil having NMR absorptions at 1.25–2.08, 4.30, 3.00–4.00, 4.50, and 7.43–8.00δ, infrared absorption at 3060, 2940, 2870, 1445, 1240, 1140, 1115, 1075, 1033, 1020, 865, 748, 735, and 690 cm$^{-1}$, mass spectral lines at 325, 296, 240.1043, 224, 210, 182, 125, 85, and 77, and $R_f$ 0.19 (TLC on silica gel in ethyl acetate-Skellysolve B (1:1)).

EXAMPLE 11

6a-Carba-2-decarboxy-2-hydroxymethyl-6ξ-hydroxy-5ξ-(N-methylphenylsulfonimidoyl)-PGI$_1$, 1-(tetrahydropyranyl ether), 11,15-bis(t-butyldimethylsilyl ether) (Formula XIII).

Refer to Chart A. A solution of the formula XII sulfoximine (Example 10, 1.22 g.) in 10 ml. of tetrahydrofuran is treated at 0°–5° C. under nitrogen with n-butyllithium (2.68 ml. of 1.40 M in n-hexane) added dropwise with stirring. The mixture is stirred an additional 30 min. and cooled to −15° C. There is then added dropwise a solution of the formula-XI pentalen-2-one, 3,5-bis(silyl ether) (Example 9, 1.23 g.) in 7 ml. of tetrahydrofuran, and the mixture is stirred at −10° C. to 20° C. for 2 hr. There is added 10 ml. of saturated aqueous ammonium chloride and brine, and the mixture extracted with ethyl acetate. The organic phase is dried and concentrated to an oil, 0.72 g. The oil is chromatographed on silica gel, eluting with ethyl acetate (10-15%)-Skellysolve B, to yield the title compound, 0.81 g., as well as recovered formula-XI starting material, 0.56 g. The product has infrared absorption at 3300, 2950, 2850, 1460, 1240, 1115, 1075, 1030, 1000, 970, 905, 865, 835, 813, 775, 715 and 690 cm$^{-1}$, $R_f$ 0.09-0.11 (TLC on silica gel in ethyl acetate-Skellysolve B (1:9)), and $R_f$ 0.26-0.36 (TLC on silica gel in acetone-methylene chloride (3:97)).

EXAMPLE 12

(5E and Z)-6a-Carba-2-decarboxy-2-hydroxymethyl-PGI$_2$, 1-(tetrahydropyran-2-yl ether), 11,15-bis(t-butyldimethylsilyl ether) (Formula XIV).

Refer to Chart A. A solution of the formula-XIII sulfonimidoyl compound (Example 11, 1.25 g.) in 15 ml. of tetrahydrofuran is treated with aluminum amalgam (prepared from 0.61 g. of aluminum, 20 mesh, washed with water, ethanol, and diethyl ether, contacted with 2% aqueous mercuric chloride for 30 sec., and washed with diethyl ether) together with 3.9 ml. of water and 3.9 ml. of acetic acid. The mixture is stirred at 15°-20° C. for 2.5 hr., then filtered through Celite ® (a calcium aluminosilicate filter medium). The filter cake is washed with ethyl acetate. The organic phase is washed with brine, saturated aqueous sodium bicarbonate, and brine, dried, and concentrated to an oil, 1.28 g. The oil is chromatographed on silica gel, eluting with ethyl acetate (3-5%)-Skellysolve B, to yield the title compound, 0.73 g., an oil having NMR absorptions at 0.05, 0.88, 0.91, 1.17-1.83, 1.85-2.42, 3.20-4.27, 4.60, and 5.08-5.67δ, infrared absorption at 2940, 2860, 1460, 1250, 1115, 1075, 1030, 970, 835, and 775 cm$^{-1}$ $R_f$ 0.30 (TLC on silica gel in ethyl acetate-Skellysolve B (3:97)), and $R_f$ 0.74 (TLC on silica gel in acetone-methylene chloride (3:97)).

EXAMPLE 13

6a-Carba-2-decarboxy-2-hydroxymethyl-PGI$_2$, 11,15-di-acetate, less polar (5Z)-isomer and more polar (5E)-isomer (Formula XVII).

I. Refer to Chart A. There is first prepared the corresponding 1-(tetrahydropyran-2-yl ether) diol without silyl groups at C-11 and C-15. A solution of the formula-XIV 6a-carba-2-decarboxy-2-hydroxymethyl-PGI$_2$, 1-(tetrahydropyran-2-yl ether), 11,15-bis(t-butyldimethylsilyl ether) (Example 12, 0.73 g.) in 5 ml of tetrahydrofuran is treated with 9 ml. of a solution of tetrabutylammonium fluoride (0.5 M in tetrahydrofuran). The mixture is stirred at 20°-25° C. for 1.5 hr. and then at 40° C. for 2.5 hr. Additional tetrabutylammonium fluoride solution (4.5 ml.) is added and stirring continued at 40° C. for 1.5 hr. The mixture is cooled to room temperature, diluted with brine, and extracted with ethyl acetate. The organic phase is washed with ice-cold 1 N potassium hydrogen sulfate, saturated aqueous sodium bicarbonate, and brine, dried, and concentrated to an oil, 0.68 g.

II. The above formula-XV diol is then acetylated by reaction with 1.0 ml. of acetic anhydride in 7 ml. of pyridine stirred at about 25° C. for 16 hr. The mixture is diluted with brine and extracted with ethyl acetate. The organic phase is washed with 1 N potassium hydrogen sulfate, saturated aqueous sodium bicarbonate, and brine, dried, and concentrated to give the formula-XVI 1-(tetrahydropyran-2-yl ether), 11,15-diacetate, an oil, 0.63 g.

III. The product of part II above is then hydrolyzed in 10 ml. of a solution of acetic acid-water-tetrahydrofuran (20:10:3) together with 3 ml. of tetrahydrofuran at 40° C., with stirring for 3 hr. There is then added an additional 10 ml. of the acetic acid-water-tetrahydrofuran solution and stirring continued at 40° C. for 3 hr. The mixture is cooled to room temperature, diluted with brine, and extracted with ethyl acetate. The organic phase is washed with saturated aqueous sodium bicarbonate and brine, dried, and concentrated to an oil, 0.64 g. The oil is chromatographed on a high pressure liquid chromatographic column on silica gel H (E. Merck, sized to mean particle diameter of 40 microns), eluting with acetone (3-4%)-methylene dichloride to yield the formula-XVII title compounds, first the less polar (5Z)-isomer, 0.12 g., then a mixture of the isomers, 0.10 g., and finally the more polar (5E)-isomer, 0.15 g. The less polar (5Z)-isomer has NMR absorptions at 0.67-1.05, 1.08-1.67, 1.83, 1.98, 2.03, 2.13-2.53, 3.52-3.80, and 4.50-5.6δ, infrared absorption at 3460, 2940, 2860, 1740, 1440, 1365, 1235, 1060, 1010, and 970 cm$^{-1}$, mass spectral lines (for TMS derivative) at 432.3076, 417, 390, 372, 342, 300, and 282, and $R_f$ 0.49 (TLC on silica gel in acetonemethylene chloride (1:19)).

The fraction of mixed isomers is again chromatographed on a high pressure liquid chromatographic column, eluting with acetone (4%)-methylene chloride to yield the less polar isomer, 0.05 g. and the more polar isomer, 0.06 g. The more polar (5E)-isomer has NMR absorptions at 0.67-1.05, 1.08-1.67, 1.83, 1.98, 2.03, 2.13-2.53, 3.52-3.80, and 4.50-5.6 δ, infrared absorption at 3460, 2940, 2860, 1740, 1440, 1365, 1235, 1060, 1010, and 970 cm$^{-1}$, mass spectral lines (for TMS derivative) at 432.3063, 417, 390, 372, 342, 300, and 282, and $R_f$ 0.44 (TLC on silica gel in acetone-methylene chloride (1:19)).

EXAMPLE 14

(5Z)-6a-Carba-PGI$_2$, less polar isomer (Formula IX(Z))

I. Refer to Chart A. A solution of the formula-XVII 2-decarboxy-2-hydroxymethyl compound (Example 13, 0.17 g., less polar isomer) in 6 ml. of acetone is treated at −30° C. with 0.61 ml. of Jones reagent with stirring. After 20 min. the mixture is warmed to −10° C. and stirred for 20 min. longer. The mixture is cooled to −30° C., treated with 4 ml. of isopropyl alcohol, and slowly warmed to room temperature. The mixture is diluted with brine and extracted with ethyl acetate. The organic phase is washed with brine, dried, and concentrated to an oil, 0.20 g., consisting essentially of the 11,15-diacetate of the title compound, represented by formula XVIII.

II. The above material, in 5 ml. of methanol-water (9:1), is treated with one ml. of 5% potassium hydroxide at about 25° C. for 2 hr. The mixture is cautiously acidified with 1 M potassium hydrogen sulfate, diluted with brine and extracted with ethyl acetate. The organic phase is washed with brine, dried and concentrated to an oil, 0.126 g. The oil is chromatographed on silica gel, eluting with ethyl acetate (40%)-Skellysolve B, to yield the formula-IX(Z) title compound, 0.043 g., an oil, which solidifies on standing at −19° C. Recrystallization from acetone-n-hexane gives a colorless solid: m.p. 102°-106.6° C. The title compound has NMR absorptions at 0.67-2.58, 3.47-4.30, 5.13, and 5.42-5.57 δ, infrared absorption at 3380, 2930, 2860, 1710, 1460, 1400, 1350, 1320, 1240, 1180, 1130, 1060, 990, 970, and 860 cm$^{-1}$, mass spectral lines (for tri-TMS derivative) at 551.3398, 495, 476, 405, 386, 149, and 73, and $R_f$ 0.12 (TLC on silica gel in ethyl acetate-acetic acid-Skellysolve B (33:2:65), 3 elutions).

EXAMPLE 15

(5E)-6a-Carba-PGI$_2$, more polar isomer (Formula IX(E)).

Refer to Chart A. Following the procedure of Example 14 but replacing the formula-XVII starting material of that example with the formula-XVII 2-decarboxy-2-hydroxymethyl compound, more polar isomer (Example 13, 0.21 g.) there is obtained the title compound 0.115 g., an oil, which solidifies on standing at −19° C. Recrystallization from diethyl ether-in-hexane gives a colorless solid: m.p. 61.5°-64.1° C. The title compound has NMR absorptions at 0.67-2.67, 3.50-4.30, 5.0-5.30, and 5.37-5.90 δ, infrared absorption at 3380, 2930, 2860, 1710, 1450, 1250, 1070, 965 and 900 cm$^{-1}$, mass spectral lines (for tri-TMS derivative) at 551.3392, 495, 476, 405, 386, 149 and 73, and $R_f$ 0.09 (TLC on silica gel in ethyl acetate-acetic acid-Skellysolve B (33:2:65)).

Following the procedures of Examples 9-15 and referring the Chart A, but replacing starting material X with the pentalenone of Example 43 in which "X" is —CH$_2$CH$_2$—, there are obtained the corresponding 13,14-dihydro compounds, namely (5E)-6a-carba-13,14-dihydro-PGI$_2$ and (5Z)-6a-carba-13,14-dihydro-PGI$_2$.

Likewise following the procedures of Examples 9-15, but replacing the formula-XII sulfoximine with a compound of the formula

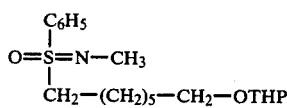

there are obtained the corresponding 2a,2b-dihomo compounds, namely (5E)-6a-carba-2a,2b-dihomo-PGI$_2$ and (5Z)-6a-carba-2a,2b-dihomo-PGI$_2$.

Again following the procedures of Examples 9-15, but using, instead, a formula-XII sulfoximine of the formula

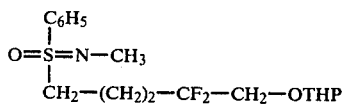

there are obtained the corresponding 2,2-difluoro compounds, namely (5E)-6a-carba-2,2-difluoro-PGI$_2$ and (5Z)-6a-carba-2,2-difluoro-PGI$_2$. Thereafter, following the procedures of Example 21-II, herein, the corresponding methyl esters are obtained.

EXAMPLE 16

(3aS,6aR)-Hexahydro-5α-hydroxy-4β-hydroxy-4β-(3β-hydroxy-1-transoctenyl)-pentalen-2-one, 3,5-bis(t-butyl-dimethylsilyl ether) (Formula XI: Q$_2$ is

Refer to Chart A. Note that the title compound is the 15-epimer of the product of Example 9. Following the procedures of Example 9, but replacing the formula-X starting material of that example with the corresponding 3β-hydroxy isomer of Example 8 (1.49 g.), there is obtained 3.30 g. crude oil which on chromatographing yields 2.46 g. of the formula-XI title compound, an oil having NMR absorptions at 0.03, 0.90, 1.15-2.88, 3.75-4.27, and 5.40-5.58 δ, infrared absorption at 2900, 2800, 1745, 1460, 1240, 1110, 1080, 1000, 960, 930, 830, and 770 cm$^{-1}$, mass spectral lines at 494, 479.3352, 451, 437, 423, 363, 347, 305, 291, and 251, and $R_f$ 0.48 (TLC on silica gel in ethyl acetate-Skellysolve B (1:9)).

EXAMPLE 17

6-a-Carba-2-decarboxy-2-hydroxymethyl-6ξ-hydroxy-5ξ-(N-methylphenylsulfonimidoyl)-(15R)-PGI, 1-(tetrahydropyranyl ether), 11,15-bis(t-butyldimethylsilyl ether) (Formula XIII).

Refer to Chart A. A solution of the formula XII sulfoximine (Example 10, 2.53 g.) in 15 ml. of tetrahydrofuran is treated at 0° C. under nitrogen with 2.7 ml. of a methylmagnesium bromide solution (2.7 M. in diethyl ether) and stirred at 0°-5° C. for 0.5 hr. The mixture is then cooled to −20° C., and stirred for 15 min. There is then added a solution of the formula-XI 3β-silyloxy compound (Example 16, 2.40 g.) in 8 ml. of tetrahydrofuran and the mixture stirred at −15° to −20° C. for 15 min. Finally there is added 8 ml. of saturated aqueous ammonium chloride at −15° C. The mixture is warmed to about 25° C., diluted with brine, and extracted with ethyl acetate. The organic phase is dried and concentrated to an oil, 4.83 g. The oil is chromatographed on silica gel, eluting with ethyl acetate (10-20%)-Skellysolve B to obtain the formula-XIII title compound, 3.12 g., an oil having infrared absorption at 3300, 2920, 2850, 1450, 1240, 1105, 1070, 1030, 1000, 965, 905, 865, 835, 813, 775, 718, and 690 cm$^{-1}$, and $R_f$ 0.11-0.15 (TLC on silica gel in ethyl acetate-Skellysolve B (1:9)).

EXAMPLE 18

(5E and Z)-6a-Carba-2-decarboxy-2-hydroxymethyl-(15R)-PGI$_2$, 1-(tetrahydropyran-2-yl ether), 11,15-bis(t-butyldimethylsilyl ether) (Formula XIV).

Refer to Chart A. Following the procedure of Example 12 but replacing the formula-XIII sulfonimidoyl compound of that example with the corresponding 3β-isomer of Example 17 (3.50 g.), there is obtained 3.05 g. crude oil. The oil is chromatographed on silica gel, eluting with ethyl acetate (3-5%)-Skellysolve B to yield the title compound, 2.08 g., an oil, having NMR and infrared absorptions essentially identical to those reported for the (15S)-isomer of the title compound (see Example 12), and $R_f$ 0.32 (TLC on silica gel in ethyl acetate-Skellysolve B (3:97)).

EXAMPLE 19

6a-Carba-2-decarboxy-2-hydroxymethyl-(15R)-PGI$_2$, 11,15-diacetate, less polar (5Z)-isomer and more polar (5E)-isomer (Formula XVII).

I. Refer to Chart A. There is first prepared the formula-XV 1-(tetrahydropyran-2-yl ether) diol from formula XIV by deblocking silyl groups R$_{17}$ at C-11 and C-15. A solution of the formula-XIV 6a-carba-2-decarboxy-2-hydroxymethyl-(15R)-PGI$_2$, 1-(tetrahydropyran-2-yl ether), 11,15-bis(t-butyldimethylsilyl ether) (Example 18, 2.08 g.) in 25 ml. of tetrahydrofuran is treated with 20.7 ml. of a solution of tetrabutylammonium fluoride (0.62 M. in tetrahydrofuran) at about 25° C. for 16 hr. Additional tetrabutylammonium fluoride (20.7 ml.) is added and stirring continued at 40° C. for 4 hr. The mixture is cooled, diluted with brine, and extracted with ethyl acetate. The organic phase is washed with ice-cold 0.5 M. potassium hydrogen sulfate, saturated aqueous sodium bicarbonate, and brine, dried, and concentrated to an oil, 2.09 g.

II. The above formula-XV diol is then acetylated in 20 ml. of pyridine using 5 ml. of acetic anhydride at 25° C. for 16 hr. The mixture is diluted with brine and extracted with ethyl acetate. The organic phase is washed with ice-cold 1 N hydrochloric acid, saturated aqueous sodium bicarbonate, and brine, dried, and concentrated to give the formula-XVI 1-(tetrahydropyran-2-ether), 11,15-diacetate, an oil, 1.96 g.

III. The product of part II above, dissolved in 5 ml. of tetrahydrofuran, is hydrolyzed in 20 ml. of acetic acid-water-tetrahydrofuran (20:10:3), stirring at 40° C. for 26 hr. The mixture is cooled to room temperature, diluted with brine, and extracted with ethyl acetate. The organic phase is washed with saturated aqueous sodium bicarbonate and brine, dried, and concentrated to an oil, 1.70 g. The oil is chromatographed on silica gel to yield the formula-XVII mixed isomers, 1.09 g. total.

The mixture of isomers is separated on a high pressure liquid chromatographic column on silica gel 60 (E. Merck, 230-400 mesh) eluting with ethyl acetate (35%)-n-hexane, to yield (A) less polar (5Z)-isomer, an oil, 0.09 g., and (B) a mixture of both isomers. The mixture is again chromatographed, using two size B (E. Merck) prepacked columns in series, eluting with ethyl acetate (25%)-n-hexane, to yield (C) less polar (5Z)-isomer, 0.26 g., (D) a mixture, 0.15 g. and (E) more polar (5E)-isomer, 0.53 g. Fraction D is again chromatographed in the same way, yielding (F) less polar (5Z)-isomer, 0.04 g. and (G) more polar (5E)-isomer, 0.10 g. Total of less polar (5Z)-isomer, 0.39 g., total of more polar (5E)-isomer, 0.63 g. The less polar (5Z)-isomer has R$_f$ 0.54 (TLC on silica gel in ethyl acetate in Skellysolve B (1:1)) and the more polar (5E)-isomer has R$_f$ 0.50 (TLC on silica gel in ethyl acetate in Skellysolve B (1:1)).

EXAMPLE 20

(5Z)-6a-Carba-(15R)-PGI$_2$, less polar isomer (Formula IX(Z)).

Refer to Chart A: Following the procedure of Example 14 above but replacing the formula-XVII compound of that example with the corresponding less polar 15R compound of Example 19, there is first obtained by oxidation the formula-XVIII 11,15-diacetate of the title compound, 0.43 g.

The above material is saponified, again following the procedure of Example 14, to yield the title compound, crude oil 0.318 g. The oil is chromatographed on silica gel, eluting with ethyl acetate (35%)-Skellysolve B, to yield the title compound, 0.206 g., an oil having NMR absorptions at 0.87, 0.92-2.72, 3.48-4.13, 5.42, 5.07-5.47, and 5.50-5.68 δ, infrared absorption at 3400, 2940, 2860, 1710, 1450, 1370, 1250, 1080, 1050, and 970 cm$^{-1}$, mass spectral lines (for tri-TMS derivative) at 566, 551.3420, 495, 476, 461, 405, 386, 379, 360, 199, 173, and 117, and R$_f$ 0.20 (TLC on silica gel in ethyl acetate-acetic acid-Skellysolve B (33:2:65), 3-elutions).

EXAMPLE 21

(5E)-6a-Carba-(15R)-PGI$_2$, more polar isomer (Formula JX(E)).

I. Refer to Chart A. Again following the procedure of Example 14 above but replacing the formula-XVII starting material of that example with the formula-XVII more polar (5E)-isomer (Example 19, 0.63 g.) and first oxidizing and then saponifying, there is obtained principally the title compound, 0.257 g., an oil.

II. This material is further purified as its methyl ester. Accordingly, a solution of the above oil (0.257 g.) in 5 ml. of acetonitrile is treated with 0.4 ml. of methyl iodide and 0.26 ml. of diisopropylethylamine at about 25° C. for 16 hr. The mixture is diluted with brine and acidified (pH 1) with 0.5 M aqueous potassium hydrogen sulfate. The solution is extracted with ethyl acetate and the organic phase is washed with brine, saturated aqueous sodium bicarbonate, and brine, dried, and concentrated to an oil, 0.229 g. The oil is chromatographed on a high pressure liquid chromatographic column (silica gel, E. Merck, size B prepacked), eluting with acetone (15%)-methylene chloride, to yield the methyl ester of the title compound, 0.133 g., an oil.

III. The above methyl ester (0.133 g.) is saponified to the title compound acid in 7 ml. of a solution of 5% potassium hydroxide in methanol-water (9:1) stirred at about 25° C. for 2 hr. There is then added 2 ml. more or reagent and stirring continued for 16 hr. The mixture is diluted with brine, cautiously acidified (pH 1) with 0.5 M potassium hydrogen sulfate, and extracted with ethyl acetate. The organic phase is washed with brine, dried, and concentrated to the title compound, 0.130 g., an oil having NMR absorptions at 0.90, 0.93-2.58, 1.85-4.28, 5.13, and 5.55-5.70 β, infrared absorption at 3400, 2950, 1710, 1450, 1240, 1070, 970, and 900 cm$^{-1}$, mass spectral lines (for the tri-TMS derivative) at 566, 551.3423, 495, 476, 461, 405, 386, 379, 360, 199, 173, and 117, and R$_f$ 0.16 (TLC on silica gel in ethyl acetate-acetic acid-Skellysolve B (33:2:65)).

EXAMPLE 22

(5E)-6a-Carba-PGI$_2$, Sodium Salt.

A solution of (5E)-6a-carba-PGI$_2$ (Example 15, 0.28 g.) in methanol is neutralized with a solution of sodium carbonate in water at about 25° C. The mixture is concentrated to a small volume, diluted with acetonitrile and concentrated again to yield the title compound as a white solid.

EXAMPLE 23

(5E)-6a-Carba-PGI$_2$, Methyl Ester and (5Z)-6a-Cara-PGI$_2$, Methyl Ester (Formula V).

Following the procedure of Example 21-II, (5E)-6a-carba-PGI$_2$ (Example 15) and (5Z)-6-a-carba-PGI$_2$ (Example 14) are transformed to the title compounds using methyl iodide and diisopropylethylamine in acetonitrile.

Alternatively, the methyl esters are prepared by separate reaction of each acid in methanol with diazomethane at about 25° C. for 5 min. Each mixture is concentrated to give the corresponding title compound.

EXAMPLE 24

(5E)-6a-Carba-PGI$_2$, p-Phenylphenacyl Ester (Formula V).

A mixture of (5E)-6a-carba-PGI$_2$ (Example 15, 0.2 g.), p-phenylphenacyl bromide (0.50 g.), 0.4 ml. of diisopropylethylamine, and 10 ml. of acetonitile is stirred at about 25° C. for 40 min. It is then mixed with dilute aqueous citric acid and brine and extracted with ethyl acetate. The organic phase is dried and concentrated. The residue is chromatographed on silica gel, eluting with ethyl acetate (25–100%)-Skellysolve B to yield the title compound.

EXAMPLE 25

(5E)-6a-Carba-PGI$_2$, Amide (Formula V).

Refer to Chart N. A solution of (5E)-6a-carba-PGI$_2$ (Example 15, 1.0 g.) in 10 ml. of acetone is cooled to about −10° C. and treated with 0.44 ml. of triethylamine and 0.41 ml. of isobutyl chloroformate. After 5 min. there is added 10 ml. of acetonitrile saturated with anhydrous ammonia, and the reaction mixture is warmed to about 25° C. The mixture is filtered and the filtrate is concentrated. The residue is taken up in ethyl acetate, washed with water, aqueous potassium bisulfate, brine, dried, and concentrated. The residue is chromatographed, eluting with acetone (25–100%)-methylene chloride to yield the title compound.

EXAMPLE 26

(5E)-6a-Carba-PGI$_2$, N-(Methylsulfonyl)amide (Formula V).

A solution of (5E)-6a-carba-PGI$_2$ (Example 15, 1.0 g.) in 6 ml. of dimethylformamide is cooled to about 0° C. and treated with 0.44 ml. of triethylamine and 0.41 ml. of isobutyl chloroformate. After 25 min. there is added 1.54 g. of methanesulfonamide, sodium salt (prepared from 3.0 ml. of 4.4 N methanolic sodium methoxide added to a solution of 1.36 g. of methanesulfonamide in 6 ml. of methanol and recovered by concentrating in the presence of benzene) and 1.25 ml. of hexamethylphosphoramide. The mixture is stirred at about 25° C. for 16 hr., acidified with cold dilute hydrochloric acid, and extracted with ethyl acetate. The organic phase is washed with water and brine, dried, and concentrated. The residue is chromatographed on silica gel, eluting with methanol (10–20%)-methylene chloride, to yield the title compound.

EXAMPLE 27

(5E)-6a-Carba-2-decarboxy-2-aminomethyl-PGI$_2$ (Formula V).

A solution of the formula-V (5E)-6a-carba-PGI$_2$, amide (Example 25, 0.1 g.) in 1 ml. of tetrahydrofuran is treated with a solution of lithium aluminum hydride (100 mg.) in 5 ml. of tetrahydrofuran at about 25° C. for 2 days. Thereafter the mixture is cooled in an ice bath, treated successively with 0.1 ml. of water, 0.1 ml. of 15% sodium hydroxide and 0.3 ml. of water, and filtered. The solids are rinsed with ethyl acetate and the combined filtrates are dried and concentrated to yield the title compound.

EXAMPLE 27

(5E)-6a-Carba-2-decarboxy-2-aminomethyl-PGI$_2$ (Formula V)

A solution of the formula-V (5E)-6a-carba-PGI$_2$, amide (Example 25, 0.1 g.) in 1 ml. of tetrahydrofuran is treated with a solution of lithium aluminum hydride (100 mg.) in 5 ml. of tetrahydrofuran at about 25° C. for 2 days. Thereafter the mixture is cooled in an ice bath, treated successively with 0.1 ml. of water, 0.1 ml. of 15% sodium hydroxide and 0.3 ml. of water, and filtered. The solids are rinsed with ethyl acetate and the combined filtrates are dried and concentrated to yield the title compound.

EXAMPLE 28

(5E)-6a-Carba-2-decarboxy-2-(1H-tetrazol-5-yl)-PGI$_2$ (Formula V).

I. Refer to Chart N. A solution of (5E)-6a-carba-PGI$_2$ (Example 15, 1.0 g.) in 10 ml. of methylene chloride is treated with dihydropyran (2 ml.) in the presence of pyridine hydrochloride (10 mg.) at about 25° C. for 6 hr. The reaction mixture is washed with aqueous potassium bicarbonate solution, dried, and concentrated to the bis(THP) ether, THP ester. The THP ester is then transformed to the formula-CXIII bis(THP) ether by saponification with potassium hydroxide in aqueous methanol.

II. Following the procedures of Example 25, the formula-CXIV amide is prepared by reaction of ammonia with the mixed anhydride.

III. The formula-CXV nitrile is prepared from the amide of II by reaction with N,N'-dicyclohexylcarbodiimide (DCC) in pyridine at about 25° C. The precipitated dicyclohexylurea is removed by filtration and the filtrate is concentrated to the formula-CXV nitrile.

IV. The formula-CXVI tetrazolyl compound is obtained from the nitrile of III by reaction with sodium azide and ammonium chloride in dimethylformamide at about 115° C. When the reaction is finished as shown by TLC, the mixture is cooled and concentrated. The residue is taken up in chloroform, washed with brine, dried, and concentrated to the formula-CXVI compound.

V. The product of IV is deblocked by contact with acetic acid-water-tetrahydrofuran (10;5:2) at about 40° C. for 4 hr. The mixture is concentrated and the residue is chromatographed on silica gel to yield the formula-CXVII title compound.

EXAMPLE 29

(5E)-6a-Carba-$\Delta^2$-PGI$_2$, Methyl Ester (Formula CXXI).

I. Refer to Chart 0. The formula-CXIX 2-phenyl selenidyl compound is first prepared. The starting material is the methyl ester of (5E)-6a-carba-PGI$_2$ (Example 23, 0.4 g.) which is converted to the formula-CXVIII bis(tetrahydropyran-2-yl ether) by reaction with dihydropyran in methylene chloride in the presence of pyridine hydrochloride following the procedure of Example 39-II. A solution of that bis(THP) methyl ester in 5 ml. of tetrahydrofuran is added dropwise to the amide formed from N-isopropylcyclohexylamine (0.3 g.) and n-butyllithium (equivalent 1.6 M hexane solution) in tetrahydrofuran (7 ml.) cooled to −78° C. The mixture is stirred at −78° C. for 45 min. and then phenylselenyl chloride is added in tetrahydrofuran solution over a 7 minute period. The mixture is stirred at −78° C. for an additional hour, then poured into 30 ml. of saturated ammonium chloride-ice-water mixture and extracted with diethyl ether. The organic phase is dried and concentrated. The residue is chromatographed on silica gel, eluting with ethyl acetate-toluene (1:8) to give the formula-CXIX compound.

II. The formula-CXX $\Delta^2$ compound is formed by oxidative elimination. The product of I, in methylene chloride, is treated with 10% hydrogen peroxide at about 25° C., stirring vigorously for one hr. The organic phase is washed with 5% sodium bicarbonate, saturated sodium bicarbonate, and brine, dried, and concentrated to yield the formula-CXX compound.

III. The title compound is obtained on deblocking the product of II using acetic acid-water-tetrahydrofuran (20;10:3) at 40° C.

EXAMPLE 30

(5E)-6a-Carba-(15S)-15-methyl-PGI$_2$ and (5E)-6a-Carba(15R)-15-methyl-PGI$_2$ (Formula V).

I. Refer to Chart M. A solution of (5E)-6a-carba-PGI$_2$, methyl ester (Example 23, 1.0 g.) in 30 ml. of dioxane is treated with 2,3-dichloro-5,6-dicyano-1,4-benzoquinone (DDQ) (0.8 g.) and the reaction mixture is stirred at 25° C. for 72 hr. The mixture is filtered and the filtrate is concentrated and chromatographed on silica gel, eluting with ethyl acetate (25–50%)-Skellysolve B to yield the formula-CIX (5E)-6a-carba-15-oxo-PGI$_2$, methyl ester.

II. There is next prepared the formula-CX trimethyl silyl derivative, by treating the product of I, in tetrahydrofuran solution, with hexamethyldisilazane (22 ml.) and trimethylchlorosilane (5 ml.) at about 25° C. for 18 hr. The mixture is concentrated to yield the silylated intermediate.

III. The product of II is treated, in diethyl ether solution at −78° C. to −40° C., with 3 M ethereal methylmagnesium bromide (1.5 ml.). When TLC on a sample confirms that no ketone remains, the mixture is warmed to room temperature, quenched by pouring into saturated aqueous ammonium chloride and ice, and extracted with diethyl ether. The organic phase is washed with brine, dried, and concentrated. The residue, containing the formula-CXI compounds, is taken up in ethanol (45 ml.), diluted with ether (30 ml.), and stirred at about 25° C. for 4 hr. The organic solvent is removed under reduced pressure and the aqueous residue is saturated with sodium chloride and extracted with ethyl acetate. The organic phase is washed with brine, dried, and concentrated to give a mixture of the methyl esters of the title compounds. The methyl esters of the title compounds are separated by chromatography on silica gel. The respective acids are obtained following saponification, for example with 5% potassium hydroxide in methanol-water (9:1) at about 25° C. as in Example 21-III.

Following the procedures of Example 30 but replacing the starting material of that example with each of the following compounds or their methyl esters
(5E) or (5Z)-6a-carba-13,14-dihydro-PGI$_2$
(5E) or (5Z)-6a-carba-2-decarboxy-2-hydroxymethyl-PGI$_2$
(5E) or (5Z)-6a-carba-2a,2b-dihomo-PGI$_2$
(5E) or (5Z)-6a-carba-2,2-difluoro-PGI$_2$
there are obtained the corresponding (15S)-15-methyl and (15R)-15-methyl compounds, either as methyl esters or free acids.

EXAMPLE 31

(5Z)-6a-Carba-(15S)-15-methyl-PGI$_2$ and (5Z)-6a-Carba-(15R)-15-methyl-PGI$_2$ (Formula V)

Following the procedures of Example 30 but replacing the starting material of that example with the corresponding (5Z) compound (Example 23) there are obtained the title compounds.

EXAMPLE 32

(5E)-6a-Carba-2-decarboxy-2-hydroxymethyl-PGI$_2$ and (5Z)-6a-Carba-2-decarboxy-2-hydroxymethyl-PGI$_2$ (Formula V).

Refer to Chart A. The formula-XVII 6-a-carba-2-decarboxy-2-hydroxymethyl-PGI$_2$, 11,15-diacetate 5E and 5Z isomers of Example 13-III are treated separately with one ml. of 5% potassium hydroxide in 5 ml. of methanol-water (9:1) at about 25° C. for 2 hr. to remove acetyl groups. Thereafter each mixture is cautiously acidified with 1 M potassium hydrogen sulfate, diluted with brine, and extracted with ethyl acetate. The organic phases are washed with brine, dried and concentrated to yield the respective title compounds.

EXAMPLE 33

(5E)-6a-Carba-PGI$_3$ and (5Z)-6a-Carba-PGI$_3$ (Formula V)

Refer to Charts B and A. There is first prepared the formula-XXVIII pentalen-2-one, namely (3aS,6aR)-hexahydro-5α-hydroxy-4β-(3α-hydroxy-1-trans-5-cis-octadienyl)-pentalen-2-one.

I. The formula-XXIV aldehyde, namely (8 RS)-8-acetoxy-tricyclo-[4.3.0.0$^{2,4}$]nonane-3-endo-carboxaldehyde (Example 4) is reacted with the Wittig ylid of the triphenyl phosphonium salt of 1-bromohex-3-yne (U.F. Axen et al., Chem. Comm. 1970, 602), following the procedures of Example 5-I. Thereafter the acetyl groups are replaced with hydrogen by the procedures of Example 5-II to yield the formula-XXV compounds.

II. The product of I is oxidized with Jones reagent, following the procedure of Example 6, to yield the formula-XXVI ketone.

III. The formula-XXVII glycol is obtained by the procedure of Example 7. The —C≡C— moiety is then reduced to cis—CH=CH— by hydrogenation over 5% palladium-on-barium sulfate in the presence of synthetic quinoline, terminating the reaction when one equivalent of hydrogen is absorbed. See Fieser and Fieser, Reagents for Organic Synthesis, Vol. 1, page 566, John Wiley, N.Y., 1967.

IV. The formula-XVIII pentalen-2-ones are obtained by the procedures of Example 8, finally separating the 3α-hydroxy isomer from the 3β-isomer.

The title compounds are obtained following the procedures of Chart A and Examples 9-14.

EXAMPLE 34

(3aS,6aR)-Hexahydro-5α-benzoyloxy-4β-(3α-benzoyloxy-1-trans-octenyl)-pentalen-2-one (Formula XXXIII).

Refer to Chart C. A solution of the formula-XXXII pentalen-2-one identified as (3aS,6aR)-hexahydro-5α-hydroxy-4β-(3α-hydroxy-1-transoctenyl)-pentalen- 2-one (Example 8, 2.0 g.) in 100 ml. of pyridine is treated with 3.4 ml. of benzoyl chloride at 25° C. for 16 hr. The mixture is cooled to 0° C. and treated with 6 ml. of 85% lactic acid at 0° C. for 5 min. and at 25° C. for 15 min. The mixture is diluted with brine and extracted with ethyl acetate. The organic phase is washed with ice-cold 1 N hydrochloric acid, saturated aqueous sodium bicarbonate, and brine, dried, and concentrated to yield the title compound, an oil, 3.76 g.

EXAMPLE 35

(3aS,6aR)-Hexahydro-5α-benzoyloxy-4β-(3α-benzoyloxy-1-trans-octenyl)-2-(α or β)-(t-butyldimethylsiloxy)-pentalene (Formula XXXV).

I. Refer to Chart C. There are first prepared the formula-XXXIV corresponding 2α and 2β hydroxy compounds. A solution of the formula-XXXIII pentalen-2-one (Example 34, 2.37 g.) in 5 ml. of methanol is added to a mixture of sodium borohydride (0.38 g.) in 40 ml. of methanol and 10 ml. of water at −20° C. to −10° C. with vigorous stirring for one hr. There is then added (cautiously) one ml. of glacial acetic acid to quench the reaction, followed by brine. The mixture is extracted with ethyl acetate and the organic phase is washed with saturated aqueous sodium bicarbonate and brine, dried, and concentrated to yield the formula-XXXIV 2-hydroxy compounds.

II. The product of I above, in 10 ml. of dimethylformamide, is treated with 1.50 g. of t-butyldimethylsilyl chloride and 1.36 g. of imidazol. The reaction mixture is stirred at about 25° C. for 24 hr., then diluted with brine and extracted with ethyl acetate. The organic phase is washed with ice-cold 0.1 N. hydrochloric acid, saturated aqueous sodium bicarbonate, and brine, dried and concentrated. The residue is chromatographed over silica gel, eluting with ethyl acetate (5–50%)-Skellysolve B to yield the formula-XXXV title compounds.

EXAMPLE 36

(3aS,6aR)-Hexahydro-5α-benzoyloxy-2(α or β)-(t-butyldimethylsiloxy)-4β-pentalenecarboxaldehyde (Formula XXXVI).

Refer to Chart C. A solution of the formula-XXXV silyl ethers (Example 35, 2.54 g.) in 3.5 ml. of methanol and 26 ml. of ethyl acetate is prepared in an ozonolysis vessel fitted with a fritted glass gas inlet. The solution is treated at −78° C. with a stream of ozone in oxygen obtained from a Welsbach Ozone Generator, until a blue color is produced. The mixture is left at −78° C. for one hr., then purged with a stream of nitrogen. It is treated with 2.0 ml. of dimethylsulfide and warmed to room temperature within 16 hr. The mixture is diluted with ethyl acetate, washed with brine, dried, and concentrated. The residue is chromatographed on silica gel, eluting with ethyl acetate (10–60%)-Skellysolve B, to yield the formula-XXXVI title compounds.

EXAMPLE 37

(3aS,6aR)-Hexahydro-5α-benzoyloxy-2(α or β)-(t-butyldimethylsiloxy)-4β-(3-oxo-1-trans-octenyl)-pentalene (Formula XXXVIII).

Refer to Chart C. A solution of the formula-XXXVI aldehydes (Example 36, 3.0 g.) in 30 ml. of methylene chloride is added to a solution of the anion of dimethyl (2-oxoheptyl)phosphonate prepared from that compound (Derwent Farmdoc Abstract 10695V)(3.43 g.) and sodium hydride (0.65 g.) in 50 ml. of tetrahydrofuran. The resulting reaction mixture is stirred at about 25° C. for 2 hr., then acidified with acetic acid and concentrated. The residue is partitioned between methylene chloride and water, and the organic phase is concentrated. The residue is chromatographed on silica gel, eluting with ethyl acetate (50%)-Skellysolve B, to yield the formula-XXXVIII title compounds.

EXAMPLE 38

(3aS,6aR)-Hexahydro-5α-benzoyloxy-2(α or β)-(t-butyldimethylsiloxy)-4β-[3(α or β)-hydroxy-1-trans-octenyl]pentalene (Formula XL).

Refer to Chart C. A solution of the formula-XXXVIII compounds of Example 37 (4.65 g.) in 30 ml. of 1,2-dimethoxyethane is added to a mixture of zinc borohydride (prepared from zinc chloride (anhydrous, 6.54 g.) and sodium borohydride (1.82 g.) in 71 ml. of dry 1,2-dimethoxyethane), with stirring and cooling to −10° to 0° C. for 2 to 5 hr. and then water (12 ml.) and ethyl acetate (25 ml.) are added. The mixture is filtered, and the organic phase is separated, washed with brine, dried, and concentrated. The residue is chromatographed on silica gel, eluting with ethyl acetate (50–75%)-Skellysolve B to yield the formula-XL 3α-hydroxy and 3β-hydroxy title compounds.

EXAMPLE 39

(3aS,6aR)-Hexahydro-2-(t-butyldimethylsiloxy)-4β-(3'α-hydroxy-1-trans-octenyl)-5α-hydroxy-pentalene, 5,3'-bis-(tetrahydropyran-2-yl ether) (Formula XLIII).

I. Refer to Chart C. The benzoyl groups of the formula-XL compound are first replaced with hydrogen. A solution of the formula-XL 3α-hydroxy compound (Example 38, 3.3 g.) and potassium carbonate (1.11 g.) in 38 ml. of methanol is stirred at about 25° C. for 2 hr. Then chloroform is added and the solids removed by filtration. The filtrate is concentrated and the residue is taken up in methylene chloride, washed with brine, dried, and concentrated to yield the formula-XLII (3aS,6aR)-hexahydro-2(α or β)-(t-butyldimethylsiloxy)-4β-[1-trans-(3'α)-hydroxyoctenyl]-5α-hydroxy-pentalene.

II. The product of I above is converted to the corresponding 5,3'-bis(tetrahydropyranyl-2-yl ether) title compound by reaction with dihydropyran (5.95 ml.) in methylene chloride (45 ml.) in the presence of pyridine hydrochloride (33 mg.) at about 25° C. for 6 hr. The reaction mixture is washed with aqueous potassium bicarbonate solution, dried, and concentrated to the title compound.

EXAMPLE 40

(3aS,6aR)-Hexahydro-4β-(3'α-hydroxy-1-trans-octenyl)5α-hydroxy-pentalen-2-one (Formula XLVI).

I. Refer to Chart C. The silyl groups of the formula-XLIII compounds are first replaced with hydrogen. A solution of the formula-XLIII compound (Example 39, 2.0 g.) in 10 ml. of tetrahydrofuran is treated with 2 molar equivalents of tetra-n-butylammonium fluoride (0.5 M in tetrahydrofuran). The reaction mixture is stirred at 0°–45° C. for 2-24 hr., until complete as shown by TLC. The mixture is diluted with brine and extracted with ethyl acetate. The organic phase is washed with brine, dried, and concentrated. The residue is chromatographed on silica gel, eluting with ethyl acetate (20–75%)-Skellysolve B to yield the formula-XLIV (3aS,6aR)-hexahydro-2(α or β), 5α-dihydroxy-4β-[(3'α)-hydroxy-1-trans-octenyl]-pentalene.

II. The product of I above is next oxidized to the corresponding ketone. A solution of the product of I in 50 ml. of acetone is treated at −35° C., with stirring, with 2.0 equivalents of Jones Reagent (2.67 M). The mixture is stirred at −35° to −5° C. until completed, within one hr., then quenched with one ml. of isopropyl alcohol and further stirred at −20° to −15° C. for 15 min. The mixture is diluted with brine and extracted with ethyl acetate. The organic phase is washed with brine, dried, and concentrated. The residue is chromatographed on silica gel, eluting with ethyl acetate (10–65%)-Skellysolve B to yield the formula-XLV 5,3'-bis(tetrahydropyran-2-yl ether) of the title compound.

III. The product of II above is deblocked by contact with acetic acid-water-tetrahydrofuran (20:10:3) at 40° C. for 4 hr. The solution is then diluted with brine and extracted with ethyl acetate. The organic phase is washed with brine and saturated aqueous sodium bicarbonate, dried, and concentrated. The residue is chromatographed on silica gel, eluting with ethyl acetate (10–65%)-Skellysolve B to yield the title compound.

EXAMPLE 41

(5E)-6a-Carba-16,16-dimethyl-PGI$_2$ and (5Z)-6a-Carba-16,16-dimethyl-PGI$_2$ (Formula V).

I. Refer to Chart C. A solution of the formula-XXXVI aldehydes namely (3aS,6aR)-hexahydro-5α-benzoyloxy-2(α or β)-(t-butyldimethylsiloxy)-4β-pentalenecarboxaldehyde (Example 36) in methylene chloride is added to a solution of the anion of dimethyl 2-oxo-3,3-dimethylheptylphosphonate (U.S. Pat. No. 3,954,833) prepared by reaction of that compound with sodium hydride in tetrahydrofuran. Thereafter, following the procedure of Example 37, the formula-XXXVIII compounds, namely (3aS,6aR)-hexahydro-5α-benzoyloxy-2(α or β)-(t-butyldimethylsiloxy)-4β-(3-oxo-4,4-dimethyl-trans-1-octenyl)-pentalene are obtained.

II. Following the procedures of Example 38, the product of I above is reduced with zinc borohydride and the resulting 3α and 3β-hydroxy isomers are separated.

III. Thereafter following the procedures of Examples 39-I and -II and 40-I and -II, and referring to Chart C, the corresponding formula-XLV compounds are obtained in which R$_{11}$ is —C(CH$_3$)$_2$—(CH$_2$)$_3$—CH$_3$.

IV. Refer to Chart K. The formula-XLV compound of III above, namely (3aS,6aR)-hexahydro-4β-[(3'α)-hydroxy-4,4-dimethyl-trans-1-octenyl]-5α-hydroxypentalene-2-one, 5,3'-bis-tetrahydropyran-2-yl ether, is reacted with a sulfoximine reagent, namely N-methyl-S-(ω-hydroxypentyl)-S-phenylsulfoximine, t-butyldimethylsilyl ether, obtained by modifying the procedures of Example 10, using the t-butyldimethylsilyl ether of 5-bromopentanol. Following the procedures of Example 11, there are obtained the formula-XCVIII compounds, namely 6a-carba-2-decarboxy-2-hydroxymethyl-6-hydroxy-5-(N-methylphenylsulfonimidoyl)-16,16-dimethyl-PGI$_1$, 1-(t-butyldimethylsilyl ether), 11,15-bis(tetrahydropyran-2-yl ether).

V. The product of IV above is treated with aluminum amalgam to form the formula-XCIX (5E and 5Z)-6a-carba-2-decarboxy-2-hydroxymethyl-16,16-dimethyl-PGI$_2$, 1-(t-butyldimethylsilyl ether), 11,15-bis(tetrahydropyran-2-yl ether).

VI. The formula-C compounds are obtained by hydrolyzing the product of V in a solution of acetic acid-water-tetrahydrofuran (20:10:3) at about 40° C. for 3 hr., following the procedures of Example 40-III.

VII. The formula-CI compounds are obtained by benzoylation (see Example 34).

VIII. The formula-XVII compounds are obtained on removal of silyl groups with tetrabutylammonium fluoride (see Example 19-I) to yield (5E and 5Z)-6a-carba-2-decarboxy-2-hydroxymethyl-16,16-dimethyl-PGI$_2$, 11,15-dibenzoate. The C-5 E and Z isomers are separated by HPLC on silica gel, using a high pressure liquid column.

IX. The formula-XVIII acids are obtained on oxidizing the products of VIII with Jones reagent (see Example 14-I).

X. Finally, the title compounds are obtained on deblocking the products of IX, using potassium carbonate in methanol as in Example 39-I.

Following the procedures of Example 41 and referring to Chart C, but replacing the Wittig reagent of that example with the anion derived from each of

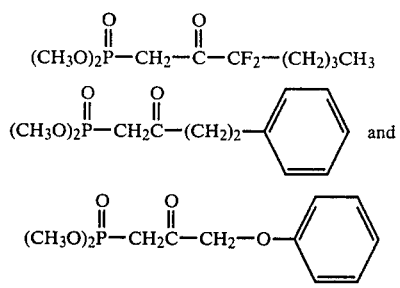

there are obtained the corresponding products, namely (5E) and (5Z)-6a-carba-16,16-difluoro-PGI$_2$; (5E) and (5Z)-6a-carba-17-phenyl-18,19,20-trinor-PGI$_2$ and (5E) and (5Z)-6a-carba-16-phenoxy-17,18,19,20-tetranor-PGI$_2$.

Following the procedures of Example 41 but at step IV replacing the sulfoximine reagent with a sulfoximine of the formula

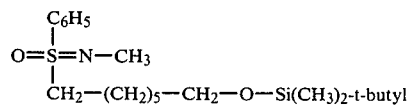

there are obtained the corresponding (5E)-6a-carba-2a,2b-dihomo-16,16-dimethyl-PGI$_2$ and (5Z)-6a-carba-2a,2b-dihomo-16,16-dimethyl-PGI$_2$.

Likewise using a sulfoximine reagent of the formula

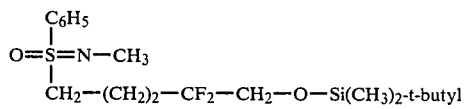

there are obtained the corresponding (5E)-6a-carba-2,2-difluoro-16,16-dimethyl-PGI$_2$ and (5Z)-6a-carba-2,2-difluoro-16,16-dimethyl PGI$_2$. From these acids the corresponding methyl esters are prepared using the procedure of Example 21-II.

EXAMPLE 42

(3aS,6aR)-Hexahydro-5α-hydroxy-4β-(3S-hydroxy-1-cis-octenyl)-pentalen-2-one (Formula LIII: Q₁ is

and the corresponding 3R-hydroxy isomer (Formula LIII: Q₁ is

I. Refer to Chart D. A solution of the formula-XLVII (3aS,6aR)-hexahydro-2(α or β)-acetoxy-5α-(t-butyl-dimethylsiloxy)-4β-(3-oxo-1-trans-octenyl)-pentalene (Example 47-III; 1.6 g.) in 100 ml. of acetone (agitated by bubbling nitrogen through the solution) is irradiated for 3 hr. in a Rayonet Photochemical Reactor (Type RS Preparative Photochemical Reactor) wherein the photo emission spectrum of the lamps shows substantial intensity at a wavelength at or near 3500 Angstroms. The solution is then concentrated and the residue is chromatographed on silica gel, eluting with acetone (5–40%)-methylene chloride to yield the formula-XLVIII (cis) compound and recovered (trans) starting material.

II. The product of I is reduced with zinc borohydride by the procedure of Example 38 to form the corresponding (3aS,6aR)-hexahydro-2(α or β)-acetoxy-5α-(t-butyldimethylsiloxy)-4β-(3S-hydroxy-1-cis-octenyl)-pentalene and its 3R-hydroxy isomer. These isomers are separated by silica gel chromatography.

III. Following the procedure of Example 9 and reacting each of the above products with t-butyldimethylsilyl chloride, there is obtained the corresponding formula-L (3aS,6aR)-hexahydro-2(α or β)-acetoxy-5α-(t-butyldimethylsiloxy)-4β-(3S-hydroxy-1-cis-octenyl)-pentalene, 3-t-butyldimethylsilyl ether and its 3R-hydroxy isomer.

IV. The formula-LIII pentalen-2-one is prepared in two steps, following first the procedure of Example 5-II in replacing the acetoxy group of each of the products of III above by saponification with aqueous potassium hydroxide. Thereafter, following the procedure of Example 6, the resulting 2-hydroxy compounds are oxidized with Jones reagent to the desired formula-LII compound, namely (3aS,6aR)-hexahydro-5α-(t-butyldimethylsiloxy)-4β-3S-hydroxy-1-cis-octenyl)-pentalen-2-one, 3-t-butyldimethylsilyl ether, and its 3R-hydroxy isomer.

V. The formula-LIII title (cis) 3S-hydroxy and 3R-hydroxy compounds are finally obtained by replacing the siloxy groups with hydrogen in the product of IV, using tetrabutylammonium fluoride solution as in Example 13-I.

EXAMPLE 43

(3aS,6aR)-Hexahydro-5α-hydroxy-4β-(3α-hydroxy-1-octyl)-pentalen-2-one (Formula LV).

Refer to Chart E. A solution of the formula-LIV (3aS,6aR)-hexahydro-5α-hydroxy-4β-(3α-hydroxy-1-trans-octenyl)-pentalen-2-one (Example 8, 0.1 g.) in 10 ml. of ethyl acetate is shaken with hydrogen at about one atmosphere pressure at about 25° C. in the presence of a 5% palladium-on-charcoal catalyst (15 mg.). When one equivalent of hydrogen has been used, the hydrogenation is stopped and the catalyst is removed by filtration. The filtrate is concentrated and the residue is chromatographed on silica gel, eluting with acetone (20–40%)-methylene chloride to yield the title compound.

EXAMPLE 44

(3aS,6aR)-Hexahydro-5α-hydroxy-4β-(3α-hydroxy-1-octynyl)-pentalen-2-one (Formula LXV)

I. Refer to Chart F. There is first prepared the formula-LVIII dihalo compound wherein R₃₅ is chloro. Starting with the formula-XLVII (3aS,6aR)-hexahydro-2(α or β)-acetoxy-5α-(t-butyldimethylsiloxy)-4β-(3-oxo-1-trans-octenyl)-pentalene (Example 47-III, 1.5 g.), the silyl groups are replaced with THP. The compound, in 10 ml. of tetrahydrofuran, is treated with 9 ml. of a solution of tetrabutylammonium fluoride (0.5 M in tetrahydrofuran) at about 10°–40° C. until silyl groups are replaced with hydrogen. The mixture is cooled, diluted with brine and extracted with ethyl acetate. The organic phase is washed with ice-cold 1 N potassium hydrogen sulfate, saturated aqueous sodium bicarbonate, and brine, dried, and concentrated. The formula-LVI product is then reacted with dihydropyran (3 ml.) in methylene chloride in the presence of pyridine hydrochloride (20 mg.) at about 25° C. for 6 hr. The reaction mixture is washed with aqueous potassium bicarbonate solution, dried, and concentrated to the formula-LVII (3aS,6aR)-hexahydro-2-(α or β)-acetoxy-5α-(tetrahydropyran-2-yl ether)-4β-(3-oxo-1-trans-octenyl)-pentalene. That compound is treated in dioxane (35 ml.) with N-chlorosuccinimide (9.7 g.) at about 25° C. for 6 days. The resulting solution is diluted with methylene chloride, washed with brine, dried, and concentrated. The residue is chromatographed to yield the 1,2-dichloro derivative.

II. The formula-LIX monochloro compound is obtained by dehydrohalogenating the product of I in pyridine (20 ml.) at 95°–100° C. for about 2 hr. The mixture is cooled, diluted with diethyl ether and washed with ice-cold dilute hydrochloric acid and brine. The organic phase is dried and concentrated. The residue is chromatographed to yield the monochloro compound.

III. The product of II is reduced to the formula-LX compounds with zinc borohydride following the procedure of Example 38. The 3α- and 3β-hydroxy compounds are separated by silica gel chromatography, thereby obtaining the formula-LX (3aS,6aR)-hexahydro-2(α or β)-acetoxy-5α-(tetrahydropyran-2-yloxy)-4β-(2-chloro-3α-hydroxy-1-trans-octenyl)-pentalene and its 3β isomer.

IV. The formula-LXI 3α bis(THP ether) is obtained by reaction of the 3α product of III with dihydropyran in methylene chloride in the presence of pyridine hydrochloride following the procedure in I above.

V. The formula-LXII didehydro compound is obtained by further dehydrohalogenation. The product of IV is treated with potassium t-butoxide in t-butanol at about 25° C. for 3.5 hr. Thereafter the mixture is further treated with 10% aqueous potassium hydroxide at about 25° C. for one hr. to insure replacement of the acetyl groups. The reaction mixture is acidified (pH 5) with acetic acid, diluted with brine, and extracted with ethyl acetate. The organic phase is washed with saturated sodium bicarbonate and brine, dried, and concentrated.

The residue is chromatographed on silica gel to yield the mixed formula-LXIII compounds.

VI. The product of V is oxidized to a ketone with Jones reagent following the procedure of Example 6 to yield the formula-LXIV compound.

VII. The tetrahydropyranyl blocking groups of the product of VI are replaced using acetic acid-water-tetrahydrofuran (20:10:3) at 40° C. for 3 hr. Work-up yields the formula-LXV title compound.

Following the procedures of Example 44-IV through VII but utilizing the 3β-hydroxy isomer of III there is obtained the corresponding formula-LXV 3β-hydroxy pentalenone.

EXAMPLE 45

(5E)-6a-Carba-11β-PGI$_2$, Methyl Ester (Formula V)
(5Z)-6a-Carba-11β-PGI$_2$, Methyl Ester (Formula V).

I. Refer to Chart J. The formula-XCI methyl ester of (5E)-6a-carba-11-dehydro-PGI$_2$, 15-tetrahydropyran-2-yl ether is prepared from the formula-XC corresponding (5E) free acid (Example 47-VIII) by reaction in acetonitrile with methyl iodide in the presence of diisopropylethylamine at about 25° C., following the procedures of Example 21-II.

II. The formula-XCII (5E)-6a-carba-11-dehydro-PGI$_2$, 15-trimethylsilyl ether, methyl ester, is then prepared by first replacing the tetrahydropyranyl groups of the product of I above with hydrogen by acid hydrolysis, following the procedures of Example 13-III. Thereafter the resulting product is silylated, using N-trimethylsilyldiethylamine in acetone solution at about −50° C. for 2.5 hr., followed by a conventional work-up.

III. The formula-XCIII (5E)-6a-carba-11(α or β)-PGI$_2$, 15-trimethylsilyl ether, methyl ester compounds are then prepared by reducing the product of II above with sodium borohydride following the procedures of Example 35-I.

IV. The formula-XCIV compounds are obtained on hydrolysis of the silyl ether of the products of III above, using methanol-water-acetic acid (6:1:0.1) at about 35° C. for 15 min.

V. The product of IV above is chromatographed on silica gel, eluting with ethyl acetate (20–100%)-Skellysolve B to separate the 11α (more polar) and 11β (less polar) isomers of the formula-XCV (5E) compounds.

Likewise following steps I–V of Example 45 but starting with the (5Z) free acid of Example 47-VIII, there is prepared the corresponding formula-XCV title compound, namely (5Z)-6a-carba-11β-PGI$_2$, methyl ester.

The acids corresponding to the title compounds of Example 45 are readily obtained following saponification with 5% potassium hydroxide in methanol-water (9:1) at about 25° C.

EXAMPLE 46

(5E)-6a-Carba-11-deoxy-PGI$_2$ (Formula V) and
(5Z)-6a-Carba-11-deoxy-PGI$_2$ (Formula V)

I. Refer to Charts H and K. The formula-LXXVI starting material, namely (3aS,6aR)-hexahydro-2(α or β)-acetoxy-5α-(t-butyldimethylsiloxy)-4β-(3α-hydroxy-1-trans-octenyl)-pentalene, 3-tetrahydropyran-2-yl ether is available from Example 47-IV. The 5-silyl groups are replaced with hydrogen, using tetrabutylammonium fluoride and following the procedures of Example 13-I above to yield the formula-LXXVII compounds.

II. The formula-LXXVIII 5-mesylate is prepared from the product of I above, by carrying out the reaction in pyridine at 0° C., using methylsulfonyl chloride. The mixture is finally quenched with ice and water, acidified with ice-cold 1 M hydrochloric acid, and extracted with methylene chloride. The organic phase is washed with dilute, ice-cold 1 M hydrochloric acid, water, aqueous sodium bicarbonate, and brine, dried, and concentrated to the formula-LXXVIII compound, namely (3aS,6aR)-hexahydro-2(α or β)-acetoxy-5α-(methylsulfonyloxy)-4β-(3α-hydroxy-1-trans-octenyl)-pentalene, 3-tetrahydropyran-2-yl ether.

III. The formula-LXXIX compounds are prepared by first reducing the product of II above with lithium aluminum hydride (4-equivalents) in diethyl ether at about 25° C. until complete, approximately one to five hours. The reaction mixture is quenched with water and 10% sodium potassium tartrate and brine. The layers are separated and the organic phase is washed with brine, dried, and concentrated. The residue is chromatographed on silica gel, eluting with ethyl acetate (25–75%)-Skellysolve B to yield the formula-LXXIX compounds, namely (3aS,6aR)-hexahydro-2α-hydroxy-4β-(3α-hydroxy-1-trans-octenyl)-pentalene, 3-tetrahydropyran-2-yl ether, and the corresponding 2β-hydroxy isomer.

IV. The formula-LXXX pentalen-2-one is obtained on oxidizing the separated or mixed 2-hydroxy isomers of III above with Jones reagent following the procedures of Example 40-II.

V. Refer to Chart K. The formula-XCVIII sulfonimidoyl compound is obtained following the procedures of Example 41-IV, using a sulfoximine reagent that is terminated with t-butyldimethylsilyl. Accordingly there is obtained the formula-XCVIII 6a-carba-2-decarboxy-2-hydroxymethyl-6ξ-hydroxy-5ξ-(n(methylphenylsulfonimidoyl)-11-deoxy-PGI$_1$, 1-t-butyldimethylsilyl ether, 15-tetrahydropyran-2-yl ether.

VI. The formula-IX title compounds are obtained following the procedures of Example 47-VII through IX. The product of V above is treated with aluminum amalgam to yield formula-XCIX (5E and 5Z)-6a-carba-2-decarboxy-2-hydroxymethyl-11-deoxy-PGI$_2$, 1-(t-butyldimethylsilyl ether), 15-(tetrahydropyran-2-yl ether). The tetrahydropyranyl groups are replaced with benzoyl groups by conventional means, as by hydrolysis of Example 19-III and benzoylation of Example 34. Thereafter the silyl groups of CI are replaced with hydrogen, using tetrabutylammonium fluoride (see Example 19-I), and the C-5E and Z isomers are separated by silica gel chromatography. Next the terminal hydroxy groups are oxidized with Jones reagent at about −10° C. to obtain (5E)-6a-carba-11-deoxy-PGI$_2$ and the (5Z) isomer, as their 15-benzoate esters of formula XVIII. Finally the benzoate groups are replaced with hydrogen by conventional means, as in Example 39-I, to yield the respective title compounds.

EXAMPLE 47

(5E)-6a-Carba-11-dehydro-PGI$_2$ and (5Z) isomer (Formula V)

I. Refer to Charts I and L. Starting with the formula-XXXII pentalen-2-one, there are first prepared the corresponding 2-hydroxy compounds. A solution of the formula-LXXXII pentalen-2-one, 3,5-bis-(t-butyldimethylsilyl ether) (Example 9, 2.47 g.) in 5 ml. of methanol is added to a mixture of sodium borohydride (0.38 g.) in 40 ml. of methanol and 10 ml. of water at −20° C. to −10° C. with vigorous stirring for one hr. The reaction is then quenched with one ml. of acetic acid followed by brine. The mixture is extracted with ethyl acetate and the organic phase is washed with saturated aqueous sodium bicarbonate and brine, dried and concentrated to yield the formula-LXXXIII 2-hydroxy compounds.

II. The formula-LXXXIV 2-acetoxy compounds are prepared by treating the product of I above, in pyridine, in an ice bath with 3 ml. of acetic anhydride and 0.03 g. of 4-(N,N-dimethylamino)-pyridine. When the reaction is complete, in about one hr. at 25° C., the mixture is diluted with brine and extracted with ethyl acetate. The organic phase is washed with ice-cold 1 N hydrochloric acid, saturated aqueous sodium bicarbonate, and brine, dried, and concentrated to yield the isomeric formula-LXXXIV compounds.

III. The formula-XLVII 15-oxo compounds are prepared in two steps, following the procedures of Examples 36 and 37 but replacing the starting material of Example 36 with the product of II above. Accordingly, by ozonolysis there is obtained the corresponding formula-LXXXV (3aS,6aR)-hexahydro-2($\alpha$ or $\beta$)-acetoxy-5$\alpha$-(t-butyldimethylsiloxy)-4$\beta$-pentalenecarboxaldehyde. Thereafter, applying the Wittig reaction as in Example 37, there is obtained the formula-XLVII (3aS,6aR)-hexahydro-2($\alpha$ or $\beta$)-acetoxy-5$\alpha$-(t-butyldimethylsiloxy)-4$\beta$-(3-oxo-1-trans-octenyl)-pentalene.

IV. The formula-LXXXVII 15-tetrahydropyran-2-yl ether compounds are prepared in two steps, following first, the procedure of Example 38 to reduce the product of III above with zinc borohydride and thereby form the corresponding formula LXXXVI (3aS,6aR)-hexahydro-2($\alpha$ or $\beta$)-acetoxy-5$\alpha$-(t-butyldimethylsiloxy)-4$\beta$-(3$\alpha$-hydroxy-1-trans-octenyl)-pentalene and its 3$\beta$-hydroxy isomer. These isomers are separated by silica gel chromatography. Thereafter, following the procedure of Example 40-II and reacting each compound with dihydropyran, there is obtained the corresponding formula-LXXXVII (3aS,6aR)-hexahydro-2($\alpha$ or $\beta$)-acetoxy-5$\alpha$-(t-butyldimethylsiloxy)-4$\beta$-(3$\alpha$-hydroxy-1-trans-octenyl)-pentalene, 3-tetrahydropyran-2-yl ether and its 3$\beta$-hydroxy isomer.

V. The formula-LXXXIX pentalen-2-one is prepared in two steps, following first the procedure of Example 5-II in deblocking the acetoxy group of the product of IV above by saponification with aqueous potassium hydroxide. Thereafter, following the procedure of Example 6, the resulting 2-hydroxy compounds are oxidized with Jones reagent to the desired formula-LXXXIX compound, namely (3aS,6aR)-hexahydro-5$\alpha$-(t-butyldimethylsiloxy)-4$\beta$-(3$\alpha$-hydroxy-1-trans-octenyl)-pentalen-2-one, 3-tetrahydropyran-2-yl ether.

VI. Refer to Chart L. The formula-CIII sulfonimidoyl compound is obtained following the procedures of Example 11 using the N-methyl-S-($\omega$-hydroxypentyl)-S-phenylsulfoximine, t-butyldimethylsilyl ether of Example 41-IV. Accordingly, the product of V above is converted to the corresponding formula-CIII compounds namely 6a-carba-2-decarboxy-2-hydroxymethyl-6$\xi$-hydroxy-5$\xi$-(N-methylphenylsulfonimidoyl)-PGI$_1$, 11-bis(t-butyldimethylsilyl ether), 15-tetrahydropyran-2-yl ether.

VII. The formula-CIV and -CV compounds are prepared following the procedures of Examples 12 and 13. The product of VI above is treated with aluminum amalgam to form the corresponding formula-CIV (5E and 5Z)-6a-carba-2-decarboxy-2-hydroxymethyl-PGI$_2$, 1,11-bis(t-butyldimethylsilyl ether), 15-tetrahydropyran-2-yl ether. Thereafter, following the deblocking procedures of Example 13 to replace silyl groups with hydrogen, the corresponding formula-CV compounds are obtained, namely (5E and Z)-6a-carba-2-decarboxy-2-hydroxymethyl-PGI$_2$, 15-tetrahydropyran-2-yl ether. The C-5E and Z isomers are separated by silica gel chromatography following Example 13.

VIII. The formula-CVI compounds are prepared following the procedures of Example 14, oxidizing the products of VII above, separately, with Jones reagent at about −10° C. to obtain the formula-CVI (5E)-6a-carba-11-dehydro-PGI$_2$ and (5Z) isomer, as their 15-tetrahydropyran-2-yl ethers.

IX. The formula-CVIII title compounds are finally obtained by replacing tetrahydropyranyl groups with hydrogen in the products of VIII, using acid-hydrolysis as in Example 13-III.

EXAMPLE 48

(5E)-6a-Carba-PGI$_2$ and (5Z)-6a-Carba-PGI$_2$. (Formula V)

I. Refer to Chart P. A mixture of 9 ml. of dimethylsulfoxide and 0.26 g. of sodium hydride (57% dispersion in mineral oil) is heated with stirring at 65° C. under nitrogen for 1.5 hr. The resulting solution of sodio dimethylsulfinylcarbanide ("dimsyl") is then treated at 10° C. with 1.35 g. of 4-carboxybutyltriphenylphosphonium bromide. After 20 min. at 20° C., a solution of 0.66 g. of formula-CXX pentalenone, bis(tetrahydropyranyl ether) (Example 40-II) in 2 ml. of dimethylsulfoxide is added to the red ylid solution dropwise with stirring at 10° C. during 5 min. The reaction mixture is treated with 1.0 M aqueous potassium bisulfate to pH 2–3, diluted with brine and extracted with diethyl ether. The combined extract is washed with brine, dried and concentrated to give a crude product containing compounds of formula-CXXII.

II. The mixture of compounds from step I is treated with acetic acid-water-tetrahydrofuran (20:10:3) at 40° C. for 3 hr. The reaction mixture is diluted with water and freeze-dried to give an organic residue containing compounds of formula-IX. These isomeric compounds are separated by chromatography over silica gel, eluting with Skellysole B-ethyl acetate-acetic acid (65:33:2).

EXAMPLE 49

(5E)-6a-Carba-PGI$_2$, p-Benzamidophenyl Ester (Formula V).

Refer to U.S. Pat. No. 3,968,140. A solution of (5E)-6a-carba-PGI$_2$ (Example 15) in triethylamine is treated at −20° C. with a slight excess of isobutylchloroformate. After 5 min. the mixture is treated with an equivalent amount of p-benzamidophenol in pyridine and stirred at about 25° C. for 2 hr. The mixture is concentrated and the residue is taken up in ethyl acetate, washed with water, dried, concentrated, and chromatographed to yield the title compound.

I claim:

1. A compound of the formula

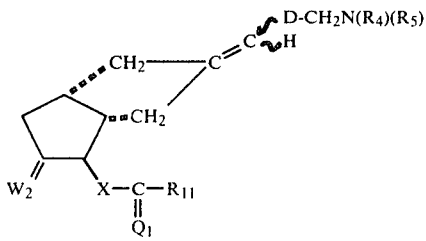

wherein $W_2$ is $\alpha$-OH:$\beta$-H, $\alpha$-H:$\beta$-OH, oxo, or $\alpha$-H:$\beta$-H; wherein D is
(1) —(CH$_2$)$_d$—, wherein d is one to 5, inclusive,
(2) —(CH$_2$)$_d$—CF$_2$—, wherein d is one to 5, inclusive,
(3) —(CH$_2$)$_k$—CH=CH—, wherein k is one or 2;
wherein one of $R_4$ and $R_5$ is hydrogen, and the other is hydrogen, alkyl of one to 12 carbon atoms, inclusive, benzyl, or phenyl;
wherein $R_{11}$ is

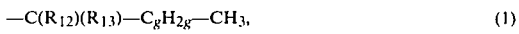

wherein $C_gH_{2g}$ is alkylene of one to 9 carbon atoms, inclusive, with one to 5 carbon atoms, inclusive, in the chain between —CR$_{12}$R$_{13}$— and terminal methyl, wherein $R_{12}$ and $R_{13}$ are hydrogen, alkyl of one to 4 carbon atoms, inclusive, or fluoro, being the same or different, with the proviso that one of $R_{12}$ and $R_{13}$ is fluoro only when the other is hydrogen or fluoro;

wherein $R_{12}$ and $R_{13}$ are as defined above; wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive between —CR$_{12}$R$_{13}$— and (Ph), wherein (Ph) is phenyl or phenyl substituted by (T)s, wherein T is alkyl of one to 4 carbon atoms, inclusive, fluoro, chloro, trifluoromethyl, or —OR$_{14}$, wherein R$_{14}$ is alkyl of one to 4 carbon atoms, inclusive, and s is zero, one, 2, or 3, with the proviso that not more than two T s are other than alkyl and when s is 2 or 3 the T s are either the same or different; or

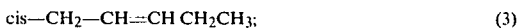

ps wherein $Q_1$ is $\alpha$-OH:$\beta$-R$_8$ or $\alpha$-R$_8$:$\beta$-OH, wherein R$_8$ is hydrogen or methyl;
wherein X is trans—CH=CH—, cis-CH=CH—, —C≡C—, or —CH$_2$CH$_2$—.

2. A compound according to claim 1, wherein X is —CH$_2$CH$_2$—.

3. A compound according to claim 2, wherein $Q_1$ is $\alpha$-OH:$\beta$-R$_8$, wherein R$_8$ is hydrogen or methyl.

4. A compound according to claim 3, wherein R$_8$ is hydrogen.

5. A compound according to claim 4, wherein $W_2$ is $\alpha$-OH:$\beta$-H.

6. 2-Decarboxy-2-aminomethyl-(5E)-6a-carba-13,14-dihydro-PGI$_2$, a compound according to claim 5.

7. 2-Decarboxy-2-aminomethyl-(5Z)-6a-carba-13,14-dihydro-PGI$_2$, a compound according to claim 5.

8. A compound according to claim 3, wherein R$_8$ is methyl.

9. A compound according to claim 8, wherein $W_2$ is $\alpha$-OH:$\beta$-H.

10. 2-Decarboxy-2-aminomethyl-(5E)-6a-carba-13,14-dihydro-(15S)-15-methyl-PGI$_2$, a compound according to claim 9.

11. 2-Decarboxy-2-aminomethyl-(5Z)-6a-carba-13,14-dihydro-(15S)-15-methyl-PGI$_2$, a compound according to claim 9.

12. A compound according to claim 1, wherein X is trans—CH=CH—.

13. A compound according to claim 12, wherein $Q_1$ is $\alpha$-OH:$\beta$-R$_8$.

14. A compound according to claim 13, wherein R$_8$ is hydrogen.

15. A compound according to claim 14, wherein $W_2$ is $\alpha$-H:$\beta$-OH.

16. 2-Decarboxy-2-aminomethyl-(5E)-6a-carba-11$\beta$-PGI$_2$, a compound according to claim 15.

17. 2-Decarboxy-2-aminomethyl-(5Z)-6a-carba-11$\beta$-PGI$_2$, a compound according to claim 15.

18. A compound according to claim 14, wherein $W_2$ is oxo.

19. 2-Decarboxy-2-aminomethyl-(5E)-6a-carba-11-dehydro-PGI$_2$, a compound according to claim 18.

20. 2-Decarboxy-2-aminomethyl-(5Z)-6a-carba-11-dehydro-PGI$_2$, a compound according to claim 18.

21. A compound according to claim 14, wherein $W_2$ is $\alpha$-H:$\beta$-H.

22. 2-Decarboxy-2-aminomethyl-(5E)-6a-carba-11-deoxy-PGI$_2$, a compound according to claim 21.

23. 2-Decarboxy-2-aminomethyl-(5Z)-6a-carba-11-deoxy-PGI$_2$, a compound according to claim 21.

24. A compound according to claim 14, wherein $W_2$ is $\alpha$-OH:$\beta$-H.

25. A compound according to claim 24, wherein D is —(CH$_2$)$_d$—, wherein d is one to 5, inclusive.

26. A compound according to claim 25, wherein D is —(CH$_2$)$_3$—.

27. A compound according to claim 26, wherein $R_{11}$ is n-pentyl.

28. 2-Decarboxy-2-aminomethyl-(5E)-6a-carba-PGI$_2$, a compound according to claim 27.

29. 2-Decarboxy-2-aminomethyl-(5Z)-6a-carba-PGI$_2$, a compound according to claim 27.

30. A compound according to claim 26, wherein $R_{11}$ is —C(CH$_3$)$_2$—(CH$_3$)$_3$—CH$_3$.

31. 2-Decarboxy-2-aminomethyl-(5E)-6a-carba-16,16-dimethyl-PGI$_2$, a compound according to claim 30.

32. 2-Decarboxy-2-aminomethyl-(5Z)-6a-carba-16,16-dimethyl-PGI$_2$, a compound according to claim 30.

33. A compound according to claim 26, wherein $R_{11}$ is cis—CH$_2$—CH=CH—CH$_2$CH$_3$.

34. 2-Decarboxy-2-aminomethyl-(5E)-6a-carba-PGI$_3$, a compound according to claim 33.

35. 2-Decarboxy-2-aminomethyl-(5Z)-6a-carba-PGI$_3$, a compound according to claim 33.

36. A compound according to claim 25, wherein D is —(CH$_2$)$_5$—.

37. A compound according to claim 36, wherein $R_{11}$ is n-pentyl.

38. 2-Decarboxy-2-aminomethyl-(5E)-6a-carba-2a,2b-dihomo-PGI$_2$, a compound according to claim 37.

39. 2-Decarboxy-2-aminomethyl-(5Z)-6a-carba-2a,2b-dihomo-PGI$_2$, a compound according to claim 38.

40. A compound according to claim 36, wherein $R_{11}$ is —C(CH$_3$)$_2$—(CH$_3$)$_3$—CH$_3$.

41. 2-Decarboxy-2-aminomethyl-(5E)-6a-carba-2a,2b-dihomo-16,16-dimethyl-PGI$_2$, a compound according to claim 40.

42. 2-Decarboxy-2-aminomethyl-(5Z)-6a-carba-2a,2b-dihomo-16,16-dimethyl-PGI$_2$, a compound according to claim 40.

43. A compound according to claim 24, wherein D is —(CH$_2$)$_2$—CF$_2$—.

44. A compound according to claim 43, wherein R$_{11}$ is n-pentyl.

45. 2-Decarboxy-2-aminomethyl-(5E)-6a-carba-2,2-difluoro-PGI$_2$, a compound according to claim 44.

46. 2-Decarboxy-2-aminomethyl-(5Z)-6a-carba-2,2-difluoro-PGI$_2$, a compound according to claim 44.

47. A compound according to claim 43, wherein R$_{11}$ is —C(CH$_3$)$_2$—(CH$_3$)$_3$—CH$_3$.

48. 2-Decarboxy-2-aminomethyl-(5E)-6a-carba-2,2-difluoro-16,16-dimethyl-PGI$_2$, a compound according to claim 47.

49. 2-Decarboxy-2-aminomethyl-(5Z)-6a-carba-2,2-difluoro-16,16-dimethyl-PGI$_2$, a compound according to claim 48.

50. A compound according to claim 13, wherein R$_8$ is methyl.

51. A compound according to claim 50, wherein W$_2$ is α-OH:β-H.

52. A compound according to claim 51, wherein D is —(CH$_2$)$_d$, wherein d is one to 5, inclusive.

53. A compound according to claim 52, wherein D is —(CH$_2$)$_3$—.

54. 2-Decarboxy-2-aminomethyl-(5E)-6a-carba-(15S)-15-methyl-PGI$_2$, a compound according to claim 53.

55. 2-Decarboxy-2-aminomethyl-(5Z)-6a-carba-(15S)-15-methyl-PGI$_2$, a compound according to claim 53.

56. A compound according to claim 52, wherein D is —(CH$_2$)$_5$—.

57. 2-Decarboxy-2-aminomethyl-(5E)-6a-carba-2a,2b-dihomo-(15S)-15-methyl-PGI$_2$, a compound according to claim 56.

58. 2-Decarboxy-2-aminomethyl-(5Z)-6a-carba-2a,2b-dihomo-(15S)-15-methyl-PGI$_2$, a compound according to claim 56.

59. A compound according to claim 51, wherein D is —(CH$_2$)$_2$—CF$_2$—.

60. 2-Decarboxy-2-aminomethyl-(5E)-6a-carba-2,2-difluoro-(15S)-15-methyl-PGI$_2$, a compound according to claim 58.

61. 2-Decarboxy-2-aminomethyl-(5Z)-6a-carba-2,2-difluoro-(15S)-15-methyl-PGI$_2$, a compound according to claim 58.

62. A compound according to claim 12, wherein Q$_1$ is α-R$_8$:β-OH.

63. A compound according to claim 61, wherein R$_8$ is hydrogen.

64. 2-Decarboxy-2-aminomethyl-(5E)-6a-carba-15R-PGI$_2$, a compound according to claim 62.

65. 2-Decarboxy-2-aminomethyl-(5Z)-6a-carba-15R-PGI$_2$, a compound according to claim 62.

66. A compound according to claim 61, wherein R$_8$ is methyl.

67. 2-Decarboxy-2-aminomethyl-(5E)-6a-carba-(15R)-15-methyl-PGI$_2$, a compound according to claim 65.

68. 2-Decarboxy-2-aminomethyl-(5Z)-6a-carba-(15R)-15-methyl-PGI$_2$, a compound according to claim 65.

* * * * *

UNITED STATES PATENT OFFICE
CERTIFICATE OF CORRECTION

Patent No. 4,238,414         Dated  9 December 1980

Inventor(s)  Douglas R. Morton, Jr.

It is certified that error appears in the above-identified patent and that said Letters Patent are hereby corrected as shown below:

Column 1, line 43, "-(CH$_2$)$_2$-," should read -- -(CH$_2$)$_d$-, --;
Column 4, lines 21-29, that portion of the formula reading

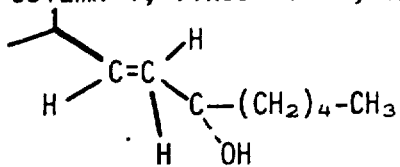    should read    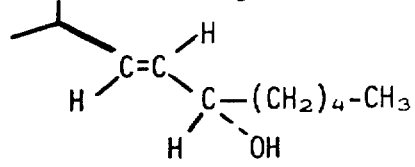

Column 4, lines 39-44, the formula should appear as follows:

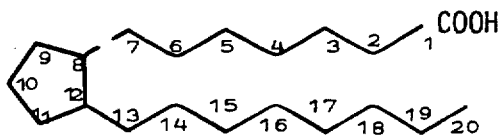

Column 5, lines 51-52, "administered intravenous infusion" should read -- administered by intravenous infusion --;
Column 7, line 50, "alternateive route" should read -- alternative route --;
Column 15, lines 1-8,

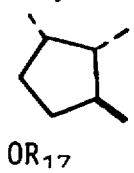    should read    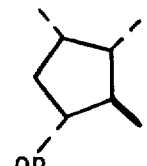

Column 21, lines 1-12, that portion of the formula reading

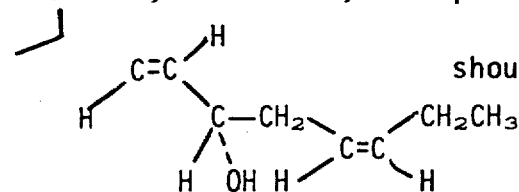    should read    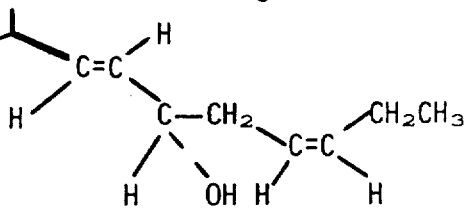

Page 2 of 3 Pages

UNITED STATES PATENT OFFICE
CERTIFICATE OF CORRECTION

Patent No. 4,238,414   Dated 9 December 1980

Inventor(s) Douglas R. Morton, Jr.

It is certified that error appears in the above-identified patent and that said Letters Patent are hereby corrected as shown below:

Column 48, lines 8-17, that portion of formula LIX reading

 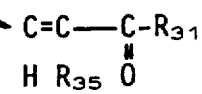   should read    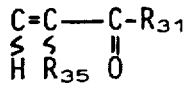

Column 48, lines 23-32, that portion of formula LX reading

 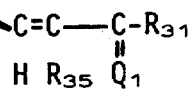   should read    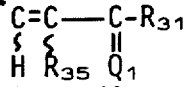

Column 48, lines 37-47, that portion of formula LXI reading

 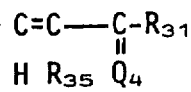   should read    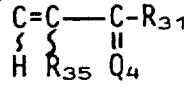

Column 52, lines 2-12,

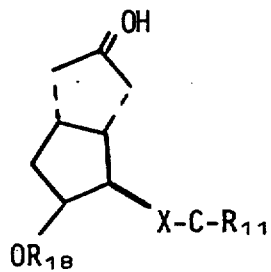   should read   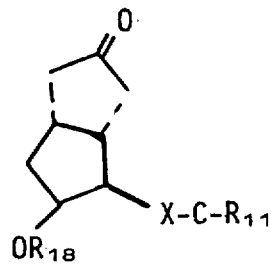

UNITED STATES PATENT OFFICE
CERTIFICATE OF CORRECTION

Patent No. 4,238,414     Dated  9 December 1980

Inventor(s) Douglas R. Morton, Jr.

It is certified that error appears in the above-identified patent and that said Letters Patent are hereby corrected as shown below:

Column 59, lines 15-25

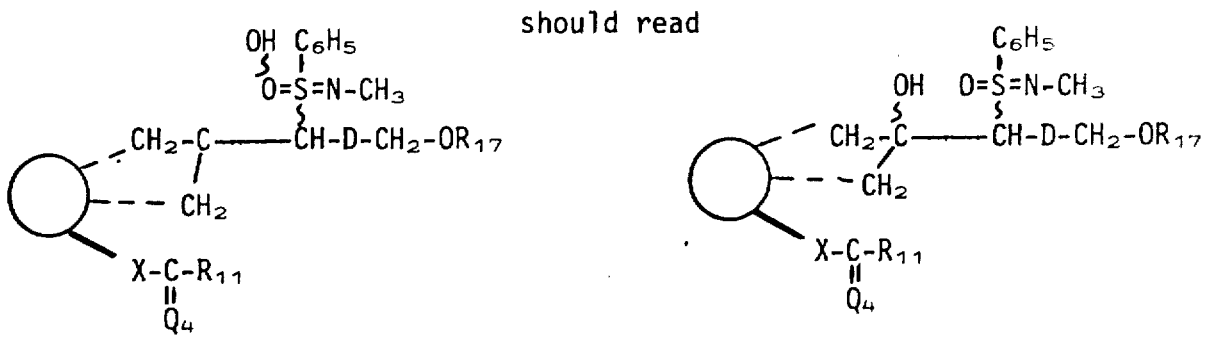

Column 80, line 14, "Formula JX(E)" should read -- Formula IX(E) --; line 46, "and 5.55-5.70 β," should read -- and 5.55-5.70 δ,--;

Column 88, line 35, " $(CH_3O)_2\overset{O}{\overset{\|}{P}}-CH_2\overset{O}{\overset{\|}{C}}-CH_2-O-$ " should read -- $(CH_3O)_2\overset{O}{\overset{\|}{P}}-CH_2-\overset{O}{\overset{\|}{C}}-CH_2-O-$ --;

Column 93, line 64, "11-bis(t-butyldimethylsilyl ether)" should read -- 1,11-bis(t-butyldimethylsilyl ether) --;

Column 95, line 49, "ps wherein $Q_1$ is" should read -- wherein $Q_1$ is --;

Column 97, lines 23-24, "according to claim 48" should read -- according to claim 47 --.

Signed and Sealed this

Twenty-ninth Day of September 1981

[SEAL]

Attest:

GERALD J. MOSSINGHOFF

Attesting Officer     Commissioner of Patents and Trademarks